US005616488A

United States Patent [19]

Sullivan et al.

[11] Patent Number: 5,616,488
[45] Date of Patent: Apr. 1, 1997

[54] IL-5 TARGETED RIBOZYMES

[75] Inventors: Sean Sullivan, Alameda, Calif.;
Kenneth G. Draper, Boulder, Colo.;
James McSwiggen, Boulder, Colo.;
Dan T. Stinchcomb, Boulder, Colo.

[73] Assignee: Ribozyme Pharmaceuticals, Inc., Boulder, Colo.

[21] Appl. No.: 319,492

[22] Filed: Oct. 7, 1994

Related U.S. Application Data

[63] Continuation-in-part of Ser. No. 989,849, Dec. 7, 1992, abandoned, and Ser. No. 8,895, Jan. 19, 1993, abandoned.

[51] Int. Cl.$^6$ ............................ C12N 15/05; C12Q 1/68; A61K 48/00

[52] U.S. Cl. ............................ 435/366; 435/6; 435/91.31; 435/320.1; 435/325; 536/23.1; 536/23.2; 536/24.5; 514/44

[58] Field of Search ........................ 435/6, 91.31, 172.3, 435/320.1, 240.2; 536/23.1, 23.2, 24.5; 514/44

[56] References Cited

U.S. PATENT DOCUMENTS

| 4,987,071 | 1/1991 | Cech et al. | 435/91.31 |
|---|---|---|---|
| 5,168,053 | 12/1992 | Altman et al. | 514/44 |
| 5,334,711 | 8/1994 | Sproat et al. | 536/24.5 |

FOREIGN PATENT DOCUMENTS

| 0360257 | 3/1990 | European Pat. Off. . |
|---|---|---|
| 0519463 | 12/1992 | European Pat. Off. . |
| 9103162 | 3/1991 | WIPO . |
| 9115580 | 10/1991 | WIPO . |
| 9118913 | 12/1991 | WIPO . |
| 9118624 | 12/1991 | WIPO . |
| 9118625 | 12/1991 | WIPO . |
| 9200080 | 1/1992 | WIPO . |
| 9207065 | 4/1992 | WIPO . |
| 9315187 | 5/1993 | WIPO . |
| 9323569 | 11/1993 | WIPO . |
| 9402595 | 3/1994 | WIPO . |
| 9413688 | 6/1994 | WIPO . |

OTHER PUBLICATIONS

Koizumi et al. Gene 117:179 (1992).
Tanabe et al. J. Biol. Chem. 262:16580 (1987).
Stull et al. Pharm. Res. 12:465 (1995).
Barinaga, Science 262:1512–1514 (1993).
Carter, "Adeno–Associated Virus Vectors," *Curr Opi. Biotech.* 3:533–539 (1992).
Cech, "Ribozymes and Their Medical Implications," *JAMA* 260:3030–3034 (1988).
Chen et al., "Multitarget–Ribozyme Directed to Cleave at up to Nine Highly Conserved HIV-1 env RNA Regions Inhibits HIV-1 Replication–Potential Effectiveness Against Most Presently Sequenced HIV-1 Isolates," *Nucleic Acids Research* 20:4581–4589 (1992).
Chowrira and Burke, "Extensive Phosphorothioate Substitution Yields Highly Active and Nuclease–Resistant Hairpin Ribozymes," *Nucleic Acids Res.* 20:2835–2840 (1992).

Collins and Olive, "Reaction Conditions and Kinetics of Self–Cleavage of a Ribozyme Derived From Neurospora VS RNA," *Biochemistry* 32:2795–2799 (1993).
Cook and Spicer, "Ch. 10 – Animal Models of Eosinophilia" in *Immunopharmacol. Eosinophils* ed. Smith and Cook eds., Academic, London U.K., pp. 193–216 (1993).
Dropulic et al., "Functional Characterization of a U5 Ribozyme: Intracellular Suppression of Human Immunodeficiency Virus Type I Expression," *Journal of Virology* 66:1432–1441 (1992).
Elroy–Stein and Moss, "Cytoplasmic Expression System Based on Constitutive Synthesis of Bacteriophage T7 RNA Polymerase in Mammalian Cells," *Proc. Natl. Acad. Sci. USA* 87:6743–6747 (1990).
Gao and Huang, "Cytoplasmic Expression of a Reporter Gene by Co–Delivery of T7 RNA Polymerase and T7 Promoter Sequence with Cationic Liposomes," *Nucleic Acids Res.* 21:2867–2872 (1993).
Gleich, "The eosinophil and bronchial asthma: Current understanding," *J. Allergy Clin. Immunol.* 85:422–436 (1990).
Guerrier–Takada et al., "The RNA Moiety of Ribonuclease P Is the Catalytic Subunit of the Enzyme," *Cell* 35:849–857 (1983).
Hampel et al., "'Hairpin' Catalytic RNA Model: Evidence for Helices and Sequence Requirement for Substrate RNA," *Nucleic Acids Research* 18:299–304 (1990).
Hampel and Tritz, "RNA Catalytic Properties of the Minimum (–)sTRSV Sequence," *Biochemistry* 28:4929–4933 (1989).
Haseloff and Gerlach, "Simple RNA Enzymes with New and Highly Specific Endoribonuclease Activities," *Nature* 334:585–591 (1988).
Hertel et al., "Numbering System for the Hammerhead," *Nucleic Acids Res.* 20:3252 (1992).
Hession et al., WO 9013300 provided as Chem Abstr. Acc # 114(25)–242037g.
Jaeger et al., "Improved Predictions of Secondary Structures for RNA," *Proc. Natl. Acad. Sci. USA* 86:7706–7710 (1989).
Jeffries and Symons, "A Catalytic 13–mer Ribozyme," *Nucleic Acids Research* 17:1371–1377 (1989).
Johnston and Hoth, *Science* 260:1286–1293 (1993).
Kashani–Sabet et al., "Reversal of the Malignant Phenotype by an Anti–*ras* Ribozyme," *Antisense Research & Development* 2:3–15 (1992).
Kay, "Asthma and Inflammation," *J. Allergy Clin. Immun.* 87:893–910 (1991).
Kim and Cech, "Three–dimensional model of the active site of the self–splicing rRNA precursor of *Tetrahymena*," *Proc. Natl. Acad. Sci. USA* 84:8788 (1987).
Koike and Takatsu, "IL and Its Receptor: Which Role Do They Play in the Immune Response?" *Int. Arch. Allergy. Immunol.* 104:1–9 (1994).

(List continued on next page.)

Primary Examiner—John LeGuyader
Attorney, Agent, or Firm—Lyon & Lyon

[57] ABSTRACT

Enzymatic RNA molecules which cleave IL-5 mRNA.

22 Claims, 6 Drawing Sheets

OTHER PUBLICATIONS

L'Huillier et al., "Cytoplasmic Delivery of Ribozymes Leads to Efficient Reduction in α–Lactalbumin mRNA Levels in C1271 Mouse," *Embo J.* 11:4411–4418 (1992).

Lieber et al., "Stable High–Level Gene Expression in Mammalian Cells by T7 Phage RNA Polymerase," *Methods Enzymol.* 217:47–66 (1993).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

Mamone et al., "Design of Mannerhead Ribozymes Targeted to Sequences in HIV, HSV, and the RAT ANF GENE," Abstract of Keystone, CO (May, 27, 1992).

Nabel et al., "Site–Specific Gene Expression in Vivo by Direct Gene Transfer Into the Arterial Wall," *Science* 249:1285–1288 (1990).

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Pavco et al., "Regulation of Self–Splicing Reactions by Antisense RNA," Abstract of Keystone, CO (May 27, 1992).

Perreault et al., "Mixed Deoxyribo– and Ribo–Oligonucleotides with Catalytic Activity," *Nature* 344:565–567 (1990).

Perrotta and Been, "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease–Resistant 2'–Modified Hammerhead Ribozymes," *Science* 253:314–317 (1991).

Rossi et al., "Ribozyme Mediated Intracellular Immunity to HIV–1 in CD4," *J. Cell Biochem.* Suppl 14A:D428 (1990).

Rossi et al, "Ribozymes as Anti–HIV–1 Therapeutic Agents: Principles, Applications, and Problems," *Aids Research and Human Retroviruses* 8:183–189 (1992).

Sarver et al., "Ribozymes as Potential Anti–HIV–1 Therapeutic Agents" *Science* 247:1222–1225 (1990).

Saville and Collins, "A Site–Specific Self–Cleavage Reaction Performed by a Novel RNA In Neurospora Mitochondria," *Cell* 61:685–696 (1990).

Saville and Collins, "RNA–Mediated Ligation of Self––Cleavage Products of a Neurospora Mitochondrial Plasmid Transcript," *Proc. Natl. Acad. Sci. USA* 88:8826–8830 (1991).

Scanlon et al., "Ribozyme–Mediated Cleavage of c-fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Sioud et al., *J. Mol. Biol.* 223:831–835 (1992).

Taira et al., "Construction of a novel RNA–transcript–trimming plasmid which can be used both in vitro in place of run–off and (G)–free transcriptions and in vivo as multi–sequences transcription vectors," *Nucleic Acids Research* 19:5125–5130 (1991).

Tanabe et al., *J. Biol. Chem.* 262:16580 (1987) provided as BIOSIS Abstr. 85047487.

Uhlenbeck, "A Small Catalytic Oligoribonucleotide," *Nature* 328:596–600 (1987).

Usman et al., "Automated Chemical Synthesis or Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Usman and Cedergren, "Exploiting the chemical synthesis of RNA," *TIBS* 17:334–339 (1992).

van Oosterhout et al., "Effect of Anti–IL–5 and IL–5 on Airway Hyperreactivity and Eosinophils in Guinea Pigs," *Am. Rev. Respir. Dis.* 147:548–552 (1993).

Varga et al., "L–Tryptophan and the Eosinophilia–Myalgia Syndrome: Current Understanding of the Etiology and Pathogenesis," *J. Invest. Dermatol.* 100:97s–105S (1993).

Ventura et al., "Activation of HIV–Specific Ribozyme Activity by Self–Cleavage," *Nucleic Acids Research* 21:3249–3255 (1993).

Weerasinghe et al., "Resistance to Human Immunodeficiency Virus Type 1 (HIV–1) Infection in Human CD4$^+$ Lymphocyte–Derived Cell Lines Conferred by Using Retroviral Vetors Expressing an HIV–1 RNA–Specific Ribozyme," *Journal of Virology* 65:5531–5534 (1994).

Willard et al., "Recombinant Adenovirus in an Efficient Vector for In Vivo Gene Transfer and can be Preferentially Directed at Vascular Endothelium or Smooth Muscle Cells," *Circulation – Abstracts from the 6th Scientific Sessions*, New Orleans Convention Center, New Orleans, Louisiana, Nov. 16–19, 1992, 86:I–473 at 1880.

Woolf et al., "Specificity of Antisense Oligonucleotides in vivo," *Proc. Natl. Acad. Sci. USA* 89:7305–7309 (1992).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Zabner et al., "Adenovirus–Mediated Gene Transfer Transiently Corrects the Chloride Transport Defect in Nasal Epithelia of Patients with Cystic Fibrosis," *Cell* 75:207–216 (1993).

Zhou et al., "Synthesis of Functional mRNA in Mammalian Cells by Bacteriophage T3 RNA Polymerase," *Mol. Cell. Biol.* 10:4529–4537 (1990).

Ballantyne et al., "Nucleotide sequence of the cDNA for murine intercellular adhesion molecule–1 (ICAM–1)," *Nucleic Acids Research* 17:5853 (1989).

Cotten, "The in vivo application of ribozymes," *TIBTECH* 8:174–178 (1990).

Edgington, "Ribozymes: Stop Making Sense," *Biotechnology* 10:256–262 (1992).

Kita et al., "Sequence and expression of rat ICAM–1," *Biochem. Biophys. Acta* 1131:108–110 (1992).

Simons et al., "ICAM, an adhesion ligand of LFA–1, is homologous to the neutral cell adhesion molecule NCAM," *Nature* 331:624–627 (1988).

1

IL-5 TARGETED RIBOZYMES

RELATED APPLICATIONS

This application is a continuation-in-part of U.S. Ser. No. 07/989,849 (filed Dec. 7, 1992) now abandoned, and U.S. Ser. No. 08/008,895 (filed Jan. 19, 1993), now abandoned.

FIELD OF THE INVENTION

The present invention relates to therapeutic compositions and methods for the treatment or diagnosis of diseases or conditions related to IL-5 levels, such as asthma.

BACKGROUND OF THE INVENTION

The following is a brief description of the physiology of asthma. The discussion is not meant to be complete and is provided only for understanding of the invention that follows. This summary is not an admission that any of the work described below is prior art to the claimed invention.

The term "asthma" originally meant "difficult breathing." It now refers to a number of diseases involving constriction of the airways. Intrinsic asthma is characterized by recurrent episodes of airway obstruction that resolve spontaneously or after treatment. The etiology of intrinsic asthma is unknown.

Extrinsic asthma is associated with hyperresponsiveness of the airways to a variety of inhaled stimuli. These stimuli have little or no effect on normal subjects. Clinical results obtained from bronchoalveolar lavage and lung biopsies show good correlation between infiltration of activated T helper cells and eosinophils and hyperresponsiveness of the lungs.

Asthma affects nearly 5% of the population in industrialized nations, yet it is underdiagnosed and undertreated. There is evidence that the incidence and prevalence of asthma are rising. These trends are occurring despite increases in the available therapies for asthma, which suggests that current methods of treating asthma are inadequate or not being utilized appropriately. Recently, it has been recognized that chronic asthma involves a characteristic inflammatory response in the airways.

Although it has long been acknowledged that fatal asthma is associated with inflammatory changes in the submucosal surfaces of the airways, it is now apparent that inflammation is present in patients with very mild asthma. Biopsies of patients have shown that infiltration of immune cells, especially eosinophils and lymphocytes, and epithelial shedding are prominent features. Further, there is a strong correlation between the degree of eosinophilia and the degree of bronchial hyperresponsiveness. Eosinophils are localized to areas of epithelial damage in the airways of patients. The basic proteins released by the eosinophils may be responsible for the damage observed in these patients. The role of mast cells and neutrophils in the disease is uncertain. Lymphocytes are present at the sites of tissue damage, but their role may be as mediators to amplify the eosinophilic response. In fact, interleukin-5, which is released by T-lymphocytes, is important in retaining and priming eosinophil action in the airway.

Mild, periodic episodes of bronchoconstriction can be managed by inhalation of $\beta_2$-adrenergic antagonists. Severe chronic asthma may require several agents including systemic administration of adrenocorticosteroids on a regular basis. Other treatments include theophylline (a smooth muscle relaxant and a bronchodilator; a strong CNS activator more potent than caffeine). Cromolyn Sodium, an inhibitor of degranulation of pulmonary mast cells by inhibiting release of inflammatory mediators. Therapeutic effects are prophylactic and no toxic side effects have been associated with these drugs.

SUMMARY OF THE INVENTION

This invention relates to ribozymes, or enzymatic RNA molecules, directed to cleave mRNA species encoding IL-5. In particular, applicant describes the selection and function of ribozymes capable of cleaving this RNA and their use to reduce activity of IL-5 in various tissues to treat the diseases discussed herein. Such ribozymes are also useful for diagnostic applications.

Ribozymes that cleave IL-5 mRNA represent a novel therapeutic approach to inflammatory disorders like asthma. The invention features use of ribozymes to treat chronic asthma, e.g., by inhibiting the synthesis of IL-5 in lymphocytes and preventing the recruitment and activation of eosinophils. Applicant indicates that ribozymes are able to inhibit the secretion of IL-5 and that the catalytic activity of the ribozymes is required for their inhibitory effect. Those of ordinary skill in the art, will find that it is clear from the examples described that other ribozymes that cleave IL-5 encoding mRNAs may be readily designed and are within the invention.

A number of cytokines besides IL-5 may also be involved in the activation of inflammation in asthmatic patients, including platelet activating factor, IL-1, IL-3, IL-4, GM-CSF, TNF-$\alpha$, gamma interferon, VCAM, ILAM-1, ELAM-1 and NF-$\kappa$B. In addition to these molecules, it is appreciated that any cellular receptors which mediate the activities of the cytokines are also good targets for intervention in inflammatory diseases. These targets include, but are not limited to, the IL-1R and TNF-$\alpha$R on keratinocytes, epithelial and endothelial cells in airways. Recent data suggest that certain neuropeptides may play a role in asthmatic symptoms. These peptides include substance P, neurokinin A and calcitonin-gene-related peptides. These target genes may have more general roles in inflammatory diseases, but are currently assumed to have a role only in asthma.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf, T. M., et al., 1992, *Proc. Natl. Acad. Sci. USA,* 89, 7305–7309). Thus, the specificity of action of a ribozyme is greater than that of an antisense oligonucleotide binding the same RNA site.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al., 1992, *Aids Research and Human Retroviruses* 8, 183, of hairpin motifs by Hampel et al., EPA 0360257, Hampel and Tritz, 1989 *Biochemistry* 28, 4929, and Hampel et al., 1990 *Nucleic Acids Res.* 18, 299, and an example of the hepatitis delta virus motif is described by Perrotta and Been, 1992 *Biochemistry* 31, 16; of the RNaseP motif by Guerrier-Takada et al., 1983 *Cell* 35, 849, Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

The invention provides a method for producing a class of enzymatic cleaving agents which exhibit a high degree of specificity for the RNA of a desired target. The enzymatic nucleic acid molecule is preferably targeted to a highly conserved sequence region of a target IL-5 encoding mRNA such that specific treatment of a disease or condition can be provided with either one or several enzymatic nucleic acids. Such enzymatic nucleic acid molecules can be delivered exogenously to specific cells as required. Alternatively, the ribozymes can be expressed from DNA or RNA vectors that are delivered to specific cells.

Synthesis of nucleic acids greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure. However, these catalytic RNA molecules can also be expressed within cells from eukaryotic promoters (e.g., Scanlon et al., 1991, *Proc. Natl. Acad. Sci. USA,* 88, 10591–5; Kashani-Sabet et al., 1992 *Antisense Res. Dev.,* 2, 3–15; Dropulic et al., 1992 *J. Virol,* 66, 1432–41; Weerasinghe et al., 1991 *J. Virol,* 65, 5531–4; Ojwang et al., 1992 *Proc. Natl. Acad. Sci. USA* 89, 10802–6; Chen et al., 1992 *Nucleic Acids Res.,* 20, 4581–9; Sarver et al., 1990 *Science* 247, 1222–1225). Those skilled in the art realize that any ribozyme can be expressed in eukaryotic cells from the appropriate DNA vector. The activity of such ribozymes can be augmented by their release from the primary transcript by a second ribozyme (Draper et al., PCT WO93/23569, and Sullivan et al., PCT WO94/02595, both hereby incorporated in their totality by reference herein; Ohkawa et al., 1992 *Nucleic Acids Symp. Ser.,* 27, 15–6; Taira et al., 1991, *Nucleic Acids Res.,* 19, 5125–30; Ventura et al., 1993 *Nucleic Acids Res.,* 21, 3249–55).

Ribozyme therapy, due to its exquisite specificity, is particularly well-suited to target mRNA encoding factors that contribute to disease pathology. Thus, ribozymes that cleave IL-5 mRNA may represent novel therapeutics for the treatment of asthma.

Thus, in a first aspect, the invention features ribozymes that inhibit IL-5 production. These chemically or enzymatically synthesized RNA molecules contain substrate binding domains that bind to accessible regions of their target mRNAs. The RNA molecules also contain domains that catalyze the cleavage of RNA. The RNA molecules are preferably ribozymes of the hammerhead or hairpin motif. Upon binding, the ribozymes cleave the target IL-5 encoding mRNAs, preventing translation and IL-5 protein accumulation. In the absence of the expression of the target gene, a therapeutic effect may be observed.

By "inhibit" is meant that the activity or level of IL-5 encoding mRNA is reduced below that observed in the absence of the ribozyme, and preferably is below that level observed in the presence of an inactive RNA molecule able to bind to the same site on the mRNA, but unable to cleave that RNA.

Such ribozymes are useful for the prevention of the diseases and conditions discussed above, and any other diseases or conditions that are related to the level of IL-5 activity in a cell or tissue. By "related" is meant that the inhibition of IL-5 mRNA and thus reduction in the level of IL-5 activity will relieve to some extent the symptoms of the disease or condition.

Ribozymes are added directly, or can be complexed with cationic lipids, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers. In preferred embodiments, the ribozymes have binding arms which are complementary to the sequences in Tables II, IV, VI and VII. Examples of such ribozymes are shown in Tables III, V–VII. Examples of such ribozymes consist essentially of sequences defined in these Tables. By "consists essentially of" is meant that the active ribozyme contains an enzymatic center equivalent to those in the examples, and binding arms able to bind mRNA such that cleavage at the target site occurs. Other sequences may be present which do not interfere with such cleavage.

In another aspect of the invention, ribozymes that cleave target molecules and inhibit IL-5 activity are expressed from transcription units inserted into DNA, RNA, or viral vectors. Preferably, the recombinant vectors capable of expressing the ribozymes are locally delivered as described above, and transiently persist in target cells. Once expressed, the ribozymes cleave the target mRNA. The recombinant vectors are preferably DNA plasmids, adenovirus, retroviral or adeno-associated virus vectors. However, other mammalian cell vectors that direct the expression of RNA may be used for this purpose.

Other features and advantages of the invention will be apparent from the following description of the preferred embodiments thereof, and from the claims.

DESCRIPTION OF THE PREFERRED EMBODIMENTS

The drawings will first briefly be described.

Drawings FIG. 1 is a diagrammatic representation of the hammerhead ribozyme domain known in the art. Stem II can be ≧2 base-pairs long.

FIG. 2a is a diagrammatic representation of the hammerhead ribozyme domain known in the art; FIG. 2b is a diagrammatic representation of the hammerhead ribozyme as divided by Uhlenbeck (1987, *Nature*, 327, 596–600) into a substrate and enzyme portion; FIG. 2c is a similar diagram showing the hammerhead divided by Haseloff and Gerlach (1988, *Nature*, 334, 585–591) into two portions; and FIG. 2d is a similar diagram showing the hammerhead divided by Jeffries and Symons (1989, *Nucl. Acids. Res.*, 17, 1371–1371) into two portions.

FIG. 3 is a representation of the general structure of the hairpin ribozyme domain known in the art. H is A, U or C. Y is U or C. N is A, U, G, or C. N' is the complementary sequence of N. Helix 4 can be ≧2 base-pairs long.

Figure 6:
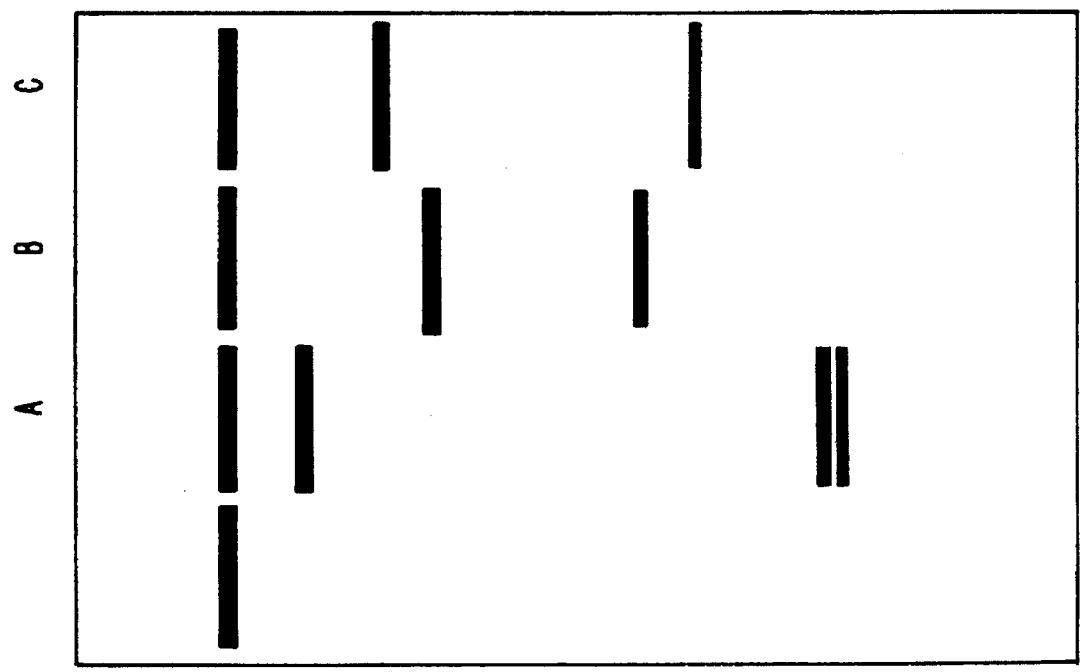
Figure 6:
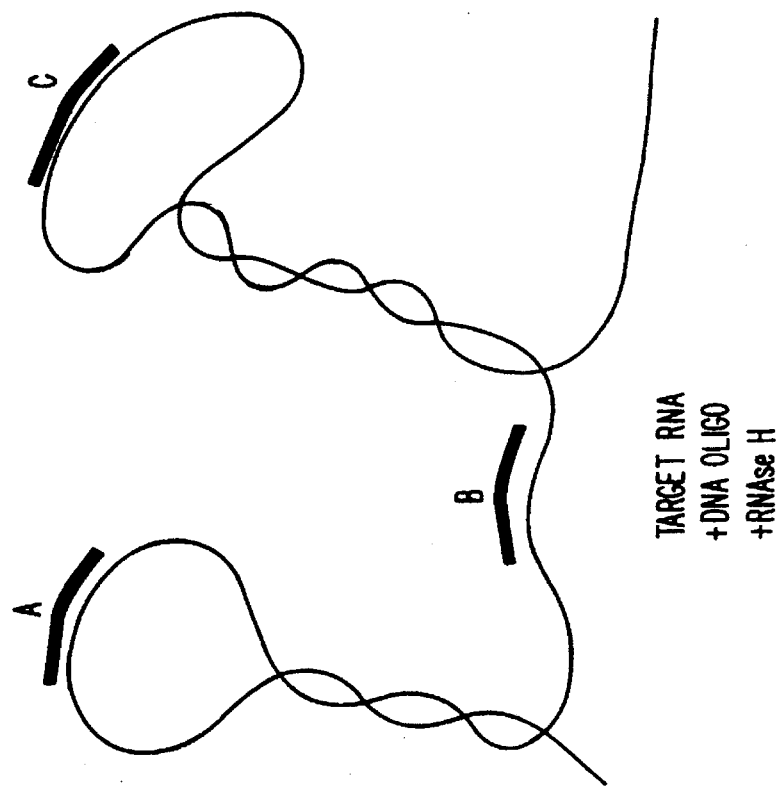

FIG. 6 is a schematic representation of an RNAseH accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

Ribozymes

Ribozymes of this invention block to some extent IL-5 expression and can be used to treat disease or diagnose such disease. Ribozymes will be delivered to cells in culture and to cells or tissues in animal models of asthma (Clutterbuck et al., 1989 supra; Garssen et al., 1991 *Am. Rev. Respir. Dis.* 144, 931–938; Larsen et al., 1992 *J. Clin. Invest.* 89, 747–752; Mauser et al., 1993 supra). Ribozyme cleavage of IL-5 mRNA in these systems may prevent inflammatory cell function and alleviate disease symptoms.

Target Sites

Targets for useful ribozymes can be determined as disclosed in Draper et al supra, Sullivan et al., supra, as well as by Draper et al., "Method and reagent for treatment of arthritic conditions U.S. Ser. No. 08/152,487, filed Nov. 12, 1993, and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described. Such ribozymes can also be optimized and delivered as described therein. While specific examples to mouse and human RNA are provided, those in the art will recognize that the equivalent human RNA targets described can be used as described below. Thus, the same target may be used, but binding arms suitable for targeting human RNA sequences are present in the ribozyme. Such targets may also be selected as described below.

The sequence of human and mouse IL-5 mRNA were screened for accessible sites using a computer folding algorithm. Potential hammerhead or hairpin ribozyme cleavage sites were identified. These sites are shown in Tables II, IV, and VI–VII. (All sequences are 5' to 3' in the tables.) While mouse and human sequences can be screened and ribozymes thereafter designed, the human targeted sequences are of most utility. However, as discussed in Stinchcomb et al., "Method and Composition for Treatment of Restenosis and Cancer Using Ribozymes," filed May 18, 1994, U.S. Ser. No. 08/245,466, mouse targeted ribozymes are useful to test efficacy of action of the ribozyme prior to testing in humans. The nucleotide base position is noted in the Tables as that site to be cleaved by the designated type of ribozyme. (In Table III, lower case letters indicate positions that are not conserved between the Human and the Mouse IL-5 sequences.)

Hammerhead or hairpin ribozymes are designed that could bind and are individually analyzed by computer folding (Jaeger et al., 1989 *Proc. Natl. Acad. Sci. USA*, 86, 7706–7710) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

Referring to FIG. 6, mRNA is screened for accessible cleavage sites by the method described generally in McSwiggen, U.S. patent application Ser. No. 07/883,849 filed on May 1, 1992, entitled "Assay for ribozyme target site", hereby incorporated by reference herein. Briefly, DNA oligonucleotides representing potential hammerhead or hairpin ribozyme cleavage sites are synthesized. A polymerase chain reaction is used to generate a substrate for T7 RNA polymerase transcription from human or murine IL-5 cDNA clones. Labeled RNA transcripts are synthesized in vitro from the two templates. The oligonucleotides and the labeled transcripts are annealed, RNAseH is added and the mixtures are incubated for the designated times at 37° C. Reactions are stopped and RNA separated on sequencing polyacrylamide gels. The percentage of the substrate cleaved is determined by autoradiographic quantitation using a Phosphor Imaging system. From these data, hammerhead ribozyme sites are chosen as the most accessible.

Ribozymes of the hammerhead or hairpin motif are designed to anneal to various sites in the mRNA message. The binding arms are complementary to the target site sequences described above. The ribozymes are chemically synthesized. The method of synthesis used follows the procedure for normal RNA synthesis as described in Usman et al., 1987 *J. Am. Chem. Soc.*, 109, 7845–7854 and in Scaringe et al., 1990 *Nucleic Acids Res.*, 18, 5433–5441 and makes use of common nucleic acid protecting and coupling groups, such as dimethoxytrityl at the 5'-end, and phosphoramidites at the 3'-end. The average stepwise coupling yields were >98%. Inactive ribozymes were synthesized by substituting a U for $G_5$ and a U for $A_{14}$ (numbering from Hertel et al., 1992 *Nucleic Acids Res.*, 20, 3252). Hairpin ribozymes are synthesized in two parts and annealed to reconstruct the active ribozyme (Chowrira and Burke, 1992 *Nucleic Acids Res.*, 20, 2835–2840). All ribozymes are modified extensively to enhance stability by modification with nuclease resistant groups, for example, 2'-amino, 2'-C-allyl, 2'-flouro, 2'-o-methyl, 2'-H (for a review see Usman and Cedergren, 1992 *TIBS* 17, 34). Ribozymes are purified by gel electrophoresis using general methods or are purified by high pressure liquid chromatography (HPLC; See Usman et al., Synthesis, deprotection, analysis and purification of RNA and ribozymes, filed May, 18, 1994, U.S. Ser. No. 08/245,736 the totality of which is hereby incorporated herein by reference) and are resuspended in water.

The sequences of the chemically synthesized ribozymes useful in this study are shown in Tables III, V–VII. Those in the art will recognize that these sequences are representative only of many more such sequences where the enzymatic portion of the ribozyme (all but the binding arms) is altered to affect activity. For example, stem loop II sequence of hammerhead ribozymes listed in Tables III and V (5'-GGCCGAAAGGCC-3') can be altered (substitution, deletion and/or insertion) to contain any sequence provided, a minimum of two base-paired stem structure can form. Similarly, stem-loop IV sequence of hairpin ribozymes listed in Tables VI and VII (5'-CACGUUGUG-3') can be altered (substitution, deletion and/or insertion) to contain any sequence provided, a minimum of two base-paired stem structure can form. The sequences listed in Tables III, V–VII may be formed of ribonucleotides or other nucleotides or non-nucleotides. Such ribozymes are equivalent to the ribozymes described specifically in the Tables.

Optimizing Ribozyme Activity

Figure 2B:
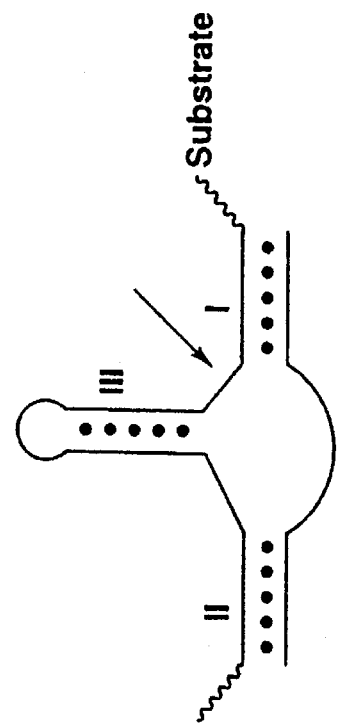
Figure 2D:
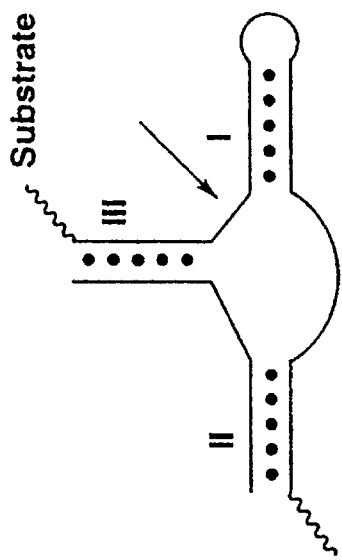
Figure 2A:
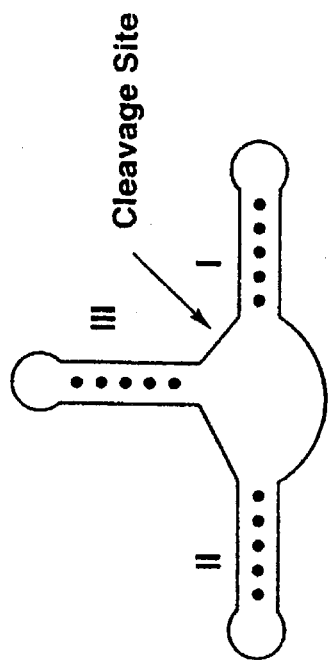
Figure 2C:
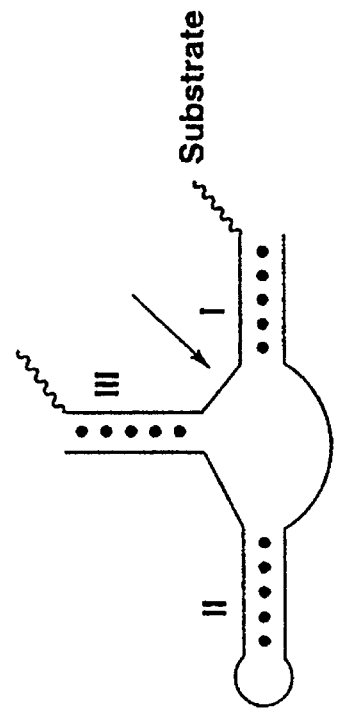

Ribozyme activity can be optimized as described by Stinchcomb et al., supra. The details will not be repeated here, but include altering the length of the ribozyme binding arms (stems I and III, see FIG. 2c), or chemically synthesizing ribozymes with modifications that prevent their degradation by serum ribonucleases (see e.g., Eckstein et al, International Publication No. WO 92/07065; Perrault et al, 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et al., International Publication No. WO 91/03162, as well as Usman, N. et al., U.S. patent application Ser. No. 07/829,729, Sproat, European Patent Application 92110298.4 and U.S. Pat. No. 5,334,711 and Jennings et al., WO 94/13688 which describe various chemical modifications that can be made to the sugar moieties of enzymatic RNA molecules. All these publications are hereby incorporated by reference herein.), modifications which enhance their efficacy in cells, and removal of stem II bases to shorten RNA synthesis times and reduce chemical requirements.

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., supra which have been incorporated by reference herein.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. USA*, 87, 6743–7; Gao and Huang 1993 *Nucleic Acids Res.*, 21, 2867–72; Lieber et al., 1993 *Methods Enzymol.*, 217, 47–66; Zhou et al., 1990 *Mol. Cell. Biol.*, 10, 4529–37). Several investigators have demonstrated that ribozymes expressed from such promoters can function in mammalian cells (e.g. Kashani-Sabet et al., 1992 *Antisense Res. Dev.*, 2, 3–15; Ojwang et al., 1992 *Proc. Natl. Acad. Sci. USA*, 89, 10802–6; Chen et al., 1992 *Nucleic Acids Res.*, 20, 4581–9; Yu et al., 1993 *Proc. Natl. Acad. Sci. USA*, 90, 6340–4; L'Huillier et al., 1992 *EMBO J.* 11, 4411–8; Lisziewicz et al., 1993 *Proc. Natl. Acad. Sci. U.S.A.*, 90, 8000–4). The above ribozyme transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

In a preferred embodiment of the invention, a transcription unit expressing a ribozyme that cleaves IL-5 RNA is inserted into a plasmid DNA vector or an adenovirus DNA virus or adeno-associated virus (AAV) vector. Both viral vectors have been used to transfer genes to the lung and both vectors lead to transient gene expression (Zabner et al., 1993 *Cell* 75, 207; Carter, 1992 *Curr. Opi. Biotech.* 3, 533). The adenovirus vector is delivered as recombinant adenoviral particles. The DNA may be delivered alone or complexed with vehicles (as described for RNA above). The recombinant adenovirus or AAV particles are locally administered to the site of treatment, e.g., through incubation or inhalation in vivo or by direct application to cells or tissues ex vivo.

EXAMPLE 1

IL-5 Hammerhead Ribozymes

By engineering ribozyme motifs we have designed several ribozymes directed against IL-5 mRNA sequences. These ribozymes are synthesized with modifications that improve their nuclease resistance. The ability of ribozymes to cleave IL-5 target sequences in vitro is evaluated.

The ribozymes will be tested for function in vivo by analyzing IL-5 expression levels. Ribozymes will be delivered to cells by incorporation into liposomes, by complexing with cationic lipids, by microinjection, or by expression from DNA vectors. IL-5 expression will be monitored by biological assays, ELISA, by indirect immunofluoresence, and/or by FACS analysis. IL-5 mRNA levels will be assessed by Northern analysis, RNAse protection or primer extension analysis or quantitative RT-PCR. Ribozymes that block the induction of IL-5 activity and/or IL-5 mRNA by more than 90% will be identified.

Uses

Interleukin 5 (IL-5), a cytokine produced by CD4+ T helper cells and mast cells, was originally termed B cell growth factor II (reviewed by Takatsu et al., 1988 *Immunol. Rev.* 102, 107). It stimulates proliferation of activated B cells and induces production of IgM and IgA. IL-5 plays a major role in eosinophil function by promoting differentiation (Clutterbuck et al., 1989 *Blood* 73, 1504–12), vascular adhesion (Walsh et al., 1990 *Immunology* 71, 258–65) and in vitro survival of eosinophils (Lopez et al., 1988 *J. Exp. Med.* 167, 219–24). This cytokine also enhances histamine release from basophils (Hirai et al., 1990 *J. Exp. Med.* 172, 1525–8). The following summaries of clinical results support the selection of IL-5 as a primary target for the treatment of asthma:

Several studies have shown a direct correlation between the number of activated T cells and the number of eosinophils from asthmatic patients vs. normal patients (Oehling et al., 1992 J. Investig. Allergol. Clin. Immunol. 2, 295–9). Patents with either allergic asthma or intrinsic asthma were treated with corticosteroids. The bronchoalveolar lavage was monitored for eosinophils, activated T helper cells and recovery of pulmonary function over a 28 to 30 day period. The number of eosinophils and activated T helper cells decreased progressively with subsequent improvement in pulmonary function compared to intrinsic asthma patients with no corticosteroid treatment.

Bronchoalveolar lavage cells were screened for production of cytokines using in situ hybridization for mRNA. In situ hybridization signals were detected for IL-2, IL-3, IL-4, IL-5 and GM-CSF. Upregulation of mRNA was observed for IL-4, IL-5 and GM-CSF (Robinson et al., 1993 *J. Allergy Clin. Immunol.* 92, 313–24). Another study showed that upregulation of IL-5 transcripts from allergen challenged vs. saline challenged asthmatic patients (Krishnaswamy et al., 1993 *Am. J. Respir. Cell. Mol. Biol.* 9, 279–86).

An 18 patient study was performed to determine a mechanism of action for corticosteroid improvement of asthma symptoms. Improvement was monitored by methacholine responsiveness. A correlation was observed between the methacholine responsiveness, a reduction in the number of eosinophils, a reduction in the number of cells expressing IL-4 and IL-5 mRNA and an increase in number of cells expressing interferon-gamma.

Bronchial biopsies from 15 patients were analyzed 24 hours after allergen challenge (Bentley et al., 1993 *Am. J. Respir. Cell. Mol. Biol.* 8, 35–42). Increased numbers of eosinophils and IL-2 receptor positive cells were found in the biopsies. No differences in the numbers of total leukocytes, T lymphocytes, elastase-positive neutrophils, macrophages or mast cell subtypes were observed. The number of cells expressing IL-5 and GM-CSF mRNA significantly increased.

In another patient study, the eosinophil phenotype was the same for asthmatic patients and normal individuals. However, eosinophils from asthmatic patients had greater leukotriene C4 producing capacity and migration capacity. There were elevated levels of IL-3, IL-5 and GM-CSF in the circulation of asthmatics but not in normal individuals (Bruijnzeel et al., 1992 *Schweiz. Med. Wochenschr.* 122, 298–301).

Efficacy of antibody to IL-5 was assessed in a guinea pig asthma model. The animals were challenged with ovalbumin and assayed for eosinophilia and the responsiveness to the bronchioconstriction substance P. A 30 mg/kg dose of antibody administered i.p. blocked ovalbumin-induced increased sensitivity to substance P and blocked increases in bronchoalveolar and lung tissue accumulation of eosinophils (Mauser et al., 1993 *Am. Rev. Respir. Dis.* 148, 1623–7). In a separate study guinea pigs challenged for eight days with ovalbumin were treated with monoclonal antibody to IL-5. Treatment produced a reduction in the number of eosinophils in bronchoalveolar lavage. No reduction was observed for unchallenged guinea pigs and guinea pigs treated with a control antibody. Antibody treatment completely inhibited the development of hyperreactivity to histamine and arecoline after ovalbumin challenge (van Oosterhout et al., 1993 *Am. Rev. Respir. Dis.* 147, 548–52)

Results obtained from human clinical analysis and animal studies indicate the role of activated T helper cells, cytokines and eosinophils in asthma. The role of IL-5 in eosinophil development and function makes IL-5 a good candidate for target selection. The antibody studies neutralized IL-5 in the circulation thus preventing eosinophilia. Inhibition of the production of IL-5 will achieve the same goal.

Asthma—a prominent feature of asthma is the infiltration of eosinophils and deposition of toxic eosinophil proteins (e.g. major basic protein, eosinophil-derived neurotoxin) in the lung. A number of T-cell-derived factors like IL-5 are responsible for the activation and maintainance of eosinophils (Kay, 1991 *J. Allergy Clin. Immun.* 87, 893). Inhibition of IL-5 expression in the lungs can decrease the activation of eosinophils and will help alleviate the symptoms of asthma.

Atopy—is characterized by the developement of type I hypersensitive reactions associated with exposure to certain environmental antigens. One of the common clinical manifestations of atopy is eosinophilia (accumulation of abnormally high levels of eosinophils in the blood). Antibodies against IL-5 have been shown to lower the levels of eosinophils in mice (Cook et al., 1993 in *Immunopharmacol. Eosinophils* ed. Smith and Cook, pp. 193–216, Academic, London, UK)

Parasitic infection-related eosinophilia—infections with parasites like helminths, can lead to severe eosinophilia (Cook et al., 1993 supra). Animal models for eosinophilia suggest that infection of mice, for example, can lead to blood, peritoneal and/or tissue eosinophilia, all of which seem to be lowered to varying degrees by antibodies directed against IL-5.

Pulmonary infiltration eosinophilia—is characterised by accumulation of high levels of eosinophils in pulmonary parenchyma (Gleich, 1990 *J. Allergy Clin. Immunol.* 85, 422).

L-Tryptophan-associated eosinophilia-myalgia syndrome (EMS)—The EMS disease is closely linked to the consumption of L-tryptophan, an essential aminoacid used to treat conditions like insomnia (for review see Varga et al., 1993 *J Invest. Dermatol.* 100, 97s). Pathologic and histologic studies have demonstrated high levels of eosinophils and mononuclear inflammatory cells in patients with EMS. It appears that IL-5 and transforming growth factor play a significant role in the development of EMS (Varga et al., 1993 supra) by activating eosinophils and other inflammatory cells.

Thus, ribozymes of the present invention that cleave IL-5 mRNA and thereby IL-5 activity have many potential therapeutic uses, and there are reasonable modes of delivering the ribozymes in a number of the possible indications. Development of an effective ribozyme that inhibits IL-5 function is described above; available cellular and activity assays are numerous, reproducible, and accurate. Animal models for IL-5 function and for each of the suggested disease targets exist (Cook et al., 1993 supra) and can be used to optimize activity.

Diagnostic Uses

Ribozymes of this invention may be used as diagnostic tools to examine genetic drift and mutations within diseased cells. They can also be used to assess levels of the target RNA molecule. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNA associated with an IL-5 related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., IL-5) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively. Other embodiments are within the following claims.

TABLE I

Group I Introns

Size: ~200 to >1000 nucleotides.
Requires a U in the target sequence immediately 5' of the cleavage site.
Binds 4–6 nucleotides at 5' side of cleavage site.
Over 75 known members of this class. Found in Tetrahymena thermophila rRNA, fungal mitochondria, chloroplasts, phage T4, blue-green algae, and others.
RNAseP RNA (M1 RNA)

Figure 1:
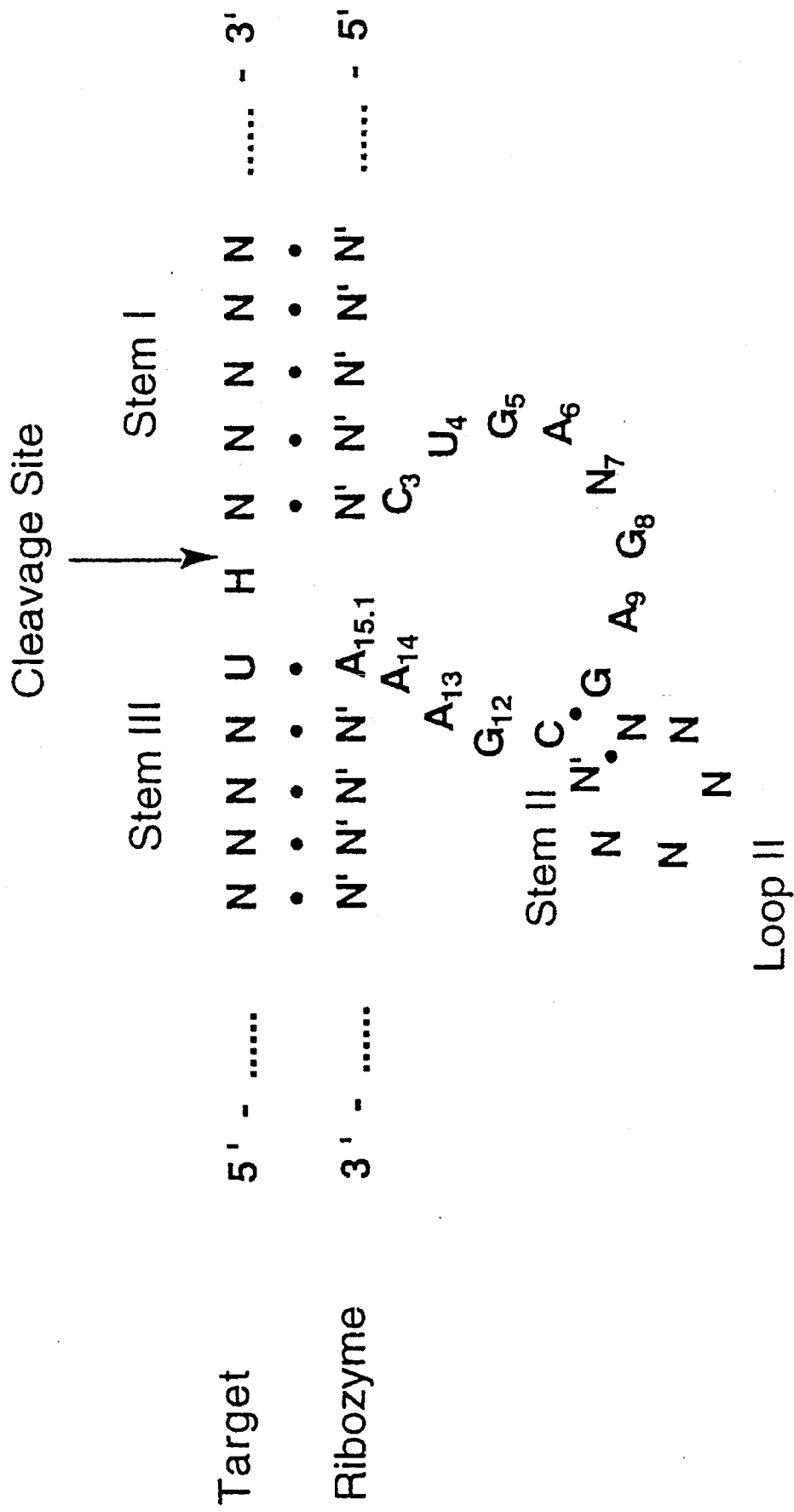
Figure 3:
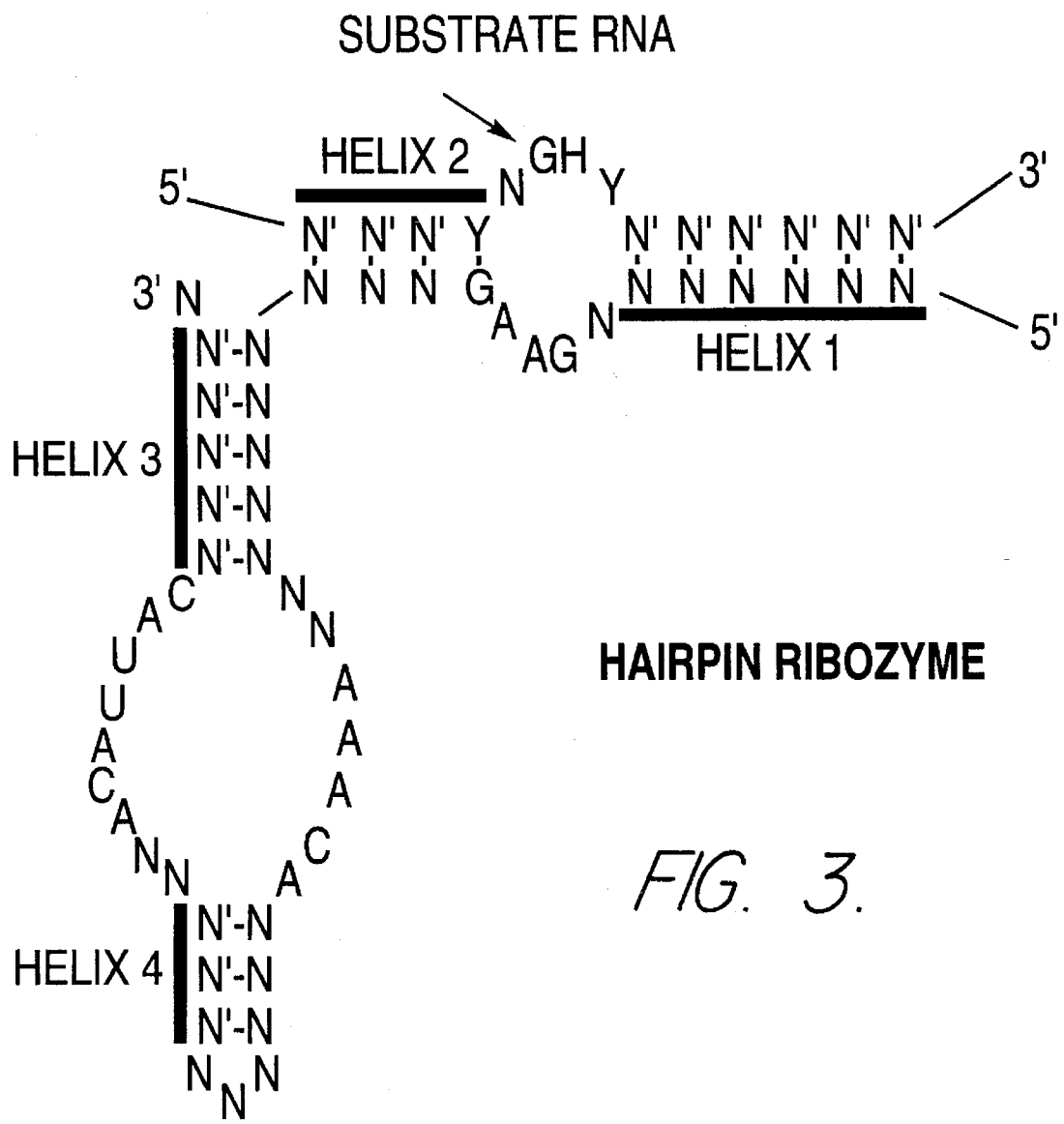
Figure 4:
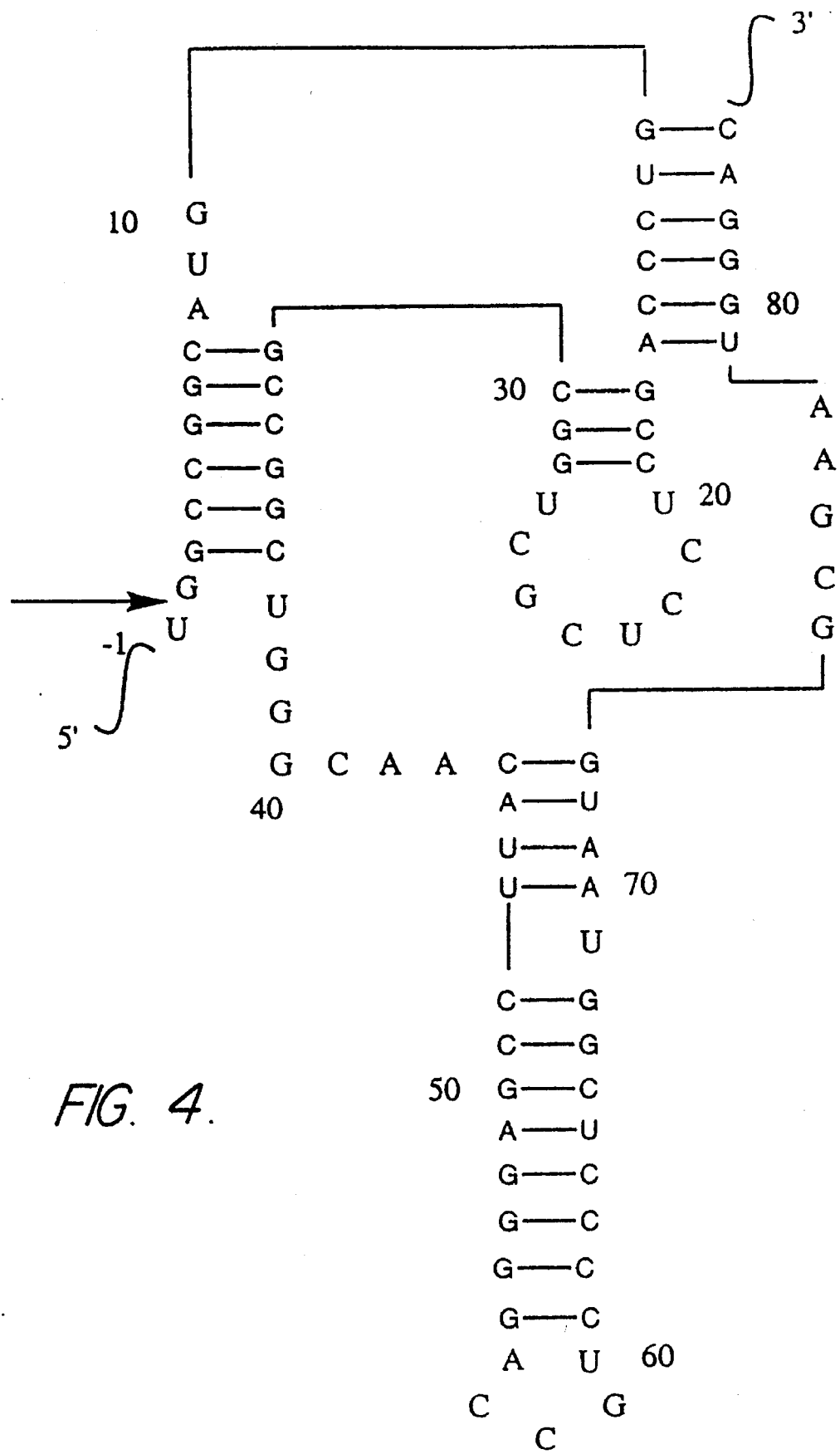
FIG. 4 is a representation of the general structure of the hepatitis delta virus ribozyme domain known in the art.
Figure 5:
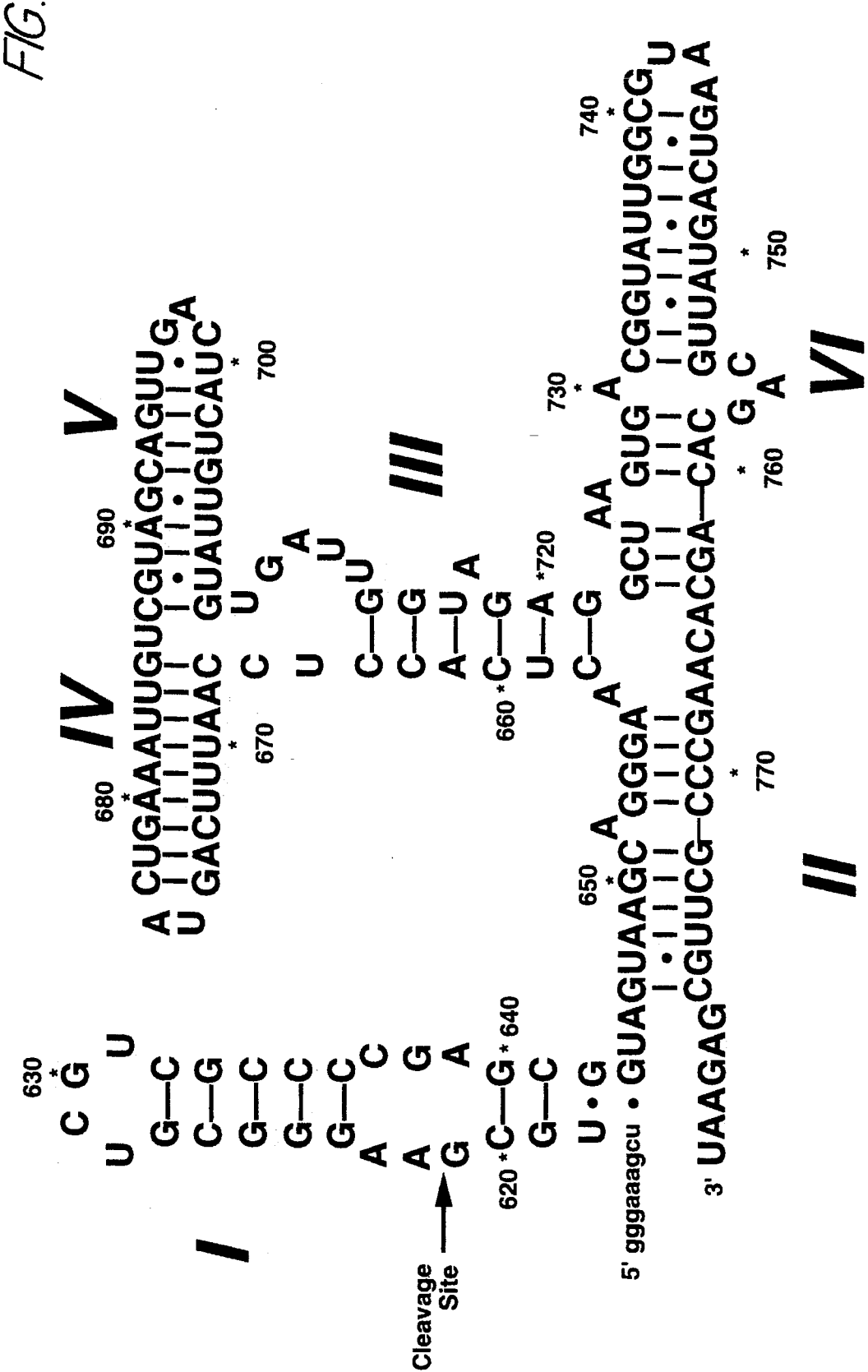
FIG. 5 is a representation of the general structure of the VS RNA ribozyme domain known in the art.

Size: ~290 to 400 nucleotides.
RNA portion of a ribonucleoprotein enzyme. Cleaves tRNA precursors to form mature tRNA.
Roughly 10 known members of this group all are bacterial in origin.
Hammerhead Ribozyme Size: ~13 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (FIGS. 1 and 2)
Hairpin Ribozyme Size: ~50 nucleotides.
Requires the target sequence GUC immediately 3' of the cleavage site.
Binds 4–6 nucleotides at 5' side of the cleavage site and a variable number to the 3' side of the cleavage site.
Only 3 known member of this class. Found in three plant pathogen (satellite RNAs of the tobacco ringspot virus, arabis mosaic virus and chicory yellow mottle virus) which uses RNA as the infectious agent (FIG. 3).
Hepatitis Delta Virus (HDV) Ribozyme Size: 50–60 nucleotides (at present).
Cleavage of target RNAs recently demonstrated.
Sequence requirements not fully determined.
Binding sites and structural requirements not fully determined, although no sequences 5' of cleavage site are required.
Only 1 known member of this class. Found in human HDV (FIG. 4)
Neurospora VS RNA Ribozyme Size: ~144 nucleotides (at present)
Cleavage of target RNAs recently demonstrated.
Sequence requirements not fully determined.
Binding sites and structural requirements not fully determined.
Only 1 known member of this class. Found in Neurospora VS RNA (FIG. 5).

TABLE II

| Human IL-5 HH Target Sequence | | | | | |
|---|---|---|---|---|---|
| nt. | HH Target Sequence | Seq. ID No. | nt. | HH Target Sequence | Seq. ID No. |
| 8 | AUGCACU U UCUUUGC | 7 | 245 | AAGAAU CUUUCAGG | 47 |
| 9 | UGCACUU U CUUUGCC | 8 | 247 | GAAAUCU U UCAGGGA | 48 |
| 10 | GCACUUU CUUUGCCA | 9 | 248 | AAAUCUU U CAGGGAA | 49 |

TABLE II-continued

Human IL-5 HH Target Sequence

| nt. | HH Target Sequence | Seq. ID No. | nt. | HH Target Sequence | Seq. ID No. |
|---|---|---|---|---|---|
| 12 | ACUUUCU U UGCCAAA | 10 | 249 | AAUCUUU CAGGGAAU | 50 |
| 13 | CUUUCUU U GCCAAAG | 11 | 257 | AGGGAAU A GGCACAC | 51 |
| 36 | AGAACGU U UCAGAGC | 12 | 273 | GGAGAGU CAAACUGU | 52 |
| 37 | GAACGUU U CAGAGCC | 13 | 291 | AGGGGGU A CUGUGGA | 53 |
| 38 | AACGUUU CAGAGCCA | 14 | 305 | AAAGACU A UUCAAAA | 54 |
| 56 | GGAUGCU U CUGCAUU | 15 | 307 | AGACUAU U CAAAAAC | 55 |
| 57 | GAUGCUU CUGCAUUU | 16 | 308 | GACUAUU CAAAAACU | 56 |
| 63 | UCUGCAU U UGAGUUU | 17 | 316 | AAAAACU U GUCCUUA | 57 |
| 64 | CUGCAUU U GAGUUUG | 18 | 319 | AACUUGU CCUUAAUA | 58 |
| 69 | UUUGAGU U UGCUAGC | 19 | 322 | UUGUCCU U AAUAAAG | 59 |
| 70 | UUGAGUU U GCUAGCU | 20 | 323 | UGUCCUU A AUAAAGA | 60 |
| 74 | GUUUGCU A GCUCUUG | 21 | 326 | CCUUAAU A AAGAAAU | 61 |
| 78 | GCUAGCU CUUGGAGC | 22 | 334 | AAGAAAU A CAUUGAC | 62 |
| 80 | UAGCUCU U GGAGCUG | 23 | 338 | AAUACAU U GACGGCC | 63 |
| 91 | GCUGCCU A CGUGUAU | 24 | 380 | GGAGAGU A AACCAAU | 64 |
| 97 | UACGUGU A UGCCAUC | 25 | 388 | AACCAAU U CCUAGAC | 65 |
| 104 | AUGCCAU CCCCACAG | 26 | 389 | ACCAAUU CCUAGACU | 66 |
| 116 | CAGAAAU U CCCACAA | 27 | 392 | AAUUCCU A GACUACC | 67 |
| 117 | AGAAAUU CCCACAAG | 28 | 397 | CUAGACU A CCUGCAA | 68 |
| 130 | AGUGCAU U GGUGAAA | 29 | 409 | CAAGAGU U UCUUGGU | 69 |
| 145 | GAGACCU U GGCACUG | 30 | 410 | AAGAGUU U CUUGGUG | 70 |
| 155 | CACUGCU U UCUACUC | 31 | 411 | AGAGUUU CUUGGUGU | 71 |
| 156 | ACUGCUU U CUACUCA | 32 | 413 | AGUUUCU U GGUGUAA | 72 |
| 157 | CUGCUUU CUACUCAU | 33 | 419 | UUGGUGU A AUGAACA | 73 |
| 159 | GCUUUCU A CUCAUCG | 34 | 437 | AGUGGAU A AUAGAAA | 74 |
| 162 | UUCUACU CAUCGAAC | 35 | 440 | GGAUAAU A GAAAGUU | 75 |
| 165 | UACUCAU CGAACUCU | 36 | 447 | AGAAAGU U GAGACUA | 76 |
| 171 | UCGAACU CUGCUGAU | 37 | 454 | UGAGACU A AACUGGU | 77 |
| 179 | UGCUGAU A GCCAAUG | 38 | 462 | AACUGGU U UGUUGCA | 78 |
| 192 | UGAGACU CUGAGGAU | 39 | 463 | ACUGGUU U GUUGCAG | 79 |
| 200 | UGAGGAU U CCUGUUC | 40 | 466 | GGUUUGU U GCAGCCA | 80 |
| 201 | GAGGAUU CCUGUUCC | 41 | 479 | CAAAGAU U UUGGAGG | 81 |
| 206 | UUCCUGU U CCUGUAC | 42 | 480 | AAAGAUU U UGGAGGA | 82 |
| 207 | UCCUGUU CCUGUACA | 43 | 481 | AAGAUUU U GGAGGAG | 83 |
| 212 | UUCCUGU A CAUAAAA | 44 | 497 | AGGACAU U UUACUGC | 84 |
| 216 | UGUACAU A AAAAUCA | 45 | 498 | GGACAUU U UACUGCA | 85 |
| 222 | UAAAAAU CACCAACU | 46 | 499 | GACAUUU U ACUGCAG | 86 |
| 500 | ACAUUUU A CUGCAGU | 87 | 684 | UACUUUU U UCUUAUU | 135 |
| 531 | AAAGAGU CAGGCCUU | 88 | 685 | ACUUUUU U CUUAUUU | 136 |
| 538 | CAGGCCU U AAUUUUC | 89 | 686 | CUUUUUU CUUAUUUA | 137 |
| 539 | AGGCCUU A AUUUUCA | 90 | 688 | UUUUUCU U AUUUAAC | 138 |
| 542 | CCUUAAU U UUCAAUA | 91 | 689 | UUUUCUU A UUUAACU | 139 |
| 544 | UUAAUUU U CAAUAUA | 93 | 692 | UCUUAUU U AACUUAA | 141 |
| 545 | UAAUUUU CAAUAUAA | 94 | 693 | CUUAUUU A ACUUAAC | 142 |
| 549 | UUUCAAU A UAAUUUA | 95 | 697 | UUUAACU U AACAUUC | 143 |
| 551 | UCAAUAU A AUUUAAC | 96 | 698 | UUAACUU A ACAUUCU | 144 |
| 554 | AUAUAAU U UAACUUC | 97 | 703 | UUAACAU U CUGUAAA | 145 |
| 555 | UAUAAUU U AACUUCA | 98 | 704 | UAACAUU CUGUAAAA | 146 |
| 556 | AUAAUUU A ACUUCAG | 99 | 708 | AUUCUGU A AAAUGUC | 147 |
| 560 | UUUAACU U CAGAGGG | 100 | 715 | AAAAUGU CUGUUAAC | 148 |
| 561 | UUAACUU CAGAGGGA | 101 | 719 | UGUCUGU U AACUUAA | 149 |
| 573 | GGAAAGU A AAUAUUU | 102 | 720 | GUCUGUU A ACUUAAU | 150 |
| 577 | AGUAAAU A UUUCAGG | 103 | 724 | GUUAACU U AAUAGUA | 151 |
| 579 | UAAAUAU U UCAGGCA | 104 | 725 | UUAACUU A AUAGUAU | 152 |
| 580 | AAAUAUU U CAGGCAU | 105 | 728 | ACUUAAU A GUAUUUA | 153 |
| 581 | AAUAUUU CAGGCAUA | 106 | 731 | UAAUAGU A UUUAUGA | 154 |
| 588 | CAGGCAU A CUGACAC | 107 | 733 | AUAGUAU U UAUGAAA | 155 |
| 597 | UGACACU U UGCCAGA | 108 | 734 | UAGUAUU U AUGAAAU | 156 |
| 598 | GACACUU U GCCAGAA | 109 | 735 | AGUAUUU A UGAAAUG | 157 |
| 611 | AAAGCAU A AAAUUCU | 110 | 745 | AAAUGGU U AAGAAUU | 158 |
| 616 | AUAAAAU U CUUAAAA | 111 | 746 | AAUGGUU A AGAAUUU | 159 |
| 617 | UAAAAUU CUUAAAAU | 112 | 752 | UAAGAAU U UGGUAAA | 160 |
| 619 | AAAUUCU U AAAAUAU | 113 | 753 | AAGAAUU U GGUAAAU | 161 |
| 620 | AAUUCUU A AAAUAUA | 114 | 757 | AUUUGGU A AAUUAGU | 162 |
| 625 | UUAAAAU A UAUUUCA | 115 | 761 | GGUAAAU U AGUAUUU | 163 |
| 627 | AAAAUAU A UUUCAGA | 116 | 762 | GUAAAUU A GUAUUUA | 164 |
| 629 | AAUAUAU U UCAGAUA | 117 | 765 | AAUUAGU A UUUAUUU | 165 |
| 630 | AUAUAUU U CAGAUAU | 118 | 767 | UUAGUAU U UAUUUAA | 166 |
| 631 | UAUAUUU CAGAUAUC | 119 | 768 | UAGUAUU U AUUUAAU | 167 |
| 636 | UUCAGUA A UCAGAAU | 120 | 769 | AGUAUUU A UUUAAUG | 168 |
| 638 | CAGAUAU CAGAAUCA | 121 | 771 | UAUUUAU U UAAUGUU | 169 |
| 644 | UCAGAAU CAUUGAAG | 122 | 772 | AUUUAUU U AAUGUUA | 170 |
| 647 | GAAUCAU U GAAGUAU | 123 | 773 | UUUAUUU A AUGUUAU | 171 |
| 653 | UUGAAGU A UUUCCU | 124 | 778 | UUAAUGU U AUGUUGU | 172 |

TABLE II-continued

Human IL-5 HH Target Sequence

| nt. | HH Target Sequence | Seq. ID No. | nt. | HH Target Sequence | Seq. ID No. |
|---|---|---|---|---|---|
| 655 | GAAGUAU U UUCCUCC | 125 | 779 | UAAUGUU A UGUUGUG | 173 |
| 656 | AAGUAUU U UCCUCCA | 126 | 783 | GUUAUGU U GUGUUCU | 174 |
| 657 | AGUAUUU U CCUCCAG | 127 | 788 | GUUGUGU U CUAAUAA | 175 |
| 658 | GUAUUUU CCUCCAGG | 128 | 789 | UUGUGUU CUAAUAAA | 176 |
| 661 | UUUUCCU CCAGGCAA | 129 | 791 | GUGUUCU A AUAAAAC | 177 |
| 672 | GCAAAAU U GAUAUAC | 130 | 794 | UUCUAAU A AAACAAA | 178 |
| 676 | AAUUGAU A UACUUUU | 131 | 805 | CAAAAAU A GACAACU | 179 |
| 678 | UUGAUAU A CUUUUUU | 132 | | | |
| 681 | AUCUACU U UUUUCUU | 133 | | | |
| 682 | UAUACUU U UUUCUUA | 134 | | | |

TABLE III

Human IL-5 HH Ribozyme Sequences

| nt. | HH Ribozyme Sequence | Seq. ID No. |
|---|---|---|
| 8 | GCAAAGA CUGAUGAGGCCGAAAGGCCGAA AGUGCAU | 180 |
| 9 | GGCAAAG CUGAUGAGGCCGAAAGGCCGAA AAGUGCA | 181 |
| 10 | UGGCAAA CUGAUGAGGCCGAAAGGCCGAA AAAGUGC | 182 |
| 12 | UUUGGCA CUGAUGAGGCCGAAAGGCCGAA AGAAAGU | 183 |
| 13 | CUUUGGC CUGAUGAGGCCGAAAGGCCGAA AAGAAAG | 184 |
| 36 | GCUCUGA CUGAUGAGGCCGAAAGGCCGAA ACGUUCU | 185 |
| 37 | GGCUCUG CUGAUGAGGCCGAAAGGCCGAA AACGUUC | 186 |
| 38 | UGGCUCU CUGAUGAGGCCGAAAGGCCGAA AAACGUU | 187 |
| 56 | AAUGCAG CUGAUGAGGCCGAAAGGCCGAA AGCAUCC | 188 |
| 57 | AAAUGCA CUGAUGAGGCCGAAAGGCCGAA AAGCAUC | 189 |
| 63 | AAACUCA CUGAUGAGGCCGAAAGGCCGAA AUGCAGA | 190 |
| 64 | CAAACUC CUGAUGAGGCCGAAAGGCCGAA AAUGCAG | 191 |
| 69 | GCUAGCA CUGAUGAGGCCGAAAGGCCGAA ACUCAAA | 192 |
| 70 | AGCUAGC CUGAUGAGGCCGAAAGGCCGAA AACUCAA | 193 |
| 74 | CAAGAGC CUGAUGAGGCCGAAAGGCCGAA AGCAAAC | 194 |
| 78 | GCUCCAA CUGAUGAGGCCGAAAGGCCGAA AGCUAGC | 195 |
| 80 | CAGCUCC CUGAUGAGGCCGAAAGGCCGAA AGAGCUA | 196 |
| 91 | AUACACG CUGAUGAGGCCGAAAGGCCGAA AGGCAGC | 197 |
| 97 | GAUGGCA CUGAUGAGGCCGAAAGGCCGAA ACACGUA | 198 |
| 104 | CUGUGGG CUGAUGAGGCCGAAAGGCCGAA AUGGCAU | 199 |
| 116 | UUGUGGG CUGAUGAGGCCGAAAGGCCGAA AUUUCUG | 200 |
| 117 | CUUGUGG CUGAUGAGGCCGAAAGGCCGAA AAUUUCU | 201 |
| 130 | UUUCACC CUGAUGAGGCCGAAAGGCCGAA AUGCACU | 202 |
| 145 | CAGUGCC CUGAUGAGGCCGAAAGGCCGAA AGGUCUC | 203 |
| 155 | GAGUAGA CUGAUGAGGCCGAAAGGCCGAA AGCAGUG | 204 |
| 156 | UGAGUAG CUGAUGAGGCCGAAAGGCCGAA AAGCAGU | 205 |
| 157 | AUGAGUA CUGAUGAGGCCGAAAGGCCGAA AAAGCAG | 206 |
| 159 | CGAUGAG CUGAUGAGGCCGAAAGGCCGAA AGAAAGC | 207 |
| 162 | GUUCGAU CUGAUGAGGCCGAAAGGCCGAA AGUAGAA | 208 |
| 165 | AGAGUUC CUGAUGAGGCCGAAAGGCCGAA AUGAGUA | 209 |
| 171 | AUCAGCA CUGAUGAGGCCGAAAGGCCGAA AGUUCGA | 210 |
| 179 | CAUUGGC CUGAUGAGGCCGAAAGGCCGAA AUCAGCA | 211 |
| 192 | AUCCUCA CUGAUGAGGCCGAAAGGCCGAA AGUCUCA | 212 |
| 200 | GAACAGG CUGAUGAGGCCGAAAGGCCGAA AUCCUCA | 213 |
| 201 | GGAACAG CUGAUGAGGCCGAAAGGCCGAA AAUCCUC | 214 |
| 206 | GUACAGG CUGAUGAGGCCGAAAGGCCGAA ACAGGAA | 215 |
| 207 | UGUACAG CUGAUGAGGCCGAAAGGCCGAA AACAGGA | 216 |
| 212 | UUUUAUG CUGAUGAGGCCGAAAGGCCGAA ACAGGAA | 217 |
| 216 | UGAUUUU CUGAUGAGGCCGAAAGGCCGAA AUGUACA | 218 |
| 222 | AGUUGGU CUGAUGAGGCCGAAAGGCCGAA AUUUUUA | 219 |
| 245 | CCUGAAA CUGAUGAGGCCGAAAGGCCGAA AUUUCUU | 220 |
| 247 | UCCCUGA CUGAUGAGGCCGAAAGGCCGAA AGAUUUC | 221 |
| 248 | UUCCCUG CUGAUGAGGCCGAAAGGCCGAA AAGAUUU | 222 |
| 249 | AUUCCCU CUGAUGAGGCCGAAAGGCCGAA AAAGAUU | 223 |
| 257 | GUGUGCC CUGAUGAGGCCGAAAGGCCGAA AUUCCCU | 224 |
| 273 | ACAGUUU CUGAUGAGGCCGAAAGGCCGAA ACUCUCC | 225 |
| 291 | UCCACAG CUGAUGAGGCCGAAAGGCCGAA ACCCCCU | 226 |
| 305 | UUUUGAA CUGAUGAGGCCGAAAGGCCGAA AGUCUUU | 227 |
| 307 | GUUUUUG CUGAUGAGGCCGAAAGGCCGAA AUAGUCU | 228 |
| 308 | AGUUUUU CUGAUGAGGCCGAAAGGCCGAA AAUAGUC | 229 |
| 316 | UAAGGAC CUGAUGAGGCCGAAAGGCCGAA AGUUUUU | 230 |
| 319 | UAUUAAG CUGAUGAGGCCGAAAGGCCGAA ACAAGUU | 231 |
| 322 | CUUUAUU CUGAUGAGGCCGAAAGGCCGAA AGGACAA | 232 |
| 323 | UCUUUAU CUGAUGAGGCCGAAAGGCCGAA AAGGACA | 233 |
| 326 | AUUUCUU CUGAUGAGGCCGAAAGGCCGAA AUUAAGG | 234 |

TABLE III-continued

Human IL-5 HH Ribozyme Sequences

| nt. | HH Ribozyme Sequence | Seq. ID No. |
|---|---|---|
| 334 | GUCAAUG CUGAUGAGGCCGAAAGGCCGAA AUUUCUU | 235 |
| 338 | GGCCGUC CUGAUGAGGCCGAAAGGCCGAA AUGUAUU | 236 |
| 380 | AUUGGUU CUGAUGAGGCCGAAAGGCCGAA ACUCUCC | 237 |
| 388 | GUCUAGG CUGAUGAGGCCGAAAGGCCGAA AUUGGUU | 238 |
| 389 | AGUCUAG CUGAUGAGGCCGAAAGGCCGAA AAUUGGU | 239 |
| 392 | GGUAGUC CUGAUGAGGCCGAAAGGCCGAA AGGAAUU | 240 |
| 397 | UUGCAGG CUGAUGAGGCCGAAAGGCCGAA AGUCUAG | 241 |
| 409 | ACCAAGA CUGAUGAGGCCGAAAGGCCGAA ACUCUUG | 242 |
| 410 | CACCAAG CUGAUGAGGCCGAAAGGCCGAA AACUCUU | 243 |
| 411 | ACACCAA CUGAUGAGGCCGAAAGGCCGAA AAACUCU | 244 |
| 413 | UUACACC CUGAUGAGGCCGAAAGGCCGAA AGAAACU | 245 |
| 419 | UGUUCAU CUGAUGAGGCCGAAAGGCCGAA ACACCAA | 246 |
| 437 | UUUCUAU CUGAUGAGGCCGAAAGGCCGAA AUCCACU | 247 |
| 440 | AACUUUC CUGAUGAGGCCGAAAGGCCGAA AUUAUCC | 248 |
| 447 | UAGUCUC CUGAUGAGGCCGAAAGGCCGAA ACUUUCU | 249 |
| 454 | ACCAGUU CUGAUGAGGCCGAAAGGCCGAA AGUCUCA | 250 |
| 462 | UGCAACA CUGAUGAGGCCGAAAGGCCGAA ACCAGUU | 251 |
| 463 | CUGCAAC CUGAUGAGGCCGAAAGGCCGAA AACCAGU | 252 |
| 466 | UGGCUGC CUGAUGAGGCCGAAAGGCCGAA ACAAACC | 253 |
| 479 | CCUCCAA CUGAUGAGGCCGAAAGGCCGAA AUCUUUG | 254 |
| 480 | UCCUCCA CUGAUGAGGCCGAAAGGCCGAA AAUCUUU | 255 |
| 481 | CUCCUCC CUGAUGAGGCCGAAAGGCCGAA AAAUCUU | 256 |
| 497 | GCAGUAA CUGAUGAGGCCGAAAGGCCGAA AUGUCCU | 257 |
| 498 | UGCAGUA CUGAUGAGGCCGAAAGGCCGAA AAUGUCC | 258 |
| 499 | CUGCAGU CUGAUGAGGCCGAAAGGCCGAA AAAUGUC | 259 |
| 500 | ACUGCAG CUGAUGAGGCCGAAAGGCCGAA AAAAUGU | 260 |
| 531 | AAGGCCU CUGAUGAGGCCGAAAGGCCGAA ACUCUUU | 261 |
| 538 | GAAAAUU CUGAUGAGGCCGAAAGGCCGAA AGGCCUG | 262 |
| 539 | UGAAAAU CUGAUGAGGCCGAAAGGCCGAA AAGGCCU | 263 |
| 542 | UAUUGAA CUGAUGAGGCCGAAAGGCCGAA AUUAAGG | 264 |
| 543 | AUAUUGA CUGAUGAGGCCGAAAGGCCGAA AAUUAAG | 265 |
| 544 | UAUAUUG CUGAUGAGGCCGAAAGGCCGAA AAAUUAA | 266 |
| 545 | UUAUAUU CUGAUGAGGCCGAAAGGCCGAA AAAAUUA | 267 |
| 549 | UAAAUUA CUGAUGAGGCCGAAAGGCCGAA AUUGAAA | 268 |
| 551 | GUUAAAU CUGAUGAGGCCGAAAGGCCGAA AUAUUGA | 269 |
| 554 | GAAGUUA CUGAUGAGGCCGAAAGGCCGAA AUUAUAU | 270 |
| 555 | UGAAGUU CUGAUGAGGCCGAAAGGCCGAA AAUUAUA | 271 |
| 556 | CUGAAGU CUGAUGAGGCCGAAAGGCCGAA AAAUUAU | 272 |
| 560 | CCCUCUG CUGAUGAGGCCGAAAGGCCGAA AGUUAAA | 273 |
| 561 | UCCCUCU CUGAUGAGGCCGAAAGGCCGAA AAGUUAA | 274 |
| 573 | AAAUAUU CUGAUGAGGCCGAAAGGCCGAA ACUUUCC | 275 |
| 577 | CCUGAAA CUGAUGAGGCCGAAAGGCCGAA AUUUACU | 276 |
| 579 | UGCCUGA CUGAUGAGGCCGAAAGGCCGAA AUAUUUA | 277 |
| 580 | AUGCCUG CUGAUGAGGCCGAAAGGCCGAA AAUAUUU | 278 |
| 581 | UAUGCCU CUGAUGAGGCCGAAAGGCCGAA AAAUAUU | 279 |
| 588 | GUGUCAG CUGAUGAGGCCGAAAGGCCGAA AUGCCUG | 280 |
| 597 | UCUGGCA CUGAUGAGGCCGAAAGGCCGAA AGUGUCA | 281 |
| 598 | UUCUGGC CUGAUGAGGCCGAAAGGCCGAA AAGUGUC | 282 |
| 611 | AGAAUUU CUGAUGAGGCCGAAAGGCCGAA AUGCUUU | 283 |
| 616 | UUUUAAG CUGAUGAGGCCGAAAGGCCGAA AUUUUAU | 284 |
| 617 | AUUUUAA CUGAUGAGGCCGAAAGGCCGAA AAUUUUA | 285 |
| 619 | AUAUUUU CUGAUGAGGCCGAAAGGCCGAA AGAAUUU | 286 |
| 620 | UAUAUUU CUGAUGAGGCCGAAAGGCCGAA AAGAAUU | 287 |
| 625 | UGAAAUA CUGAUGAGGCCGAAAGGCCGAA AUUUUAA | 288 |
| 627 | UCUGAAA CUGAUGAGGCCGAAAGGCCGAA AUAUUUU | 289 |
| 629 | UAUCUGA CUGAUGAGGCCGAAAGGCCGAA AUAUAUU | 290 |
| 630 | AUAUCUG CUGAUGAGGCCGAAAGGCCGAA AAUAUAU | 291 |
| 631 | GAUAUCU CUGAUGAGGCCGAAAGGCCGAA AAAUAUA | 292 |
| 636 | AUUCUGA CUGAUGAGGCCGAAAGGCCGAA AUCUGAA | 293 |
| 638 | UGAUUCU CUGAUGAGGCCGAAAGGCCGAA AUAUCUG | 294 |
| 644 | CUUCAAU CUGAUGAGGCCGAAAGGCCGAA AUUCUGA | 295 |
| 647 | AUACUUC CUGAUGAGGCCGAAAGGCCGAA AUGAUUC | 296 |
| 653 | AGGAAAA CUGAUGAGGCCGAAAGGCCGAA ACUUCAA | 297 |
| 655 | GGAGGAA CUGAUGAGGCCGAAAGGCCGAA AUACUUC | 298 |
| 656 | UGGAGGA CUGAUGAGGCCGAAAGGCCGAA AAUACUU | 299 |
| 657 | CUGGAGG CUGAUGAGGCCGAAAGGCCGAA AAAUACU | 300 |
| 658 | CCUGGAG CUGAUGAGGCCGAAAGGCCGAA AAAAUAC | 301 |
| 661 | UUGCCUG CUGAUGAGGCCGAAAGGCCGAA AGGAAAA | 302 |
| 672 | GUAUAUC CUGAUGAGGCCGAAAGGCCGAA AUUUUGC | 303 |
| 676 | AAAAGUA CUGAUGAGGCCGAAAGGCCGAA AUCAAUU | 304 |
| 678 | AAAAAAG CUGAUGAGGCCGAAAGGCCGAA AUAUCAA | 305 |
| 681 | AAGAAAA CUGAUGAGGCCGAAAGGCCGAA AGUAUAU | 306 |
| 682 | UAAGAAA CUGAUGAGGCCGAAAGGCCGAA AAGUAUA | 307 |
| 683 | AUAAGAA CUGAUGAGGCCGAAAGGCCGAA AAAGUAU | 308 |
| 684 | AAUAAGA CUGAUGAGGCCGAAAGGCCGAA AAAAGUA | 309 |

TABLE III-continued

Human IL-5 HH Ribozyme Sequences

| nt. | HH Ribozyme Sequence | Seq. ID No. |
|---|---|---|
| 685 | AAAUAAG CUGAUGAGGCCGAAAGGCCGAA AAAAAGU | 310 |
| 686 | UAAAUAA CUGAUGAGGCCGAAAGGCCGAA AAAAAAG | 311 |
| 688 | GUUAAAU CUGAUGAGGCCGAAAGGCCGAA AGAAAAA | 312 |
| 689 | AGUUAAA CUGAUGAGGCCGAAAGGCCGAA AAGAAAA | 313 |
| 691 | UAAGUUA CUGAUGAGGCCGAAAGGCCGAA AUAAGAA | 314 |
| 692 | UUAAGUU CUGAUGAGGCCGAAAGGCCGAA AAUAAGA | 315 |
| 693 | GUUAAGU CUGAUGAGGCCGAAAGGCCGAA AAAUAAG | 316 |
| 697 | GAAUGUU CUGAUGAGGCCGAAAGGCCGAA AGUUAAA | 317 |
| 698 | AGAAUGU CUGAUGAGGCCGAAAGGCCGAA AAGUUAA | 318 |
| 703 | UUUACAG CUGAUGAGGCCGAAAGGCCGAA AUGUUAA | 319 |
| 704 | UUUUACA CUGAUGAGGCCGAAAGGCCGAA AAUGUUA | 320 |
| 708 | GACAUUU CUGAUGAGGCCGAAAGGCCGAA ACAGAAU | 321 |
| 715 | GUUAACA CUGAUGAGGCCGAAAGGCCGAA ACAUUUU | 322 |
| 719 | UUAAGUU CUGAUGAGGCCGAAAGGCCGAA ACAGACA | 323 |
| 720 | AUUAAGU CUGAUGAGGCCGAAAGGCCGAA AACAGAC | 324 |
| 724 | UACUAUU CUGAUGAGGCCGAAAGGCCGAA AGUUAAC | 325 |
| 725 | AUACUAU CUGAUGAGGCCGAAAGGCCGAA AAGUUAA | 326 |
| 728 | UAAAUAC CUGAUGAGGCCGAAAGGCCGAA AUUAAGU | 327 |
| 731 | UCAUAAA CUGAUGAGGCCGAAAGGCCGAA ACUAUUA | 328 |
| 733 | UUUCAUA CUGAUGAGGCCGAAAGGCCGAA AUACUAU | 329 |
| 734 | AUUUCAU CUGAUGAGGCCGAAAGGCCGAA AAUACUA | 330 |
| 735 | CAUUUCA CUGAUGAGGCCGAAAGGCCGAA AAAUACU | 331 |
| 745 | AAUUCUU CUGAUGAGGCCGAAAGGCCGAA ACCAUUU | 332 |
| 746 | AAAUUCU CUGAUGAGGCCGAAAGGCCGAA AACCAUU | 333 |
| 752 | UUUACCA CUGAUGAGGCCGAAAGGCCGAA AUUCUUA | 334 |
| 753 | AUUUACC CUGAUGAGGCCGAAAGGCCGAA AAUUCUU | 335 |
| 757 | ACUAAUU CUGAUGAGGCCGAAAGGCCGAA ACCAAAU | 336 |
| 761 | AAAUACU CUGAUGAGGCCGAAAGGCCGAA AUUUACC | 337 |
| 762 | UAAAUAC CUGAUGAGGCCGAAAGGCCGAA AAUUUAC | 338 |
| 765 | AAAUAAA CUGAUGAGGCCGAAAGGCCGAA ACUAAUU | 339 |
| 767 | UUAAAUA CUGAUGAGGCCGAAAGGCCGAA AUACUAA | 340 |
| 768 | AUUAAAU CUGAUGAGGCCGAAAGGCCGAA AAUACUA | 341 |
| 769 | CAUUAAA CUGAUGAGGCCGAAAGGCCGAA AAAUACU | 342 |
| 771 | AACAUUA CUGAUGAGGCCGAAAGGCCGAA AUAAAUA | 343 |
| 772 | UAACAUU CUGAUGAGGCCGAAAGGCCGAA AAUAAAU | 344 |
| 773 | AUAACAU CUGAUGAGGCCGAAAGGCCGAA AAAUAAA | 345 |
| 778 | ACAACAU CUGAUGAGGCCGAAAGGCCGAA ACAUUAA | 346 |
| 779 | CACAACA CUGAUGAGGCCGAAAGGCCGAA AACAUUA | 347 |
| 783 | AGAACAC CUGAUGAGGCCGAAAGGCCGAA ACAUAAC | 348 |
| 788 | UUAUUAG CUGAUGAGGCCGAAAGGCCGAA ACACAAC | 349 |
| 789 | UUUAUUA CUGAUGAGGCCGAAAGGCCGAA AACACAA | 350 |
| 791 | GUUUUAU CUGAUGAGGCCGAAAGGCCGAA AGAACAC | 351 |
| 794 | UUUGUUU CUGAUGAGGCCGAAAGGCCGAA AUUAGAA | 352 |
| 805 | AGUUGUC CUGAUGAGGCCGAAAGGCCGAA AUUUUUG | 353 |

TABLE IV

Mouse IL-5 HH Ribozyme Target Sequence

| nt. | HH Target Sequence | | | Seq. ID No. | nt. | HH Target Sequence | | | Seq. ID No. |
|---|---|---|---|---|---|---|---|---|---|
| 8 | cGCuCUU | c | CUUUGCu | 354 | 253 | AGGGgcU | A | GaCAuAC | 393 |
| 11 | uCUUcCU | U | UGCugAA | 355 | 259 | UagACAU | a | CUGaAgA | 394 |
| 12 | CUUcCUU | U | GCugAAG | 356 | 269 | GaAGAaU | C | AAACUGU | 395 |
| 36 | GAAgacU | U | CAGAGuC | 357 | 269 | GaAGAaU | c | AAaCugU | 396 |
| 36 | GaAgAcU | u | cAgAGUc | 358 | 269 | GAAgaAU | c | aAAcUgU | 397 |
| 37 | AAgacUU | C | AGAGuCA | 359 | 287 | uGGGGGU | A | CUGUGGA | 398 |
| 43 | UcaGaGU | c | AUGAgaA | 360 | 301 | AAAugCU | A | UUCcAAA | 399 |
| 58 | GGAUGCU | U | CUGCAcU | 361 | 301 | AAAugCU | a | uUCCaaA | 400 |
| 59 | GAUGCUU | C | UGCAcUU | 362 | 303 | AUGCuAU | u | CCaAaAc | 401 |
| 59 | gAUGcUU | c | uGcAcUU | 363 | 303 | AugCUAU | U | CcAAAAC | 402 |
| 66 | CUGCAcU | U | GAGUgUu | 364 | 304 | ugCUAUU | C | cAAAACc | 403 |
| 82 | UgAcucU | c | aGcUGUG | 365 | 315 | AACuUGU | C | aUUAAUA | 404 |
| 91 | GcUgUGU | c | uggGCCA | 366 | 318 | cUGUCaU | U | AAUAAAG | 405 |
| 112 | ugGAgAU | U | CCCAugA | 367 | 319 | UGUCaUU | A | AUAAAGA | 406 |
| 113 | gGAgAUU | C | CCAugAG | 368 | 322 | CaUUAAU | A | AAGAAAU | 407 |
| 141 | GAGACCU | U | GaCACaG | 369 | 330 | AAGAAAU | A | CAUUGAC | 408 |
| 141 | GAgACcU | U | GaCAcAg | 370 | 334 | AAUACAU | U | GACcGCC | 409 |
| 158 | gUCcgCU | C | AcCGAgC | 371 | 334 | AAUaCaU | u | GACcgCC | 410 |
| 167 | cCGAgCU | C | UGuUGAc | 372 | 384 | AggCAgU | U | CCUgGAu | 411 |
| 196 | UGAGGcU | U | CCUGUcC | 373 | 385 | ggCAgUU | C | CUgGAUu | 412 |
| 197 | GAGGcUU | C | CUGUcCC | 374 | 393 | CUgGAuU | A | CCUGCAA | 413 |

TABLE IV-continued

Mouse IL-5 HH Ribozyme Target Sequence

| nt. | HH Target Sequence | | | Seq. ID No. | nt. | HH Target Sequence | | | Seq. ID No. |
|---|---|---|---|---|---|---|---|---|---|
| 197 | gAGGCuU | c | CUGuCcC | 375 | 405 | CAAGAGU | U | cCUUGGU | 414 |
| 202 | UUCCUGU | c | CCUacuC | 376 | 406 | AAGAGUU | c | CUUGGUG | 415 |
| 202 | UUCCUGU | c | CcUAcuc | 377 | 409 | AGUUcCU | U | GGUGUgA | 416 |
| 206 | UGUCccU | a | cuCaUAA | 378 | 481 | UcaCAAU | u | UAAgUUA | 417 |
| 212 | UACUCAU | a | aAAaUCa | 379 | 482 | cAcAAUU | U | AAgUUaA | 418 |
| 212 | UacuCAU | A | AAAAUCA | 380 | 483 | AcAAUUU | A | AgUUaAa | 419 |
| 218 | UaaAaaU | c | aCcAGCU | 381 | 483 | AcAAUuU | a | aGUUAAa | 420 |
| 218 | UAAAAAU | C | ACCAgCU | 382 | 495 | AAAUUgU | c | AAcAgAU | 421 |
| 218 | uAAAAAU | c | acCAgCU | 383 | 553 | GCUGuuU | c | CaUuUAU | 422 |
| 232 | uaUGCAU | U | GGaGAAA | 384 | 557 | UuUcCAU | U | UauaUUU | 423 |
| 241 | gAGAAAU | C | UUUCAGG | 385 | 564 | UUauAuU | u | aUgUCCU | 424 |
| 241 | gAgAaAU | c | UUucAGG | 386 | 564 | UUAuaUU | u | AugUcCU | 425 |
| 241 | gagAAAU | c | UUUCAGG | 387 | 565 | uaUAUUU | a | ugUCCuG | 426 |
| 241 | gAgAaAU | c | UUUCAGg | 388 | 565 | UAUAuUU | a | UgUCcUg | 427 |
| 243 | gaAAucU | U | UCAGgGg | 389 | 569 | UUuAUGU | c | cUGUaGU | 428 |
| 243 | GAAAUCU | U | UCAGGGg | 390 | 569 | uUUAUGU | c | cUGUagU | 429 |
| 244 | AAAUCUU | U | CAGGGgc | 391 | 613 | AAAGuGU | u | uaaCCUU | 430 |
| 245 | AAUCUUU | C | AGGGgcU | 392 | 614 | AAgUGuU | u | aACcUUU | 431 |
| 620 | UUAACcU | u | uUuGUAU | 432 | 1407 | cCAgUUU | A | CUcCAGg | 481 |
| 793 | caAGgCU | u | UGuGcAU | 433 | 1407 | ccAgUUU | a | CUCCAGG | 482 |
| 816 | CUGagUU | a | UACUCcc | 434 | 1410 | gUUUaCU | C | CAGGaAA | 483 |
| 818 | GAguUAU | a | cUCCcuC | 435 | 1434 | AUgCUUU | U | aUuUaAU | 484 |
| 825 | ACUcCcU | c | CccCUCA | 436 | 1434 | aUgcUuU | U | AUUUAAu | 485 |
| 825 | aCUccCU | c | CcCcUCa | 437 | 1434 | aUgcuUU | u | AuUUAAU | 486 |
| 839 | AuCcucU | U | cGUUGCA | 438 | 1435 | UgCUUUU | a | UuUaAUU | 487 |
| 840 | uCcucUU | c | GUUGCAu | 439 | 1435 | ugcUUUU | a | uUUAaUU | 488 |
| 863 | cAAgUAU | U | cCAGGCu | 440 | 1438 | UuUUAAU | U | AAuUcug | 489 |
| 864 | AAgUAUU | c | CAGGCug | 441 | 1438 | uUUUAUU | U | AAUucUg | 490 |
| 864 | AAGUAUU | c | caggCug | 442 | 1439 | UUUAUUU | A | AUucUgU | 491 |
| 913 | gAaCUCU | U | GGucCaG | 443 | 1443 | UUUaAuU | c | UGuaAGa | 492 |
| 917 | UcUuggU | c | CAGAuGG | 444 | 1447 | AUUCUGU | A | AgAUGUu | 493 |
| 957 | UUagcAU | c | CUUUcUc | 445 | 1458 | ugUUcaU | a | UUAUUUA | 494 |
| 960 | GCAuccU | u | UcUcCuA | 446 | 1458 | ugUUcAU | A | uUAUUUA | 495 |
| 960 | GcaUcCU | u | uCUCcUa | 447 | 1460 | UucAUAU | u | AUUUAug | 496 |
| 962 | AUcCuuU | c | UCcUaGC | 448 | 1461 | UcAUAuU | A | UUUAUGA | 497 |
| 975 | gcccCUU | u | AgAUAgA | 449 | 1463 | AUAuUAU | U | UAUGAug | 498 |
| 987 | aGaUGAU | A | cuuAAUG | 450 | 1475 | AuGgAUU | c | aGUAAgU | 499 |
| 990 | UGAuACU | u | AAugacU | 451 | 1479 | AUUcaGU | A | AgUUAaU | 500 |
| 1000 | UGACuCU | c | UugCuGA | 452 | 1483 | aGuAAGU | u | AAUAUUU | 501 |
| 1027 | CgggGCU | U | cCUgCUC | 453 | 1483 | aGUAAgU | U | AaUAUUU | 502 |
| 1034 | UCCUGcU | C | CUaUcuA | 454 | 1484 | GUAAgUU | A | aUAUUUA | 503 |
| 1037 | UgcUCcU | A | UcUAACU | 455 | 1487 | agUUAAU | a | UUuAuUA | 504 |
| 1039 | cUccuAU | c | UAACUUC | 456 | 1487 | AgUUAaU | A | UUUAUUa | 505 |
| 1039 | cUCcUAU | c | UAACUUc | 457 | 1489 | UUAAUaU | U | uAuUAcA | 506 |
| 1041 | CcUAUcU | A | ACUUcAa | 458 | 1489 | UUAAuAU | u | UAUUaCA | 507 |
| 1051 | UUcAAuU | U | AAuAccC | 459 | 1489 | UUAaUAU | U | UAUUacA | 508 |
| 1148 | uGAcUUU | u | cUuaUGU | 460 | 1490 | UAAUaUU | u | AuUAcAc | 509 |
| 1213 | GCUgGaU | u | UUGGAaa | 461 | 1490 | UAaUAUU | U | AUuAcAc | 510 |
| 1213 | gcUGGAU | u | uUgGAAA | 462 | 1490 | UAaUAUU | U | AUUacAc | 511 |
| 1214 | cugGAUU | U | UGGAaaA | 463 | 1491 | AAUAUUU | a | uuaCAcg | 512 |
| 1215 | ugGAUUU | U | GGAaaAG | 464 | 1491 | AAUAUuU | a | UuAcAcg | 513 |
| 1234 | gGGACAU | c | UccuUGC | 465 | 1491 | AaUAUUU | A | UuAcAcG | 514 |
| 1236 | GACAUcU | c | cuUGCAG | 466 | 1491 | AaUAUUU | A | UUacAcG | 515 |
| 1275 | ugGGCCU | U | AcUUcUC | 467 | 1494 | AUuUAUU | a | CAcgUAU | 516 |
| 1276 | gGGCCUU | A | cUUcUCc | 468 | 1502 | cACGUaU | A | UaauAUu | 517 |
| 1280 | CUUAcUU | c | UCcgUgU | 469 | 1502 | cAcgUAU | a | UAAUaUU | 518 |
| 1298 | UgAACUU | a | AGAaGcA | 470 | 1507 | AUAUAaU | a | UUcUaaU | 519 |
| 1310 | gcAAAGU | a | aAuACcA | 471 | 1509 | AUAAuAU | U | CUaAuAA | 520 |
| 1310 | GCAAAgU | a | aAUAcca | 472 | 1509 | aUaaUaU | U | CUAAUAA | 521 |
| 1310 | GcaAAgU | a | AAUAccA | 473 | 1510 | UAAuAUU | C | UaAuAAa | 522 |
| 1350 | AAAGCAU | A | AAAUggU | 474 | 1510 | UAAuAUU | C | UaauAAA | 523 |
| 1358 | AAAUGGU | U | ggGAugU | 475 | 1510 | UAAuAuU | c | UaaUAAA | 524 |
| 1370 | UgUuaUU | C | AGgUAUC | 476 | 1510 | UaaUaUU | C | UAAUAAA | 525 |
| 1375 | UUCAGgU | A | UCAGggU | 477 | 1512 | aUaUUCU | A | AUAAAgC | 526 |
| 1377 | CAGgUAU | C | AGggUCA | 478 | 1515 | UUCUAAU | A | AAgCAgA | 527 |
| 1383 | UCAGggU | C | AcUGgAG | 479 | | | | | |
| 1405 | cccCAgU | U | UACUcCA | 480 | | | | | |

TABLE V

Mouse IL-5 HH Ribozyme Sequence

| nt. | HH Ribozyme Sequence | Seq. ID No. |
|---|---|---|
| 8 | AGCAAAG CUGAUGAGGCCGAAAGGCCGAA AAGAGCG | 528 |
| 11 | UUCAGCA CUGAUGAGGCCGAAAGGCCGAA AGGAAGA | 529 |
| 12 | CUUCAGCCUGAUGAGGCCGAAAGGCCGAA AAGGAAG | 530 |
| 36 | GACUCUG CUGAUGAGGCCGAAAGGCCGAA AGUCUUC | 531 |
| 36 | GACUCUG CUGAUGAGGCCGAAAGGCCGAA AGUCUUC | 532 |
| 37 | UGACUCU CUGAUGAGGCCGAAAGGCCGAA AAGUCUU | 533 |
| 43 | UUCUCAU CUGAUGAGGCCGAAAGGCCGAA ACUCUGA | 534 |
| 58 | AGUGCAG CUGAUGAGGCCGAAAGGCCGAA AGCAUCC | 535 |
| 59 | AAGUGCA CUGAUGAGGCCGAAAGGCCGAA AAGCAUC | 536 |
| 59 | AAGUGCA CUGAUGAGGCCGAAAGGCCGAA AAGCAUC | 537 |
| 66 | AACACUCCUGAUGAGGCCGAAAGGCCGAA AGUGCAG | 538 |
| 82 | CACAGCU CUGAUGAGGCCGAAAGGCCGAA AGAGUCA | 539 |
| 91 | UGGCCCA CUGAUGAGGCCGAAAGGCCGAA ACACAGC | 540 |
| 112 | UCAUGGG CUGAUGAGGCCGAAAGGCCGAA AUCUCCA | 541 |
| 113 | CUCAUGG CUGAUGAGGCCGAAAGGCCGAA AAUCUCC | 542 |
| 141 | CUGUGUCCUGAUGAGGCCGAAAGGCCGAA AGGUCUC | 543 |
| 141 | CUGUGUCCUGAUGAGGCCGAAAGGCCGAA AGGUCUC | 544 |
| 158 | GCUCGGU CUGAUGAGGCCGAAAGGCCGAA AGCGGAC | 545 |
| 167 | GUCAACA CUGAUGAGGCCGAAAGGCCGAA AGCUCGG | 546 |
| 196 | GGACAGG CUGAUGAGGCCGAAAGGCCGAA AGCCUCA | 547 |
| 197 | GGGACAG CUGAUGAGGCCGAAAGGCCGAA AAGCCUC | 548 |
| 197 | GGGACAG CUGAUGAGGCCGAAAGGCCGAA AAGCCUC | 549 |
| 202 | GAGUAGG CUGAUGAGGCCGAAAGGCCGAA ACAGGAA | 550 |
| 202 | GAGUAGG CUGAUGAGGCCGAAAGGCCGAA ACAGGAA | 551 |
| 206 | UUAUGAG CUGAUGAGGCCGAAAGGCCGAA AGGGACA | 552 |
| 212 | UGAUUUU CUGAUGAGGCCGAAAGGCCGAA AUGAGUA | 553 |
| 212 | UGAUUUU CUGAUGAGGCCGAAAGGCCGAA AUGAGUA | 554 |
| 218 | AGCUGGU CUGAUGAGGCCGAAAGGCCGAA AUUUUUA | 555 |
| 218 | AGCUGGU CUGAUGAGGCCGAAAGGCCGAA AUUUUUA | 556 |
| 218 | AGCUGGU CUGAUGAGGCCGAAAGGCCGAA AUUUUUA | 557 |
| 232 | UUUCUCCCUGAUGAGGCCGAAAGGCCGAA AUGCAUA | 558 |
| 241 | CCUGAAA CUGAUGAGGCCGAAAGGCCGAA AUUUCUC | 559 |
| 241 | CCUGAAA CUGAUGAGGCCGAAAGGCCGAA AUUUCUC | 560 |
| 241 | CCUGAAA CUGAUGAGGCCGAAAGGCCGAA AUUUCUC | 561 |
| 241 | CCUGAAA CUGAUGAGGCCGAAAGGCCGAA AUUUCUC | 562 |
| 243 | CCCCUGA CUGAUGAGGCCGAAAGGCCGAA AGAUUUC | 563 |
| 243 | CCCCUGA CUGAUGAGGCCGAAAGGCCGAA AGAUUUC | 564 |
| 244 | GCCCCUG CUGAUGAGGCCGAAAGGCCGAA AAGAUUU | 565 |
| 245 | AGCCCCU CUGAUGAGGCCGAAAGGCCGAA AAAGAUU | 566 |
| 253 | GUAUGUCCUGAUGAGGCCGAAAGGCCGAA AGCCCCU | 567 |
| 259 | UCUUCAG CUGAUGAGGCCGAAAGGCCGAA AUGUCUA | 568 |
| 269 | ACAGUUU CUGAUGAGGCCGAAAGGCCGAA AUUCUUC | 569 |
| 269 | ACAGUUU CUGAUGAGGCCGAAAGGCCGAA AUUCUUC | 570 |
| 269 | ACAGUUU CUGAUGAGGCCGAAAGGCCGAA AUUCUUC | 571 |
| 287 | UCCACAG CUGAUGAGGCCGAAAGGCCGAA ACCCCCA | 572 |
| 301 | UUUGGAA CUGAUGAGGCCGAAAGGCCGAA AGCAUUU | 573 |
| 301 | UUUGGAA CUGAUGAGGCCGAAAGGCCGAA AGCAUUU | 574 |
| 303 | GUUUUGG CUGAUGAGGCCGAAAGGCCGAA AUAGCAU | 575 |
| 303 | GUUUUGG CUGAUGAGGCCGAAAGGCCGAA AUAGCAU | 576 |
| 304 | GGUUUUG CUGAUGAGGCCGAAAGGCCGAA AAUAGCA | 577 |
| 315 | UAUUAAU CUGAUGAGGCCGAAAGGCCGAA ACAGGUU | 578 |
| 318 | CUUUAUU CUGAUGAGGCCGAAAGGCCGAA AUGACAG | 579 |
| 319 | UCUUUAU CUGAUGAGGCCGAAAGGCCGAA AAUGACA | 580 |
| 322 | AUUUCUU CUGAUGAGGCCGAAAGGCCGAA AUUAAUG | 581 |
| 330 | GUCAAUG CUGAUGAGGCCGAAAGGCCGAA AUUUCUU | 582 |
| 334 | GGCGGUCCUGAUGAGGCCGAAAGGCCGAA AUGUAUU | 583 |
| 334 | GGCGGUCCUGAUGAGGCCGAAAGGCCGAA AUGUAUU | 584 |
| 384 | AUCCAGG CUGAUGAGGCCGAAAGGCCGAA ACUGCCU | 585 |
| 385 | AAUCCAG CUGAUGAGGCCGAAAGGCCGAA AACUGCC | 586 |
| 393 | UUGCAGG CUGAUGAGGCCGAAAGGCCGAA AUCCAG | 587 |
| 405 | ACCAAGG CUGAUGAGGCCGAAAGGCCGAA ACUCUUG | 588 |
| 406 | CACCAAG CUGAUGAGGCCGAAAGGCCGAA AACUCUU | 589 |
| 409 | UCACACCCUGAUGAGGCCGAAAGGCCGAA AGGAACU | 590 |
| 481 | UAACUUA CUGAUGAGGCCGAAAGGCCGAA AUUGUGA | 591 |
| 482 | UUAACUU CUGAUGAGGCCGAAAGGCCGAA AAUUGUG | 592 |
| 483 | UUUAACU CUGAUGAGGCCGAAAGGCCGAA AAAUUGU | 593 |
| 483 | UUUAACU CUGAUGAGGCCGAAAGGCCGAA AAAUUGU | 594 |
| 495 | AUCUGUU CUGAUGAGGCCGAAAGGCCGAA ACAAUUU | 595 |
| 553 | AUAAAUG CUGAUGAGGCCGAAAGGCCGAA AAACAGC | 596 |
| 557 | AAAUAUA CUGAUGAGGCCGAAAGGCCGAA AUGGAAA | 597 |
| 564 | AGGACAU CUGAUGAGGCCGAAAGGCCGAA AAUAUAA | 598 |
| 564 | AGGACAU CUGAUGAGGCCGAAAGGCCGAA AAUAUAA | 599 |
| 565 | CAGGACA CUGAUGAGGCCGAAAGGCCGAA AAAUAUA | 600 |
| 565 | CAGGACA CUGAUGAGGCCGAAAGGCCGAA AAAUAUA | 601 |
| 569 | ACUACAG CUGAUGAGGCCGAAAGGCCGAA ACAUAAA | 602 |

TABLE V-continued

Mouse IL-5 HH Ribozyme Sequence

| nt. | HH Ribozyme Sequence | Seq. ID No. |
|---|---|---|
| 569 | ACUACAG CUGAUGAGGCCGAAAGGCCGAA ACAUAAA | 603 |
| 613 | AAGGUUA CUGAUGAGGCCGAAAGGCCGAA ACACUUU | 604 |
| 614 | AAAGGUU CUGAUGAGGCCGAAAGGCCGAA AACACUU | 605 |
| 620 | AUACAAA CUGAUGAGGCCGAAAGGCCGAA AGGUUAA | 606 |
| 793 | AUGCACA CUGAUGAGGCCGAAAGGCCGAA AGCCUUG | 607 |
| 816 | GGGAGUA CUGAUGAGGCCGAAAGGCCGAA AACUCAG | 608 |
| 818 | GAGGGAG CUGAUGAGGCCGAAAGGCCGAA AUAACUC | 609 |
| 825 | UGAGGGG CUGAUGAGGCCGAAAGGCCGAA AGGGAGU | 610 |
| 825 | UGAGGGG CUGAUGAGGCCGAAAGGCCGAA AGGGAGU | 611 |
| 839 | UGCAACG CUGAUGAGGCCGAAAGGCCGAA AGAGGAU | 612 |
| 840 | AUGCAACCUGAUGAGGCCGAAAGGCCGAA AAGAGGA | 613 |
| 863 | AGCCUGG CUGAUGAGGCCGAAAGGCCGAA AUACUUG | 614 |
| 864 | CAGCCUG CUGAUGAGGCCGAAAGGCCGAA AAUACUU | 615 |
| 864 | CAGCCUG CUGAUGAGGCCGAAAGGCCGAA AAUACUU | 616 |
| 913 | CUGGACCCUGAUGAGGCCGAAAGGCCGAA AGAGUUC | 617 |
| 917 | CCAUCUG CUGAUGAGGCCGAAAGGCCGAA ACCAAGA | 618 |
| 957 | GAGAAAG CUGAUGAGGCCGAAAGGCCGAA AUGCUAA | 619 |
| 960 | UAGGAGA CUGAUGAGGCCGAAAGGCCGAA AGGAUGC | 620 |
| 960 | UAGGAGA CUGAUGAGGCCGAAAGGCCGAA AGGAUGC | 621 |
| 962 | GCUAGGA CUGAUGAGGCCGAAAGGCCGAA AAAGGAU | 622 |
| 975 | UCUAUCU CUGAUGAGGCCGAAAGGCCGAA AAGGGGC | 623 |
| 987 | CAUUAGG CUGUAGAGGCCGAAAGGCCGAA AUCAUCU | 624 |
| 990 | AGUCAUU CUGAUGAGGCCGAAAGGCCGAA AGUAUCA | 625 |
| 1000 | UCAGCAA CUGAUGAGGCCGAAAGGCCGAA AGAGUCA | 626 |
| 1027 | GAGCAGG CUGAUGAGGCCGAAAGGCCGAA AGCCCCG | 627 |
| 1034 | UAGAUAG CUGAUGAGGCCGAAAGGCCGAA AGCAGGA | 628 |
| 1037 | AGUUAGA CUGAUGAGGCCGAAAGGCCGAA AGGAGCA | 629 |
| 1039 | GAAGUUA CUGAUGAGGCCGAAAGGCCGAA AUAGGAG | 630 |
| 1039 | GAAGUUA CUGAUGAGGCCGAAAGGCCGAA AUAGGAG | 631 |
| 1041 | UUGAAGU CUGAUGAGGCCGAAAGGCCGAA AGAUAGG | 632 |
| 1051 | GGGUAUU CUGAUGAGGCCGAAAGGCCGAA AAUUGAA | 633 |
| 1148 | ACAUAAG CUGAUGAGGCCGAAAGGCCGAA AAAGUCA | 634 |
| 1213 | UUUCCAA CUGAUGAGGCCGAAAGGCCGAA AUCCAGC | 635 |
| 1213 | UUUCCAA CUGAUGAGGCCGAAAGGCCGAA AUCCAGC | 636 |
| 1214 | UUUUCCA CUGAUGAGGCCGAAAGGCCGAA AAUCCAG | 637 |
| 1215 | CUUUUCCCUGAUGAGGCCGAAAGGCCGAA AAAUCCA | 638 |
| 1234 | GCAAGGA CUGAUGAGGCCGAAAGGCCGAA AUGUCCC | 639 |
| 1236 | CUGCAAG CUGAUGAGGCCGAAAGGCCGAA AGAUGUC | 640 |
| 1275 | GAGAAGU CUGAUGAGGCCGAAAGGCCGAA AGGCCCA | 641 |
| 1276 | GGAGAAG CUGAUGAGGCCGAAAGGCCGAA AAGGCCC | 642 |
| 1280 | ACACGGA CUGAUGAGGCCGAAAGGCCGAA AAGUAAG | 643 |
| 1298 | UGCUUCU CUGAUGAGGCCGAAAGGCCGAA AAGUUCA | 644 |
| 1310 | UGGUAUU CUGAUGAGGCCGAAAGGCCGAA ACUUUGC | 645 |
| 1310 | UGGUAUU CUGAUGAGGCCGAAAGGCCGAA ACUUUGC | 646 |
| 1310 | UGGUAUU CUGAUGAGGCCGAAAGGCCGAA ACUUUGC | 647 |
| 1350 | ACCAUUU CUGAUGAGGCCGAAAGGCCGAA AUGCUUU | 648 |
| 1358 | ACAUCCCCUGAUGAGGCCGAAAGGCCGAA ACCAUUU | 649 |
| 1370 | GAUACCU CUGAUGAGGCCGAAAGGCCGAA AAUAACA | 650 |
| 1375 | ACCCUGA CUGAUGAGGCCGAAAGGCCGAA ACCUGAA | 651 |
| 1377 | UGACCCU CUGAUGAGGCCGAAAGGCCGAA AUACCUG | 652 |
| 1383 | CUCCAGU CUGAUGAGGCCGAAAGGCCGAA ACCCUGA | 653 |
| 1405 | UGGAGUA CUGAUGAGGCCGAAAGGCCGAA ACUGGGG | 654 |
| 1407 | CCUGGAG CUGAUGAGGCCGAAAGGCCGAA AAACUGG | 655 |
| 1407 | CCUGGAG CUGAUGAGGCCGAAAGGCCGAA AAACUGG | 656 |
| 1410 | UUUCCUG CUGAUGAGGCCGAAAGGCCGAA AGUAAAC | 657 |
| 1434 | AUUAAAU CUGAUGAGGCCGAAAGGCCGAA AAAGCAU | 658 |
| 1434 | AUUAAAU CUGAUGAGGCCGAAAGGCCGAA AAAGCAU | 659 |
| 1434 | AUUAAAU CUGAUGAGGCCGAAAGGCCGAA AAAGCAU | 660 |
| 1435 | AAUUAAA CUGAUGAGGCCGAAAGGCCGAA AAAAGCA | 661 |
| 1435 | AAUUAAA CUGAUGAGGCCGAAAGGCCGAA AAAAGCA | 662 |
| 1438 | CAGAAUU CUGAUGAGGCCGAAAGGCCGAA AAUAAAA | 663 |
| 1438 | CAGAAUU CUGAUGAGGCCGAAAGGCCGAA AAUAAAA | 664 |
| 1439 | ACAGAAU CUGAUGAGGCCGAAAGGCCGAA AAAUAAA | 665 |
| 1443 | UCUUACA CUGAUGAGGCCGAAAGGCCGAA AAUUAAA | 666 |
| 1447 | AACAUCU CUGAUGAGGCCGAAAGGCCGAA ACAGAAU | 667 |
| 1458 | UAAAUAA CUGAUGAGGCCGAAAGGCCGAA AUGAACA | 668 |
| 1458 | UAAAUAA CUGAUGAGGCCGAAAGGCCGAA AUGAACA | 669 |
| 1460 | CAUAAAU CUGAUGAGGCCGAAAGGCCGAA AUAUGAA | 670 |
| 1461 | UCAUAAA CUGAUGAGGCCGAAAGGCCGAA AAUAUGA | 671 |
| 1463 | CAUCAUA CUGAUGAGGCCGAAAGGCCGAA AUAAUAU | 672 |
| 1475 | ACUUACU CUGAUGAGGCCGAAAGGCCGAA AAUCCAU | 673 |
| 1479 | AUUAACU CUGAUGAGGCCGAAAGGCCGAA ACUGAAU | 674 |
| 1483 | AAAUAUU CUGAUGAGGCCGAAAGGCCGAA ACUUACU | 675 |
| 1483 | AAAUAUU CUGAUGAGGCCGAAAGGCCGAA ACUUACU | 676 |
| 1484 | UAAAUAU CUGAUGAGGCCGAAAGGCCGAA AACUUAC | 677 |

TABLE V-continued

Mouse IL-5 HH Ribozyme Sequence

| nt. | HH Ribozyme Sequence | Seq. ID No. |
|---|---|---|
| 1487 | UAAUAAA CUGAUGAGGCCGAAAGGCCGAA AUUAACU | 678 |
| 1487 | UAAUAAA CUGAUGAGGCCGAAAGGCCGAA AUUAACU | 679 |
| 1489 | UGUAAUA CUGAUGAGGCCGAAAGGCCGAA AUAUUAA | 680 |
| 1489 | UGUAAUA CUGAUGAGGCCGAAAGGCCGAA AUAUUAA | 681 |
| 1489 | UGUAAUA CUGAUGAGGCCGAAAGGCCGAA AUAUUAA | 682 |
| 1490 | GUGUAAU CUGAUGAGGCCGAAAGGCCGAA AAUAUUA | 683 |
| 1490 | GUGUAAU CUGAUGAGGCCGAAAGGCCGAA AAUAUUA | 684 |
| 1490 | GUGUAAU CUGAUGAGGCCGAAAGGCCGAA AAUAUUA | 685 |
| 1491 | CGUGUAA CUGAUGAGGCCGAAAGGCCGAA AAAUAUU | 686 |
| 1491 | CGUGUAA CUGAUGAGGCCGAAAGGCCGAA AAAUAUU | 687 |
| 1491 | CGUGUAA CUGAUGAGGCCGAAAGGCCGAA AAAUAUU | 688 |
| 1491 | CGUGUAA CUGAUGAGGCCGAAAGGCCGAA AAAUAUU | 689 |
| 1494 | AUACGUG CUGAUGAGGCCGAAAGGCCGAA AAUAAAU | 690 |
| 1502 | AAUAUUA CUGAUGAGGCCGAAAGGCCGAA AUACGUG | 691 |
| 1502 | AAUAUUA CUGAUGAGGCCGAAAGGCCGAA AUACGUG | 692 |
| 1507 | AUUAGAA CUGAUGAGGCCGAAAGGCCGAA AUUAUAU | 693 |
| 1509 | UUAUUAG CUGAUGAGGCCGAAAGGCCGAA AUAUUAU | 694 |
| 1509 | UUAUUAG CUGAUGAGGCCGAAAGGCCGAA AUAUUAU | 695 |
| 1510 | UUUAUUA CUGAUGAGGCCGAAAGGCCGAA AAUAUUA | 696 |
| 1510 | UUUAUUA CUGAUGAGGCCGAAAGGCCGAA AAUAUUA | 697 |
| 1510 | UUUAUUA CUGAUGAGGCCGAAAGGCCGAA AAUAUUA | 698 |
| 1510 | UUUAUUA CUGAUGAGGCCGAAAGGCCGAA AAUAUUA | 699 |
| 1512 | GCUUUAU CUGAUGAGGCCGAAAGGCCGAA AGAAUAU | 700 |
| 1515 | UCUGCUU CUGAUGAGGCCGAAAGGCCGAA AUUAGAA | 701 |

TABLE VI

Human IL-5 Hairpin Ribozyme Sequences

| nt. | Hairpin Ribozyme Sequence | Seq. ID No | Substrate | Seq. ID No. |
|---|---|---|---|---|
| 86 | UACACGUA AGAA GCUCCA ACCAGCGAAACACACGUUGUGGUACAUUACCUGGUA | 702 | UGGAGCU GCCUACGUGUA | 703 |
| 151 | GAGUAGAA AGAA GUGCCA ACCAGAGAAACACACGUUGUGGUACAUUACCUGGUA | 704 | UGGCACU GCU UUCUACUC | 705 |
| 172 | UGGCUAUCAGAA GAGUUCACCAGAGAAACACACGUUGUGGUACAUUACCUGGUA | 706 | GAACUCU GCU GAUAGCCA | 707 |
| 203 | UGUACAGG AGAA GGAAUCACCAGAGAAACACACGUUGUGGUACAUUACCUGGUA | 708 | GAUUCCU GUU CCUGUACA | 709 |

TABLE VII

Mouse IL-5 Hairpin Ribozyme Sequences

| nt. | Hairpin Ribozyme Sequence | Seq. ID No | Substrate | Seq. ID No. |
|---|---|---|---|---|
| 75 | AGCUGAGA AGGA GAACACACCAGAGAAACACACGUUGUGGUACAUUACCUGGUA | 710 | GUGUUCU GACUCUCAGCU | 711 |
| 83 | CCAGACACAGAA GAGAGU ACCAGAGAAACACACGUUGUGGUACAGGACCUGGUA | 712 | ACUCUCA GCU GUGUCUGG | 713 |
| 147 | GAGCGGACAGAA GUGUCA ACCAGAGAAACACACGUUGUGGUACAUUACCUGGUA | 714 | UGACACA GCU GUCCGCUC | 715 |
| 150 | GGUGAGCG AGAA GCUGUG ACCAGAGAAACACACGUUGUGGUACAUUACCUGGUA | 716 | CACAGCU GUCCGCUCACC | 717 |
| 154 | GCUCGGUG AGAA GACAGCACCAGAGAAACACACGUUGUGGUACAUUACCUGGUA | 718 | GCUGUCCGCU CACCGAGC | 719 |
| 168 | UGCUUGUCAGAA GAGCUCACCAGAGAAACACACGUUGUGGUACAUUACCUGGUA | 720 | GAGCUCU GUU GACAAGCA | 721 |
| 199 | UGAGUAGG AGAA GGAAGCACCAGAGAAACACACGUUGUGGUACAUUACCUGGUA | 722 | GCUUCCU GUCCCUACUCA | 723 |
| 274 | CCCCCACG AGAA GUUUGA ACCAGAGAAACACACGUUGUGGUACAUUACCUGGUA | 724 | UCAAACU GUCCGUGGGGG | 725 |
| 381 | AAUCCAGG AGAA GCCUCG ACCAGAGAAACACACGUUGUGGUACAUUACCUGGUA | 726 | CGAGGCA GUU CCUGGAUU | 727 |
| 454 | CACCAUGG AGAA GCUCAG ACCAGAGAAACACACGUUGUGGUACAUUACCUGGUA | 728 | CUGAGCU GCU CCAUGGUG | 729 |
| 499 | GUUUUGCAGAA GUUGACACCAGAGAAACACACGUUGUGGUACAUUACCUGGUA | 730 | GUCAACA GAU GCAAAAAC | 731 |
| 548 | UAAAUGGA AGAA GCAUAU ACCAGAGAAACACACGUUGUGGUACAUUACCUGGUA | 732 | AUAUGCU GUU UCCAUUUA | 733 |
| 701 | GCAGGAGG AGAA GAAAUU ACCAGAGAAACACACGUUGUGGUACAUUACCUGGUA | 734 | AAUUUCU GAU CCUCCUGC | 735 |
| 710 | GAAGAGGA AGAA GGAGGA ACCAGAGAAACACACGUUGUGGUACAUUACCUGGUA | 736 | UCCUCCU GCCUCCUCUUC | 737 |
| 870 | AGUUCAAA AGAA GCCUGG ACCAGAGAAACACACGUUGUGGUACAUUACCUGGUA | 738 | CCAGGCU GACUUUGAACU | 739 |
| 919 | CUGCGUCCAGAA GGACCA ACCAGAAACACACGUUGUGGUACAUUACCUGGUA | 740 | UGGUCCA GAU GGACGCAG | 741 |
| 1030 | UAGAUAGG AGAA GGAAGCACCAGAGAAACACACGUUGUGGUACAUUACCUGGUA | 742 | GCUUCCU GCU CCUAUCUA | 743 |
| 1170 | AUGGCACA AGGA GAUUCA ACCAGAGAAACACACGUUGUGGUACAUUACCUGGUA | 744 | UGAAUCA GACUGUGCCAU | 745 |
| 1205 | CAAAAUCCAGAA GCUCCA ACCAGAGAAACACACGUUGUGGUACAUUACCUGGUA | 746 | UGGAGCA GCU GGAUUUUG | 747 |
| 1402 | CUGGAGUA AGAA GGGGGA ACCAGAGAAACACACGUUGUGGUACAUUACCUGGUA | 748 | UCCCCCA GUU UACUCCAG | 749 |
| 1421 | AAGCAUACAGAA GUUUUU ACCAGAGAAACACACGUUGUGGUACAUUACCUGGUA | 750 | AAAAACA GAU GUA UGCUU | 751 |

We claim:

1. An enzymatic RNA molecule which specifically cleaves IL-5 mRNA.

2. The enzymatic RNA molecule of claim 1, wherein said enzymatic RNA molecule is in a hammerhead motif.

3. The enzymatic RNA molecule of claim 1, wherein said enzymatic RNA molecule is in a hairpin, hepatitis delta virus, group I intron, VS RNA or RNaseP RNA motif.

4. The enzymatic RNA molecule of claim 1, wherein said enzymatic RNA molecule comprises between 12 and 100 bases complementary to said mRNA.

5. The enzymatic RNA molecule of claim 1, wherein said enzymatic RNA molecule comprises between 14 and 24 bases complementary to said mRNA.

6. The enzymatic RNA molecule of claim 2, wherein said enzymatic RNA molecule specifically cleaves any of the sequences defined as SEQ. ID. NOs. 7–179.

7. The hairpin enzymatic RNA molecule of claim 3, wherein said enzymatic RNA molecule specifically cleaves any of the sequences defined as SEQ. ID. Nos. 703, 705, 707, 709, 711, 713, 715, 717, 719, 721, 723, 725, 727, 729, 731, 733, 735, 737, 739, 741, 743, 745, 747, 749, or 751.

8. The enzymatic RNA molecule of claim 2, wherein said enzymatic RNA molecule consists of the sequences shown as SEQ. ID. Nos 180–353 or 528–701.

9. A mammalian cell including an enzymatic RNA molecule of any of claims 1–8 in vitro.

10. The cell of claim 9, wherein said cell is a human cell.

11. An expression vector including a nucleic acid encoding an enzymatic RNA molecule or multiple enzymatic RNA molecules of any of claims 1–8 in a manner which allows expression of that enzymatic RNA molecule(s) within a mammalian cell in vitro.

12. A mammalian cell including the expression vector of claim 11 in vitro.

13. The cell of claim 12, wherein said cell is a human cell.

14. The enzymatic RNA molecule of claim 3, wherein said hairpin comprises any of the sequences shown as SEQ. ID. NOs 702, 704, 706, 708, 710, 712, 714, 716, 718, 720, 722, 724, 726, 728, 730, 732, 734, 736, 738, 740, 742, 744, 746, 748, or 750.

15. The enzymatic RNA molecule of claim 2, wherein said enzymatic RNA molecule comprises a stem II region, and wherein said stem II is greater than or equal to 2 base pairs long.

16. The enzymatic RNA molecule of claim 3, wherein said hairpin comprises a stem IV region, and wherein said stem IV is greater than or equal to 2 base pairs long.

17. The enzymatic RNA molecule of any of claims 1–8 and 14–16, wherein said enzymatic RNA molecule comprises at least one sugar modification.

18. The enzymatic RNA molecule of any of claims 1–8 and 14–16, wherein said enzymatic RNA molecule comprises at least one base modification.

19. The enzymatic RNA molecule of any of claims 1–8 and 14–16, wherein said enzymatic RNA molecule comprises at least one phosphate modification.

20. The enzymatic RNA molecule of any of claims 1–8 and 14–16, wherein said enzymatic RNA molecule comprises at least two sugar modifications, wherein one said modification is a 2'-O-methyl and the other said modification is a 2'-deoxy-2'-amino.

21. The enzymatic RNA molecule of any of claims 1–8 and 14–16, wherein said enzymatic RNA molecule comprises at least two sugar modifications, wherein one said modification is a 2'-O-methyl and the other said modification is a 2'-C-allyl.

22. The enzymatic RNA molecule of claim 19, wherein said phosphate modification is a phosphorothioate.

\* \* \* \* \*

UNITED STATES PATENT AND TRADEMARK OFFICE
CERTIFICATE OF CORRECTION

PATENT NO. : 5,616,488

DATED : April 1, 1997

INVENTOR(S) : Sean Sullivan, Kenneth G. Draper, James MCSwiggen, Dan T. Stinchcomb It is certified that error appears in the above-identified patent and that said Letters Patent is hereby corrected as shown below:

Column 13, Table II, between 42nd entry "542 ........." and 43rd entry "544 ....." insert:
-- 543   CUUAAUU U UCAAUAU   92   691   UUCUUAU U UAACUUA   140 --

Claim 8, Column 273, Line 48: After "consists" insert --essentially of any--

Signed and Sealed this

Eighth Day of December, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 751

( 2 ) INFORMATION FOR SEQ ID NO:1:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base. The letter "H"stands for A, U, or C.

( x i ) SEQUENCE DESCRIPTION: SEQ ID NO:1:

NNNNUHNNNN N                                                                                     11

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.

( x i ) SEQUENCE DESCRIPTION: SEQ ID NO:2:

NNNNNCUGAN GAGNNNNNNC GAAANNNN                                                                   28

( 2 ) INFORMATION FOR SEQ ID NO:3:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base. The leter "Y"stands for U or C. The letter "H"stands for A, U, or C.

( x i ) SEQUENCE DESCRIPTION: SEQ ID NO:3:

NNN Y NGH Y NN NNNN                                                                              14

( 2 ) INFORMATION FOR SEQ ID NO:4:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.

( x i ) SEQUENCE DESCRIPTION: SEQ ID NO:4:

NNNNNNGAA GNNNNNNNN NAAACANNNN NNNNNNACA UUACNNNNN                                                50

( 2 ) INFORMATION FOR SEQ ID NO:5:

( i ) SEQUENCE CHARACTERISTICS:

( A ) LENGTH: 85 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:5:

UGGCCGGCAU GGUCCCAGCC UCCUCGCUGG CGCCGGCUGG GCAACAUUCC GAGGGGACCG      60

UCCCCUCGGU AAUGGCGAAU GGGAC      85

( 2 ) INFORMATION FOR SEQ ID NO:6:

( i ) SEQUENCE CHARACTERISTICS:
            ( A ) LENGTH: 176 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:6:

GGGAAAGCUU GCGAAGGGCG UCGUCGCCCC GAGCGGUAGU AAGCAGGGAA CUCACCUCCA      60

AUUUCAGUAC UGAAAUUGUC GUAGCAGUUG ACUACUGUUA UGUGAUUGGU AGAGGCUAAG     120

UGACGGUAUU GGCGUAAGUC AGUAUUGCAG CACAGCACAA GCCCGCUUGC GAGAAU        176

( 2 ) INFORMATION FOR SEQ ID NO:7:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:7:

AUGCACUUUC UUUGC      15

( 2 ) INFORMATION FOR SEQ ID NO:8:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:8:

UGCACUUUCU UUGCC      15

( 2 ) INFORMATION FOR SEQ ID NO:9:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:9:

GCACUUUCUU UGCCA      15

( 2 ) INFORMATION FOR SEQ ID NO:10:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:10:

ACUUUCUUUG CCAAA      15

( 2 ) INFORMATION FOR SEQ ID NO:11:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

CUUUCUUUGC CAAAG     15

( 2 ) INFORMATION FOR SEQ ID NO:12:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

AGAACGUUUC AGAGC     15

( 2 ) INFORMATION FOR SEQ ID NO:13:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

GAACGUUUCA GAGCC     15

( 2 ) INFORMATION FOR SEQ ID NO:14:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

AACGUUUCAG AGCCA     15

( 2 ) INFORMATION FOR SEQ ID NO:15:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

GGAUGCUUCU GCAUU     15

( 2 ) INFORMATION FOR SEQ ID NO:16:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

GAUGCUUCUG CAUUU     15

( 2 ) INFORMATION FOR SEQ ID NO:17:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:17:

UCUGCAUUUG AGUUU 15

( 2 ) INFORMATION FOR SEQ ID NO:18:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:18:

CUGCAUUUGA GUUUG 15

( 2 ) INFORMATION FOR SEQ ID NO:19:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:19:

UUUGAGUUUG CUAGC 15

( 2 ) INFORMATION FOR SEQ ID NO:20:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:20:

UUGAGUUUGC UAGCU 15

( 2 ) INFORMATION FOR SEQ ID NO:21:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

GUUUGCUAGC UCUUG 15

( 2 ) INFORMATION FOR SEQ ID NO:22:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:22:

GCUAGCUCUU GGAGC 15

( 2 ) INFORMATION FOR SEQ ID NO:23:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:23:

UAGCUCUUGG AGCUG         15

(2) INFORMATION FOR SEQ ID NO:24:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:24:

GCUGCCUACG UGUAU         15

(2) INFORMATION FOR SEQ ID NO:25:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:25:

UACGUGUAUG CCAUC         15

(2) INFORMATION FOR SEQ ID NO:26:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:26:

AUGCCAUCCC CACAG         15

(2) INFORMATION FOR SEQ ID NO:27:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:27:

CAGAAAUUCC CACAA         15

(2) INFORMATION FOR SEQ ID NO:28:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:28:

AGAAAUUCCC ACAAG         15

(2) INFORMATION FOR SEQ ID NO:29:

(i) SEQUENCE CHARACTERISTICS:
(A) LENGTH: 15 base pairs
(B) TYPE: nucleic acid (C) STRANDEDNESS: single
      (D) TOPOLOGY: linear (xi) SEQUENCE DESCRIPTION: SEQ ID NO:29:

AGUGCAUUGG UGAAA                                                                15

(2) INFORMATION FOR SEQ ID NO:30:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:30:

GAGACCUUGG CACUG                                                                15

(2) INFORMATION FOR SEQ ID NO:31:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:31:

CACUGCUUUC UACUC                                                                15

(2) INFORMATION FOR SEQ ID NO:32:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:32:

ACUGCUUUCU ACUCA                                                                15

(2) INFORMATION FOR SEQ ID NO:33:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:33:

CUGCUUUCUA CUCAU                                                                15

(2) INFORMATION FOR SEQ ID NO:34:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:34:

GCUUUCUACU CAUCG                                                                15

(2) INFORMATION FOR SEQ ID NO:35:

(i) SEQUENCE CHARACTERISTICS:
      (A) LENGTH: 15 base pairs
      (B) TYPE: nucleic acid
      (C) STRANDEDNESS: single
      (D) TOPOLOGY: linear ( x i ) SEQUENCE DESCRIPTION: SEQ ID NO:35:

UUCUACUCAU CGAAC                                                                                        15

( 2 ) INFORMATION FOR SEQ ID NO:36:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:36:

UACUCAUCGA ACUCU                                                                                        15

( 2 ) INFORMATION FOR SEQ ID NO:37:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:37:

UCGAACUCUG CUGAU                                                                                        15

( 2 ) INFORMATION FOR SEQ ID NO:38:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:38:

UGCUGAUAGC CAAUG                                                                                        15

( 2 ) INFORMATION FOR SEQ ID NO:39:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:39:

UGAGACUCUG AGGAU                                                                                        15

( 2 ) INFORMATION FOR SEQ ID NO:40:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:40:

UGAGGAUUCC UGUUC                                                                                        15

( 2 ) INFORMATION FOR SEQ ID NO:41:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:41:

GAGGAUUCCU GUUCC                                                                          15

(2) INFORMATION FOR SEQ ID NO:42:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:42:

UUCCUGUUCC UGUAC                                                                          15

(2) INFORMATION FOR SEQ ID NO:43:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:43:

UCCUGUUCCU GUACA                                                                          15

(2) INFORMATION FOR SEQ ID NO:44:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:44:

UUCCUGUACA UAAAA                                                                          15

(2) INFORMATION FOR SEQ ID NO:45:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:45:

UGUACAUAAA AAUCA                                                                          15

(2) INFORMATION FOR SEQ ID NO:46:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:46:

UAAAAUCAC CAACU                                                                           15

(2) INFORMATION FOR SEQ ID NO:47:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:47:

AAGAAAUCUU UCAGG                                                                          15

( 2 ) INFORMATION FOR SEQ ID NO:48:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

GAAAUCUUUC AGGGA                                      15

( 2 ) INFORMATION FOR SEQ ID NO:49:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

AAAUCUUUCA GGGAA                                      15

( 2 ) INFORMATION FOR SEQ ID NO:50:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

AAUCUUUCAG GGAAU                                      15

( 2 ) INFORMATION FOR SEQ ID NO:51:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

AGGGAAUAGG CACAC                                      15

( 2 ) INFORMATION FOR SEQ ID NO:52:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

GGAGAGUCAA ACUGU                                      15

( 2 ) INFORMATION FOR SEQ ID NO:53:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

AGGGGGUACU GUGGA                                      15

( 2 ) INFORMATION FOR SEQ ID NO:54:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

AAAGACUAUU CAAAA 15

( 2 ) INFORMATION FOR SEQ ID NO:55:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

AGACUAUUCA AAAAC 15

( 2 ) INFORMATION FOR SEQ ID NO:56:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

GACUAUUCAA AAACU 15

( 2 ) INFORMATION FOR SEQ ID NO:57:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

AAAAACUUGU CCUUA 15

( 2 ) INFORMATION FOR SEQ ID NO:58:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:58:

AACUUGUCCU UAAUA 15

( 2 ) INFORMATION FOR SEQ ID NO:59:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:59:

UUGUCCUUAA UAAAG 15

( 2 ) INFORMATION FOR SEQ ID NO:60:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:60:

UGUCCUUAAU AAAGA           15

( 2 ) INFORMATION FOR SEQ ID NO:61:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:61:

CCUUAAUAAA GAAAU           15

( 2 ) INFORMATION FOR SEQ ID NO:62:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:62:

AAGAAAUACA UUGAC           15

( 2 ) INFORMATION FOR SEQ ID NO:63:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:63:

AAUACAUUGA CGGCC           15

( 2 ) INFORMATION FOR SEQ ID NO:64:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:64:

GGAGAGUAAA CCAAU           15

( 2 ) INFORMATION FOR SEQ ID NO:65:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:65:

AACCAAUUCC UAGAC           15

( 2 ) INFORMATION FOR SEQ ID NO:66:

( i ) SEQUENCE CHARACTERISTICS:
    ( A ) LENGTH: 15 base pairs ( B ) TYPE: nucleic acid
( C ) STRANDEDNESS: single
( D ) TOPOLOGY: linear ( x i ) SEQUENCE DESCRIPTION: SEQ ID NO:66:

ACCAAUUCCU AGACU 15

( 2 ) INFORMATION FOR SEQ ID NO:67:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:67:

AAUCCUAGA CUACC 15

( 2 ) INFORMATION FOR SEQ ID NO:68:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:68:

CUAGACUACC UGCAA 15

( 2 ) INFORMATION FOR SEQ ID NO:69:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:69:

CAAGAGUUUC UUGGU 15

( 2 ) INFORMATION FOR SEQ ID NO:70:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:70:

AAGAGUUUCU UGGUG 15

( 2 ) INFORMATION FOR SEQ ID NO:71:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:71:

AGAGUUUCUU GGUGU 15

( 2 ) INFORMATION FOR SEQ ID NO:72:

( i ) SEQUENCE CHARACTERISTICS:
( A ) LENGTH: 15 base pairs
( B ) TYPE: nucleic acid
( C ) STRANDEDNESS: single ( D ) TOPOLOGY: linear ( x i ) SEQUENCE DESCRIPTION: SEQ ID NO:72:

AGUUUCUUGG UGUAA                                                                                        15

( 2 ) INFORMATION FOR SEQ ID NO:73:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:73:

UUGGUGUAAU GAACA                                                                                        15

( 2 ) INFORMATION FOR SEQ ID NO:74:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:74:

AGUGGAUAAU AGAAA                                                                                        15

( 2 ) INFORMATION FOR SEQ ID NO:75:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:75:

GGAUAAUAGA AAGUU                                                                                        15

( 2 ) INFORMATION FOR SEQ ID NO:76:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:76:

AGAAAGUUGA GACUA                                                                                        15

( 2 ) INFORMATION FOR SEQ ID NO:77:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:77:

UGAGACUAAA CUGGU                                                                                        15

( 2 ) INFORMATION FOR SEQ ID NO:78:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:78:

AACUGGUUUG UUGCA 15

( 2 ) INFORMATION FOR SEQ ID NO:79:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:79:

ACUGGUUUGU UGCAG 15

( 2 ) INFORMATION FOR SEQ ID NO:80:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:80:

GGUUUGUUGC AGCCA 15

( 2 ) INFORMATION FOR SEQ ID NO:81:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:81:

CAAAGAUUUU GGAGG 15

( 2 ) INFORMATION FOR SEQ ID NO:82:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:82:

AAAGAUUUUG GAGGA 15

( 2 ) INFORMATION FOR SEQ ID NO:83:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:83:

AAGAUUUUGG AGGAG 15

( 2 ) INFORMATION FOR SEQ ID NO:84:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:84:

```
AGGACAUUUU ACUGC                                                          15
```

(2) INFORMATION FOR SEQ ID NO:85:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:85:

```
GGACAUUUUA CUGCA                                                          15
```

(2) INFORMATION FOR SEQ ID NO:86:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:86:

```
GACAUUUUAC UGCAG                                                          15
```

(2) INFORMATION FOR SEQ ID NO:87:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:87:

```
ACAUUUUACU GCAGU                                                          15
```

(2) INFORMATION FOR SEQ ID NO:88:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:88:

```
AAAGAGUCAG GCCUU                                                          15
```

(2) INFORMATION FOR SEQ ID NO:89:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:89:

```
CAGGCCUUAA UUUUC                                                          15
```

(2) INFORMATION FOR SEQ ID NO:90:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:90:

```
AGGCCUUAAU UUUCA                                                          15
```

( 2 ) INFORMATION FOR SEQ ID NO:91:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:91:

CCUUAUUUU CAAUA 15

( 2 ) INFORMATION FOR SEQ ID NO:92:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:92:

CUUAAUUUUC AAUAU 15

( 2 ) INFORMATION FOR SEQ ID NO:93:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:93:

UUAAUUUUCA AUAUA 15

( 2 ) INFORMATION FOR SEQ ID NO:94:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:94:

UAAUUUUCAA UAUAA 15

( 2 ) INFORMATION FOR SEQ ID NO:95:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:95:

UUUCAAUAUA AUUUA 15

( 2 ) INFORMATION FOR SEQ ID NO:96:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:96:

UCAAUAUAAU UUAAC 15

( 2 ) INFORMATION FOR SEQ ID NO:97:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:97:

AUAUAAUUUA ACUUC      15

( 2 ) INFORMATION FOR SEQ ID NO:98:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:98:

UAUAAUUUAA CUUCA      15

( 2 ) INFORMATION FOR SEQ ID NO:99:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:99:

AUAAUUUAAC UUCAG      15

( 2 ) INFORMATION FOR SEQ ID NO:100:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:100:

UUUAACUUCA GAGGG      15

( 2 ) INFORMATION FOR SEQ ID NO:101:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:101:

UUAACUUCAG AGGGA      15

( 2 ) INFORMATION FOR SEQ ID NO:102:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:102:

GGAAAGUAAA UAUUU      15

( 2 ) INFORMATION FOR SEQ ID NO:103:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:103:

AGUAAAUAUU UCAGG 15

(2) INFORMATION FOR SEQ ID NO:104:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:104:

UAAAUAUUUC AGGCA 15

(2) INFORMATION FOR SEQ ID NO:105:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:105:

AAAUAUUUCA GGCAU 15

(2) INFORMATION FOR SEQ ID NO:106:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:106:

AAUAUUUCAG GCAUA 15

(2) INFORMATION FOR SEQ ID NO:107:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:107:

CAGGCAUACU GACAC 15

(2) INFORMATION FOR SEQ ID NO:108:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:108:

UGACACUUUG CCAGA 15

(2) INFORMATION FOR SEQ ID NO:109:

(i) SEQUENCE CHARACTERISTICS:
(A) LENGTH: 15 base pairs
(B) TYPE: nucleic acid (C) STRANDEDNESS: single
(D) TOPOLOGY: linear (xi) SEQUENCE DESCRIPTION: SEQ ID NO:109:

GACACUUUGC CAGAA  15

(2) INFORMATION FOR SEQ ID NO:110:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:110:

AAAGCAUAAA AUUCU  15

(2) INFORMATION FOR SEQ ID NO:111:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:111:

AUAAAAUUCU UAAAA  15

(2) INFORMATION FOR SEQ ID NO:112:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:112:

UAAAAUUCUU AAAAU  15

(2) INFORMATION FOR SEQ ID NO:113:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:113:

AAAUUCUUAA AAUAU  15

(2) INFORMATION FOR SEQ ID NO:114:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:114:

AAUUCUUAAA AUAUA  15

(2) INFORMATION FOR SEQ ID NO:115:

(i) SEQUENCE CHARACTERISTICS:
(A) LENGTH: 15 base pairs
(B) TYPE: nucleic acid
(C) STRANDEDNESS: single
(D) TOPOLOGY: linear ( x i ) SEQUENCE DESCRIPTION: SEQ ID NO:115:

UUAAAAUAUA UUUCA 15

( 2 ) INFORMATION FOR SEQ ID NO:116:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:116:

AAAAUAUAUU UCAGA 15

( 2 ) INFORMATION FOR SEQ ID NO:117:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:117:

AAUAUAUUUC AGAUA 15

( 2 ) INFORMATION FOR SEQ ID NO:118:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:118:

AUAUAUUUCA GAUAU 15

( 2 ) INFORMATION FOR SEQ ID NO:119:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:119:

UAUAUUUCAG AUAUC 15

( 2 ) INFORMATION FOR SEQ ID NO:120:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:120:

UUCAGAUAUC AGAAU 15

( 2 ) INFORMATION FOR SEQ ID NO:121:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:121:

CAGAUAUCAG AAUCA 15

( 2 ) INFORMATION FOR SEQ ID NO:122:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:122:

UCAGAAUCAU UGAAG 15

( 2 ) INFORMATION FOR SEQ ID NO:123:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:123:

GAAUCAUUGA AGUAU 15

( 2 ) INFORMATION FOR SEQ ID NO:124:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:124:

UUGAAGUAUU UUCCU 15

( 2 ) INFORMATION FOR SEQ ID NO:125:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:125:

GAAGUAUUUU CCUCC 15

( 2 ) INFORMATION FOR SEQ ID NO:126:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:126:

AAGUAUUUUC CUCCA 15

( 2 ) INFORMATION FOR SEQ ID NO:127:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:127:

AGUAUUUUCC UCCAG 15

( 2 ) INFORMATION FOR SEQ ID NO:128:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:128:

GUAUUUUCCU CCAGG          15

( 2 ) INFORMATION FOR SEQ ID NO:129:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:129:

UUUUCCUCCA GGCAA          15

( 2 ) INFORMATION FOR SEQ ID NO:130:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:130:

GCAAAAUUGA UAUAC          15

( 2 ) INFORMATION FOR SEQ ID NO:131:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:131:

AAUUGAUAUA CUUUU          15

( 2 ) INFORMATION FOR SEQ ID NO:132:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:132:

UUGAUAUACU UUUUU          15

( 2 ) INFORMATION FOR SEQ ID NO:133:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:133:

AUAUACUUUU UUCUU          15

( 2 ) INFORMATION FOR SEQ ID NO:134:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:134:

UAUACUUUUU UCUUA       15

( 2 ) INFORMATION FOR SEQ ID NO:135:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:135:

UACUUUUUUC UUAUU       15

( 2 ) INFORMATION FOR SEQ ID NO:136:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:136:

ACUUUUUUCU UAUUU       15

( 2 ) INFORMATION FOR SEQ ID NO:137:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:137:

CUUUUUUCUU AUUUA       15

( 2 ) INFORMATION FOR SEQ ID NO:138:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:138:

UUUUCUUAU UUAAC       15

( 2 ) INFORMATION FOR SEQ ID NO:139:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:139:

UUUUCUUAUU UAACU       15

( 2 ) INFORMATION FOR SEQ ID NO:140:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:140:

UUCUUAUUUA ACUUA 15

( 2 ) INFORMATION FOR SEQ ID NO:141:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:141:

UCUUAUUUAA CUUAA 15

( 2 ) INFORMATION FOR SEQ ID NO:142:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:142:

CUUAUUUAAC UUAAC 15

( 2 ) INFORMATION FOR SEQ ID NO:143:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:143:

UUUAACUUAA CAUUC 15

( 2 ) INFORMATION FOR SEQ ID NO:144:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:144:

UUAACUUAAC AUUCU 15

( 2 ) INFORMATION FOR SEQ ID NO:145:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:145:

UUAACAUUCU GUAAA 15

( 2 ) INFORMATION FOR SEQ ID NO:146:

( i ) SEQUENCE CHARACTERISTICS:
        ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO:146:

UAACAUUCUG UAAAA 15

(2) INFORMATION FOR SEQ ID NO:147:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:147:

AUUCUGUAAA AUGUC 15

(2) INFORMATION FOR SEQ ID NO:148:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:148:

AAAAUGUCUG UUAAC 15

(2) INFORMATION FOR SEQ ID NO:149:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:149:

UGUCUGUUAA CUUAA 15

(2) INFORMATION FOR SEQ ID NO:150:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:150:

GUCUGUUAAC UUAAU 15

(2) INFORMATION FOR SEQ ID NO:151:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:151:

GUUAACUUAA UAGUA 15

(2) INFORMATION FOR SEQ ID NO:152:

(i) SEQUENCE CHARACTERISTICS:
(A) LENGTH: 15 base pairs
(B) TYPE: nucleic acid
(C) STRANDEDNESS: single (D) TOPOLOGY: linear (xi) SEQUENCE DESCRIPTION: SEQ ID NO:152:

UUAACUUAAU AGUAU                                                                                    15

(2) INFORMATION FOR SEQ ID NO:153:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:153:

ACUUAAUAGU AUUUA                                                                                    15

(2) INFORMATION FOR SEQ ID NO:154:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:154:

UAAUAGUAUU UAUGA                                                                                    15

(2) INFORMATION FOR SEQ ID NO:155:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:155:

AUAGUAUUUA UGAAA                                                                                    15

(2) INFORMATION FOR SEQ ID NO:156:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:156:

UAGUAUUUAU GAAAU                                                                                    15

(2) INFORMATION FOR SEQ ID NO:157:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:157:

AGUAUUUAUG AAAUG                                                                                    15

(2) INFORMATION FOR SEQ ID NO:158:

(i) SEQUENCE CHARACTERISTICS:
                (A) LENGTH: 15 base pairs
                (B) TYPE: nucleic acid
                (C) STRANDEDNESS: single
                (D) TOPOLOGY: linear ( x i ) SEQUENCE DESCRIPTION: SEQ ID NO:158:

AAAUGGUUAA GAAUU                                                                                15

( 2 ) INFORMATION FOR SEQ ID NO:159:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:159:

AAUGGUUAAG AAUUU                                                                                15

( 2 ) INFORMATION FOR SEQ ID NO:160:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:160:

UAAGAAUUUG GUAAA                                                                                15

( 2 ) INFORMATION FOR SEQ ID NO:161:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:161:

AAGAAUUUGG UAAAU                                                                                15

( 2 ) INFORMATION FOR SEQ ID NO:162:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:162:

AUUUGGUAAA UUAGU                                                                                15

( 2 ) INFORMATION FOR SEQ ID NO:163:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:163:

GGUAAAUUAG UAUUU                                                                                15

( 2 ) INFORMATION FOR SEQ ID NO:164:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:164:

GUAAAUUAGU AUUUA                                                                15

( 2 ) INFORMATION FOR SEQ ID NO:165:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:165:

AAUUAGUAUU UAUUU                                                                15

( 2 ) INFORMATION FOR SEQ ID NO:166:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:166:

UUAGUAUUUA UUUAA                                                                15

( 2 ) INFORMATION FOR SEQ ID NO:167:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:167:

UAGUAUUUAU UUAAU                                                                15

( 2 ) INFORMATION FOR SEQ ID NO:168:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:168:

AGUAUUUAUU UAAUG                                                                15

( 2 ) INFORMATION FOR SEQ ID NO:169:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:169:

UAUUUAUUUA AUGUU                                                                15

( 2 ) INFORMATION FOR SEQ ID NO:170:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:170:

AUUUAUUUAA UGUUA                                                                15

( 2 ) INFORMATION FOR SEQ ID NO:171:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:171:

UUUAUUUAAU GUUAU               15

( 2 ) INFORMATION FOR SEQ ID NO:172:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:172:

UUAAUGUUAU GUUGU               15

( 2 ) INFORMATION FOR SEQ ID NO:173:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:173:

UAAUGUUAUG UUGUG               15

( 2 ) INFORMATION FOR SEQ ID NO:174:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:174:

GUUAUGUUGU GUUCU               15

( 2 ) INFORMATION FOR SEQ ID NO:175:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:175:

GUUGUGUUCU AAUAA               15

( 2 ) INFORMATION FOR SEQ ID NO:176:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:176:

UUGUGUUCUA AUAAA               15

( 2 ) INFORMATION FOR SEQ ID NO:177:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:177:

GUGUUCUAAU AAAAC                                                                15

( 2 ) INFORMATION FOR SEQ ID NO:178:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:178:

UUCUAAUAAA ACAAA                                                                15

( 2 ) INFORMATION FOR SEQ ID NO:179:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:179:

CAAAAAUAGA CAACU                                                                15

( 2 ) INFORMATION FOR SEQ ID NO:180:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:180:

GCAAAGACUG AUGAGGCCGA AAGGCCGAAA GUGCAU                                         36

( 2 ) INFORMATION FOR SEQ ID NO:181:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:181:

GGCAAAGCUG AUGAGGCCGA AAGGCCGAAA AGUGCA                                         36

( 2 ) INFORMATION FOR SEQ ID NO:182:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:182:

UGGCAAACUG AUGAGGCCGA AAGGCCGAAA AAGUGC                                         36

( 2 ) INFORMATION FOR SEQ ID NO:183:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:183:

UUUGGCACUG AUGAGGCCGA AAGGCCGAAA GAAAGU  36

(2) INFORMATION FOR SEQ ID NO:184:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:184:

CUUUGGCCUG AUGAGGCCGA AAGGCCGAAA AGAAAG  36

(2) INFORMATION FOR SEQ ID NO:185:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:185:

GCUCUGACUG AUGAGGCCGA AAGGCCGAAA CGUUCU  36

(2) INFORMATION FOR SEQ ID NO:186:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:186:

GGCUCUGCUG AUGAGGCCGA AAGGCCGAAA ACGUUC  36

(2) INFORMATION FOR SEQ ID NO:187:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:187:

UGGCUCUCUG AUGAGGCCGA AAGGCCGAAA AACGUU  36

(2) INFORMATION FOR SEQ ID NO:188:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:188:

AAUGCAGCUG AUGAGGCCGA AAGGCCGAAA GCAUCC  36

(2) INFORMATION FOR SEQ ID NO:189:

(i) SEQUENCE CHARACTERISTICS:
(A) LENGTH: 36 base pairs
(B) TYPE: nucleic acid ( C ) STRANDEDNESS: single
( D ) TOPOLOGY: linear ( x i ) SEQUENCE DESCRIPTION: SEQ ID NO:189:

AAAUGCACUG AUGAGGCCGA AAGGCCGAAA AGCAUC                    36

( 2 ) INFORMATION FOR SEQ ID NO:190:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:190:

AAACUCACUG AUGAGGCCGA AAGGCCGAAA UGCAGA                    36

( 2 ) INFORMATION FOR SEQ ID NO:191:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:191:

CAAACUCCUG AUGAGGCCGA AAGGCCGAAA AUGCAG                    36

( 2 ) INFORMATION FOR SEQ ID NO:192:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:192:

GCUAGCACUG AUGAGGCCGA AAGGCCGAAA CUCAAA                    36

( 2 ) INFORMATION FOR SEQ ID NO:193:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:193:

AGCUAGCCUG AUGAGGCCGA AAGGCCGAAA ACUCAA                    36

( 2 ) INFORMATION FOR SEQ ID NO:194:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:194:

CAAGAGCCUG AUGAGGCCGA AAGGCCGAAA GCAAAC                    36

( 2 ) INFORMATION FOR SEQ ID NO:195:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:195:

GCUCCAACUG AUGAGGCCGA AAGGCCGAAA GCUAGC    36

( 2 ) INFORMATION FOR SEQ ID NO:196:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:196:

CAGCUCCCUG AUGAGGCCGA AAGGCCGAAA GAGCUA    36

( 2 ) INFORMATION FOR SEQ ID NO:197:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:197:

AUACACGCUG AUGAGGCCGA AAGGCCGAAA GGCAGC    36

( 2 ) INFORMATION FOR SEQ ID NO:198:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:198:

GAUGGCACUG AUGAGGCCGA AAGGCCGAAA CACGUA    36

( 2 ) INFORMATION FOR SEQ ID NO:199:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:199:

CUGUGGGCUG AUGAGGCCGA AAGGCCGAAA UGGCAU    36

( 2 ) INFORMATION FOR SEQ ID NO:200:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:200:

UUGUGGGCUG AUGAGGCCGA AAGGCCGAAA UUUCUG    36

( 2 ) INFORMATION FOR SEQ ID NO:201:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:201:

CUUGUGGCUG AUGAGGCCGA AAGGCCGAAA AUUUCU  36

( 2 ) INFORMATION FOR SEQ ID NO:202:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:202:

UUUCACCCUG AUGAGGCCGA AAGGCCGAAA UGCACU  36

( 2 ) INFORMATION FOR SEQ ID NO:203:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:203:

CAGUGCCCUG AUGAGGCCGA AAGGCCGAAA GGUCUC  36

( 2 ) INFORMATION FOR SEQ ID NO:204:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:204:

GAGUAGACUG AUGAGGCCGA AAGGCCGAAA GCAGUG  36

( 2 ) INFORMATION FOR SEQ ID NO:205:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:205:

UGAGUAGCUG AUGAGGCCGA AAGGCCGAAA AGCAGU  36

( 2 ) INFORMATION FOR SEQ ID NO:206:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:206:

AUGAGUACUG AUGAGGCCGA AAGGCCGAAA AAGCAG  36

( 2 ) INFORMATION FOR SEQ ID NO:207:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:207:

CGAUGAGCUG AUGAGGCCGA AAGGCCGAAA GAAAGC  36

( 2 ) INFORMATION FOR SEQ ID NO:208:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:208:

GUUCGAUCUG AUGAGGCCGA AAGGCCGAAA GUAGAA                          36

( 2 ) INFORMATION FOR SEQ ID NO:209:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:209:

AGAGUUCCUG AUGAGGCCGA AAGGCCGAAA UGAGUA                          36

( 2 ) INFORMATION FOR SEQ ID NO:210:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:210:

AUCAGCACUG AUGAGGCCGA AAGGCCGAAA GUUCGA                          36

( 2 ) INFORMATION FOR SEQ ID NO:211:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:211:

CAUUGGCCUG AUGAGGCCGA AAGGCCGAAA UCAGCA                          36

( 2 ) INFORMATION FOR SEQ ID NO:212:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:212:

AUCCUCACUG AUGAGGCCGA AAGGCCGAAA GUCUCA                          36

( 2 ) INFORMATION FOR SEQ ID NO:213:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:213:

GAACAGGCUG AUGAGGCCGA AAGGCCGAAA UCCUCA                          36

( 2 ) INFORMATION FOR SEQ ID NO:214:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:214:

GGAACAGCUG AUGAGGCCGA AAGGCCGAAA AUCCUC         36

( 2 ) INFORMATION FOR SEQ ID NO:215:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:215:

GUACAGGCUG AUGAGGCCGA AAGGCCGAAA CAGGAA         36

( 2 ) INFORMATION FOR SEQ ID NO:216:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:216:

UGUACAGCUG AUGAGGCCGA AAGGCCGAAA ACAGGA         36

( 2 ) INFORMATION FOR SEQ ID NO:217:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:217:

UUUUAUGCUG AUGAGGCCGA AAGGCCGAAA CAGGAA         36

( 2 ) INFORMATION FOR SEQ ID NO:218:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:218:

UGAUUUCUG AUGAGGCCGA AAGGCCGAAA UGUACA         36

( 2 ) INFORMATION FOR SEQ ID NO:219:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:219:

AGUUGGUCUG AUGAGGCCGA AAGGCCGAAA UUUUUA         36

( 2 ) INFORMATION FOR SEQ ID NO:220:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:220:

CCUGAAACUG AUGAGGCCGA AAGGCCGAAA UUUCUU    36

( 2 ) INFORMATION FOR SEQ ID NO:221:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:221:

UCCCUGACUG AUGAGGCCGA AAGGCCGAAA GAUUUC    36

( 2 ) INFORMATION FOR SEQ ID NO:222:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:222:

UUCCCUGCUG AUGAGGCCGA AAGGCCGAAA AGAUUU    36

( 2 ) INFORMATION FOR SEQ ID NO:223:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:223:

AUUCCCUCUG AUGAGGCCGA AAGGCCGAAA AAGAUU    36

( 2 ) INFORMATION FOR SEQ ID NO:224:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:224:

GUGUGCCCUG AUGAGGCCGA AAGGCCGAAA UUCCCU    36

( 2 ) INFORMATION FOR SEQ ID NO:225:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:225:

ACAGUUUCUG AUGAGGCCGA AAGGCCGAAA CUCUCC    36

( 2 ) INFORMATION FOR SEQ ID NO:226:

( i ) SEQUENCE CHARACTERISTICS:
        ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO:226:

UCCACAGCUG AUGAGGCCGA AAGGCCGAAA CCCCCU    36

(2) INFORMATION FOR SEQ ID NO:227:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:227:

UUUUGAACUG AUGAGGCCGA AAGGCCGAAA GUCUUU    36

(2) INFORMATION FOR SEQ ID NO:228:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:228:

GUUUUUGCUG AUGAGGCCGA AAGGCCGAAA UAGUCU    36

(2) INFORMATION FOR SEQ ID NO:229:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:229:

AGUUUUUCUG AUGAGGCCGA AAGGCCGAAA AUAGUC    36

(2) INFORMATION FOR SEQ ID NO:230:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:230:

UAAGGACCUG AUGAGGCCGA AAGGCCGAAA GUUUUU    36

(2) INFORMATION FOR SEQ ID NO:231:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION:SEQ ID NO:231:

UAUUAAGCUG AUGAGGCCGA AAGGCCGAAA CAAGUU    3

(2) INFORMATION FOR SEQ ID NO:232:

(i) SEQUENCE CHARACTERISTICS:
(A) LENGTH: 36 base pairs
(B) TYPE: nucleic acid
(C) STRANDEDNESS: single ( D ) TOPOLOGY: linear ( x i ) SEQUENCE DESCRIPTION: SEQ ID NO:232:

CUUUAUUCUG AUGAGGCCGA AAGGCCGAAA GGACAA 36

( 2 ) INFORMATION FOR SEQ ID NO:233:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:233:

UCUUUAUCUG AUGAGGCCGA AAGGCCGAAA AGGACA 36

( 2 ) INFORMATION FOR SEQ ID NO:234:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:234:

AUUCUUCUG AUGAGGCCGA AAGGCCGAAA UUAAGG 36

( 2 ) INFORMATION FOR SEQ ID NO:235:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:235:

GUCAAUGCUG AUGAGGCCGA AAGGCCGAAA UUUCUU 36

( 2 ) INFORMATION FOR SEQ ID NO:236:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:236:

GGCCGUCCUG AUGAGGCCGA AAGGCCGAAA UGUAUU 36

( 2 ) INFORMATION FOR SEQ ID NO:237:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:237:

AUUGGUUCUG AUGAGGCCGA AAGGCCGAAA CUCUCC 36

( 2 ) INFORMATION FOR SEQ ID NO:238:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear (x i) SEQUENCE DESCRIPTION: SEQ ID NO:238:

GUCUAGGCUG AUGAGGCCGA AAGGCCGAAA UUGGUU    36

(2) INFORMATION FOR SEQ ID NO:239:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (x i) SEQUENCE DESCRIPTION: SEQ ID NO:239:

AGUCUAGCUG AUGAGGCCGA AAGGCCGAAA AUUGGU    36

(2) INFORMATION FOR SEQ ID NO:240:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (x i) SEQUENCE DESCRIPTION: SEQ ID NO:240:

GGUAGUCCUG AUGAGGCCGA AAGGCCGAAA GGAAUU    36

(2) INFORMATION FOR SEQ ID NO:241:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (x i) SEQUENCE DESCRIPTION: SEQ ID NO:241:

UUGCAGGCUG AUGAGGCCGA AAGGCCGAAA GUCUAG    36

(2) INFORMATION FOR SEQ ID NO:242:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (x i) SEQUENCE DESCRIPTION:SEQ ID NO:242:

ACCAAGACUG AUGAGGCCGA AAGGCCGAAA CUCUUG    3

(2) INFORMATION FOR SEQ ID NO:243:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (x i) SEQUENCE DESCRIPTION: SEQ ID NO:243:

CACCAAGCUG AUGAGGCCGA AAGGCCGAAA ACUCUU    36

(2) INFORMATION FOR SEQ ID NO:244:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (x i) SEQUENCE DESCRIPTION: SEQ ID NO:244:

ACACCAACUG AUGAGGCCGA AAGGCCGAAA AACUCU 36

(2) INFORMATION FOR SEQ ID NO:245:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO:245:

UUACACCCUG AUGAGGCCGA AAGGCCGAAA GAAACU 36

(2) INFORMATION FOR SEQ ID NO:246:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO:246:

UGUUCAUCUG AUGAGGCCGA AAGGCCGAAA CACCAA 36

(2) INFORMATION FOR SEQ ID NO:247:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO:247:

UUUCUAUCUG AUGAGGCCGA AAGGCCGAAA UCCACU 36

(2) INFORMATION FOR SEQ ID NO:248:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO:248:

AACUUUCCUG AUGAGGCCGA AAGGCCGAAA UUAUCC 36

(2) INFORMATION FOR SEQ ID NO:249:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO:249:

UAGUCUCCUG AUGAGGCCGA AAGGCCGAAA CUUUCU 36

(2) INFORMATION FOR SEQ ID NO:250:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO:250:

ACCAGUUCUG AUGAGGCCGA AAGGCCGAAA GUCUCA 36

( 2 ) INFORMATION FOR SEQ ID NO:251:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:251:

UGCAACACUG AUGAGGCCGA AAGGCCGAAA CCAGUU      36

( 2 ) INFORMATION FOR SEQ ID NO:252:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:252:

CUGCAACCUG AUGAGGCCGA AAGGCCGAAA ACCAGU      36

( 2 ) INFORMATION FOR SEQ ID NO:253:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:253:

UGGCUGCCUG AUGAGGCCGA AAGGCCGAAA CAAACC      3

( 2 ) INFORMATION FOR SEQ ID NO:254:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:254:

CCUCCAACUG AUGAGGCCGA AAGGCCGAAA UCUUUG      36

( 2 ) INFORMATION FOR SEQ ID NO:255:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:255:

UCCUCCACUG AUGAGGCCGA AAGGCCGAAA AUCUUU      36

( 2 ) INFORMATION FOR SEQ ID NO:256:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:256:

CUCCUCCCUG AUGAGGCCGA AAGGCCGAAA AAUCUU      36

( 2 ) INFORMATION FOR SEQ ID NO:257:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:257:

GCAGUAACUG AUGAGGCCGA AAGGCCGAAA UGUCCU    36

( 2 ) INFORMATION FOR SEQ ID NO:258:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:258:

UGCAGUACUG AUGAGGCCGA AAGGCCGAAA AUGUCC    36

( 2 ) INFORMATION FOR SEQ ID NO:259:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:259:

CUGCAGUCUG AUGAGGCCGA AAGGCCGAAA AAUGUC    36

( 2 ) INFORMATION FOR SEQ ID NO:260:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:260:

ACUGCAGCUG AUGAGGCCGA AAGGCCGAAA AAAUGU    36

( 2 ) INFORMATION FOR SEQ ID NO:261:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:261:

AAGGCCUCUG AUGAGGCCGA AAGGCCGAAA CUCUUU    36

( 2 ) INFORMATION FOR SEQ ID NO:262:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:262:

GAAAAUUCUG AUGAGGCCGA AAGGCCGAAA GGCCUG    36

( 2 ) INFORMATION FOR SEQ ID NO:263:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:263:

UGAAAAUCUG AUGAGGCCGA AAGGCCGAAA AGGCCU    36

(2) INFORMATION FOR SEQ ID NO:264:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION:SEQ ID NO:264:

UAUUGAACUG AUGAGGCCGA AAGGCCGAAA UUAAGG    3

(2) INFORMATION FOR SEQ ID NO:265:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:265:

AUAUUGACUG AUGAGGCCGA AAGGCCGAAA AUUAAG    36

(2) INFORMATION FOR SEQ ID NO:266:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:266:

UAUAUUGCUG AUGAGGCCGA AAGGCCGAAA AAUUAA    36

(2) INFORMATION FOR SEQ ID NO:267:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:267:

UUAUAUUCUG AUGAGGCCGA AAGGCCGAAA AAAUUA    36

(2) INFORMATION FOR SEQ ID NO:268:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:268:

UAAAUUACUG AUGAGGCCGA AAGGCCGAAA UUGAAA    36

(2) INFORMATION FOR SEQ ID NO:269:

(i) SEQUENCE CHARACTERISTICS:
(A) LENGTH: 36 base pairs
(B) TYPE: nucleic acid (C) STRANDEDNESS: single
(D) TOPOLOGY: linear (xi) SEQUENCE DESCRIPTION: SEQ ID NO:269:

GUUAAAUCUG AUGAGGCCGA AAGGCCGAAA UAUUGA        36

(2) INFORMATION FOR SEQ ID NO:270:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:270:

GAAGUUACUG AUGAGGCCGA AAGGCCGAAA UUAUAU        36

(2) INFORMATION FOR SEQ ID NO:271:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:271:

UGAAGUUCUG AUGAGGCCGA AAGGCCGAAA AUUAUA        36

(2) INFORMATION FOR SEQ ID NO:272:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:272:

CUGAAGUCUG AUGAGGCCGA AAGGCCGAAA AAUUAU        36

(2) INFORMATION FOR SEQ ID NO:273:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:273:

CCCUCUGCUG AUGAGGCCGA AAGGCCGAAA GUUAAA        36

(2) INFORMATION FOR SEQ ID NO:274:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:274:

UCCCUCUCUG AUGAGGCCGA AAGGCCGAAA AGUUAA        36

(2) INFORMATION FOR SEQ ID NO:275:

(i) SEQUENCE CHARACTERISTICS:
    (A) LENGTH: 36 base pairs
    (B) TYPE: nucleic acid
    (C) STRANDEDNESS: single
    (D) TOPOLOGY: linear ( x i ) SEQUENCE DESCRIPTION:SEQ ID NO:275:

AAAUAUUCUG AUGAGGCCGA AAGGCCGAAA CUUUCC  3

( 2 ) INFORMATION FOR SEQ ID NO:276:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:276:

CCUGAAACUG AUGAGGCCGA AAGGCCGAAA UUUACU  36

( 2 ) INFORMATION FOR SEQ ID NO:277:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:277:

UGCCUGACUG AUGAGGCCGA AAGGCCGAAA UAUUUA  36

( 2 ) INFORMATION FOR SEQ ID NO:278:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:278:

AUGCCUGCUG AUGAGGCCGA AAGGCCGAAA AUAUUU  36

( 2 ) INFORMATION FOR SEQ ID NO:279:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:279:

UAUGCCUCUG AUGAGGCCGA AAGGCCGAAA AAUAUU  36

( 2 ) INFORMATION FOR SEQ ID NO:280:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:280:

GUGUCAGCUG AUGAGGCCGA AAGGCCGAAA UGCCUG  36

( 2 ) INFORMATION FOR SEQ ID NO:281:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:281:

UCUGGCACUG AUGAGGCCGA AAGGCCGAAA GUGUCA 36

( 2 ) INFORMATION FOR SEQ ID NO:282:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:282:

UUCUGGCCUG AUGAGGCCGA AAGGCCGAAA AGUGUC 36

( 2 ) INFORMATION FOR SEQ ID NO:283:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:283:

AGAAUUUCUG AUGAGGCCGA AAGGCCGAAA UGCUUU 36

( 2 ) INFORMATION FOR SEQ ID NO:284:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:284:

UUUUAAGCUG AUGAGGCCGA AAGGCCGAAA UUUUAU 36

( 2 ) INFORMATION FOR SEQ ID NO:285:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:285:

AUUUUAACUG AUGAGGCCGA AAGGCCGAAA AUUUUA 36

( 2 ) INFORMATION FOR SEQ ID NO:286:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:286:

AUAUUUUCUG AUGAGGCCGA AAGGCCGAAA GAAUUU 3

( 2 ) INFORMATION FOR SEQ ID NO:287:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:287:

UAUAUUUCUG AUGAGGCCGA AAGGCCGAAA AGAAUU 36

( 2 ) INFORMATION FOR SEQ ID NO:288:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:288:

UGAAAUACUG AUGAGGCCGA AAGGCCGAAA UUUUAA     36

( 2 ) INFORMATION FOR SEQ ID NO:289:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:289:

UCUGAAACUG AUGAGGCCGA AAGGCCGAAA UAUUUU     36

( 2 ) INFORMATION FOR SEQ ID NO:290:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:290:

UAUCUGACUG AUGAGGCCGA AAGGCCGAAA UAUAUU     36

( 2 ) INFORMATION FOR SEQ ID NO:291:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:291:

AUAUCUGCUG AUGAGGCCGA AAGGCCGAAA AUAUAU     36

( 2 ) INFORMATION FOR SEQ ID NO:292:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:292:

GAUAUCUCUG AUGAGGCCGA AAGGCCGAAA AAUAUA     36

( 2 ) INFORMATION FOR SEQ ID NO:293:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:293:

AUUCUGACUG AUGAGGCCGA AAGGCCGAAA UCUGAA     36

( 2 ) INFORMATION FOR SEQ ID NO:294:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:294:

UGAUUCUCUG AUGAGGCCGA AAGGCCGAAA UAUCUG                        36

( 2 ) INFORMATION FOR SEQ ID NO:295:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:295:

CUUCAAUCUG AUGAGGCCGA AAGGCCGAAA UUCUGA                        36

( 2 ) INFORMATION FOR SEQ ID NO:296:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:296:

AUACUUCCUG AUGAGGCCGA AAGGCCGAAA UGAUUC                        36

( 2 ) INFORMATION FOR SEQ ID NO:297:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:297:

AGGAAAACUG AUGAGGCCGA AAGGCCGAAA CUUCAA                        3

( 2 ) INFORMATION FOR SEQ ID NO:298:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:298:

GGAGGAACUG AUGAGGCCGA AAGGCCGAAA UACUUC                        36

( 2 ) INFORMATION FOR SEQ ID NO:299:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:299:

UGGAGGACUG AUGAGGCCGA AAGGCCGAAA AUACUU                        36

( 2 ) INFORMATION FOR SEQ ID NO:300:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:300:

CUGGAGGCUG AUGAGGCCGA AAGGCCGAAA AAUACU      36

( 2 ) INFORMATION FOR SEQ ID NO:301:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:301:

CCUGGAGCUG AUGAGGCCGA AAGGCCGAAA AAAUAC      36

( 2 ) INFORMATION FOR SEQ ID NO:302:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:302:

UUGCCUGCUG AUGAGGCCGA AAGGCCGAAA GGAAAA      36

( 2 ) INFORMATION FOR SEQ ID NO:303:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:303:

GUAUAUCCUG AUGAGGCCGA AAGGCCGAAA UUUUGC      36

( 2 ) INFORMATION FOR SEQ ID NO:304:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:304:

AAAAGUACUG AUGAGGCCGA AAGGCCGAAA UCAAUU      36

( 2 ) INFORMATION FOR SEQ ID NO:305:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:305:

AAAAAAGCUG AUGAGGCCGA AAGGCCGAAA UAUCAA      36

( 2 ) INFORMATION FOR SEQ ID NO:306:

( i ) SEQUENCE CHARACTERISTICS:
        ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO:306:

AAGAAACUG AUGAGGCCGA AAGGCCGAAA GUAUAU    36

(2) INFORMATION FOR SEQ ID NO:307:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:307:

UAAGAAACUG AUGAGGCCGA AAGGCCGAAA AGUAUA    36

(2) INFORMATION FOR SEQ ID NO:308:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION:SEQ ID NO:308:

AUAAGAACUG AUGAGGCCGA AAGGCCGAAA AAGUAU    3

(2) INFORMATION FOR SEQ ID NO:309:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:309:

AAUAAGACUG AUGAGGCCGA AAGGCCGAAA AAAGUA    36

(2) INFORMATION FOR SEQ ID NO:310:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:310:

AAAUAAGCUG AUGAGGCCGA AAGGCCGAAA AAAAGU    36

(2) INFORMATION FOR SEQ ID NO:311:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:311:

UAAAUAACUG AUGAGGCCGA AAGGCCGAAA AAAAAG    36

(2) INFORMATION FOR SEQ ID NO:312:

(i) SEQUENCE CHARACTERISTICS:
(A) LENGTH: 36 base pairs
(B) TYPE: nucleic acid
(C) STRANDEDNESS: single (D) TOPOLOGY: linear (xi) SEQUENCE DESCRIPTION: SEQ ID NO:312:

GUUAAAUCUG AUGAGGCCGA AAGGCCGAAA GAAAAA 36

(2) INFORMATION FOR SEQ ID NO:313:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:313:

AGUUAAACUG AUGAGGCCGA AAGGCCGAAA AGAAAA 36

(2) INFORMATION FOR SEQ ID NO:314:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:314:

UAAGUUACUG AUGAGGCCGA AAGGCCGAAA UAAGAA 36

(2) INFORMATION FOR SEQ ID NO:315:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:315:

UUAAGUUCUG AUGAGGCCGA AAGGCCGAAA AUAAGA 36

(2) INFORMATION FOR SEQ ID NO:316:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:316:

GUUAAGUCUG AUGAGGCCGA AAGGCCGAAA AAUAAG 36

(2) INFORMATION FOR SEQ ID NO:317:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:317:

GAAUGUUCUG AUGAGGCCGA AAGGCCGAAA GUUAAA 36

(2) INFORMATION FOR SEQ ID NO:318:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO:318:

AGAAUGUCUG AUGAGGCCGA AAGGCCGAAA AGUUAA  36

( 2 ) INFORMATION FOR SEQ ID NO:319:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:319:

UUUACAGCUG AUGAGGCCGA AAGGCCGAAA UGUUAA  3

( 2 ) INFORMATION FOR SEQ ID NO:320:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:320:

UUUUACACUG AUGAGGCCGA AAGGCCGAAA AUGUUA  36

( 2 ) INFORMATION FOR SEQ ID NO:321:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:321:

GACAUUUCUG AUGAGGCCGA AAGGCCGAAA CAGAAU  36

( 2 ) INFORMATION FOR SEQ ID NO:322:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:322:

GUUAACACUG AUGAGGCCGA AAGGCCGAAA CAUUUU  36

( 2 ) INFORMATION FOR SEQ ID NO:323:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:323:

UUAAGUUCUG AUGAGGCCGA AAGGCCGAAA CAGACA  36

( 2 ) INFORMATION FOR SEQ ID NO:324:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:324:

AUUAAGUCUG AUGAGGCCGA AAGGCCGAAA ACAGAC 36

( 2 ) INFORMATION FOR SEQ ID NO:325:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:325:

UACUAUUCUG AUGAGGCCGA AAGGCCGAAA GUUAAC 36

( 2 ) INFORMATION FOR SEQ ID NO:326:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:326:

AUACUAUCUG AUGAGGCCGA AAGGCCGAAA AGUUAA 36

( 2 ) INFORMATION FOR SEQ ID NO:327:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:327:

UAAAUACCUG AUGAGGCCGA AAGGCCGAAA UUAAGU 36

( 2 ) INFORMATION FOR SEQ ID NO:328:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:328:

UCAUAAACUG AUGAGGCCGA AAGGCCGAAA CUAUUA 36

( 2 ) INFORMATION FOR SEQ ID NO:329:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:329:

UUUCAUACUG AUGAGGCCGA AAGGCCGAAA UACUAU 36

( 2 ) INFORMATION FOR SEQ ID NO:330:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:330:

AUUUCAUCUG AUGAGGCCGA AAGGCCGAAA AUACUA 3

( 2 ) INFORMATION FOR SEQ ID NO:331:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:331:

CAUUUCACUG AUGAGGCCGA AAGGCCGAAA AAUACU      36

( 2 ) INFORMATION FOR SEQ ID NO:332:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:332:

AAUUCUUCUG AUGAGGCCGA AAGGCCGAAA CCAUUU      36

( 2 ) INFORMATION FOR SEQ ID NO:333:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:333:

AAAUUCUCUG AUGAGGCCGA AAGGCCGAAA ACCAUU      36

( 2 ) INFORMATION FOR SEQ ID NO:334:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:334:

UUUACCACUG AUGAGGCCGA AAGGCCGAAA UUCUUA      36

( 2 ) INFORMATION FOR SEQ ID NO:335:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:335:

AUUUACCCUG AUGAGGCCGA AAGGCCGAAA AUUCUU      36

( 2 ) INFORMATION FOR SEQ ID NO:336:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:336:

ACUAAUUCUG AUGAGGCCGA AAGGCCGAAA CCAAAU      36

( 2 ) INFORMATION FOR SEQ ID NO:337:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:337:

AAAUACUCUG AUGAGGCCGA AAGGCCGAAA UUUACC     36

( 2 ) INFORMATION FOR SEQ ID NO:338:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:338:

UAAAUACCUG AUGAGGCCGA AAGGCCGAAA AUUUAC     36

( 2 ) INFORMATION FOR SEQ ID NO:339:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:339:

AAAUAAACUG AUGAGGCCGA AAGGCCGAAA CUAAUU     36

( 2 ) INFORMATION FOR SEQ ID NO:340:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:340:

UUAAAUACUG AUGAGGCCGA AAGGCCGAAA UACUAA     36

( 2 ) INFORMATION FOR SEQ ID NO:341:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION:SEQ ID NO:341:

AUUAAAUCUG AUGAGGCCGA AAGGCCGAAA AUACUA     3

( 2 ) INFORMATION FOR SEQ ID NO:342:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:342:

CAUUAAACUG AUGAGGCCGA AAGGCCGAAA AAUACU     36

( 2 ) INFORMATION FOR SEQ ID NO:343:

( i ) SEQUENCE CHARACTERISTICS:

( A ) LENGTH: 36 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:343:

AACAUUACUG AUGAGGCCGA AAGGCCGAAA UAAAUA 36

( 2 ) INFORMATION FOR SEQ ID NO:344:

( i ) SEQUENCE CHARACTERISTICS:
                    ( A ) LENGTH: 36 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:344:

UAACAUUCUG AUGAGGCCGA AAGGCCGAAA AUAAAU 36

( 2 ) INFORMATION FOR SEQ ID NO:345:

( i ) SEQUENCE CHARACTERISTICS:
                    ( A ) LENGTH: 36 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:345:

AUAACAUCUG AUGAGGCCGA AAGGCCGAAA AAUAAA 36

( 2 ) INFORMATION FOR SEQ ID NO:346:

( i ) SEQUENCE CHARACTERISTICS:
                    ( A ) LENGTH: 36 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:346:

ACAACAUCUG AUGAGGCCGA AAGGCCGAAA CAUUAA 36

( 2 ) INFORMATION FOR SEQ ID NO:347:

( i ) SEQUENCE CHARACTERISTICS:
                    ( A ) LENGTH: 36 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:347:

CACAACACUG AUGAGGCCGA AAGGCCGAAA ACAUUA 36

( 2 ) INFORMATION FOR SEQ ID NO:348:

( i ) SEQUENCE CHARACTERISTICS:
                    ( A ) LENGTH: 36 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:348:

AGAACACCUG AUGAGGCCGA AAGGCCGAAA CAUAAC 36

( 2 ) INFORMATION FOR SEQ ID NO:349:

( i ) SEQUENCE CHARACTERISTICS:
                    ( A ) LENGTH: 36 base pairs
                    ( B ) TYPE: nucleic acid (C) STRANDEDNESS: single
(D) TOPOLOGY: linear (xi) SEQUENCE DESCRIPTION: SEQ ID NO:349:

UUAUUAGCUG AUGAGGCCGA AAGGCCGAAA CACAAC                36

(2) INFORMATION FOR SEQ ID NO:350:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:350:

UUUAUUACUG AUGAGGCCGA AAGGCCGAAA ACACAA                36

(2) INFORMATION FOR SEQ ID NO:351:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:351:

GUUUUAUCUG AUGAGGCCGA AAGGCCGAAA GAACAC                36

(2) INFORMATION FOR SEQ ID NO:352:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:352:

UUUGUUUCUG AUGAGGCCGA AAGGCCGAAA UUAGAA                3

(2) INFORMATION FOR SEQ ID NO:353:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:353:

AGUUGUCCUG AUGAGGCCGA AAGGCCGAAA UUUUUG                36

(2) INFORMATION FOR SEQ ID NO:354:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO:354:

CGCUCUUCCU UUGCU                15

(2) INFORMATION FOR SEQ ID NO:355:

(i) SEQUENCE CHARACTERISTICS:
    (A) LENGTH: 15 base pairs
    (B) TYPE: nucleic acid
    (C) STRANDEDNESS: single
    (D) TOPOLOGY: linear ( x i ) SEQUENCE DESCRIPTION: SEQ ID NO:355:

UCUUCCUUUG CUGAA                                                                        15

( 2 ) INFORMATION FOR SEQ ID NO:356:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:356:

CUUCCUUUGC UGAAG                                                                        15

( 2 ) INFORMATION FOR SEQ ID NO:357:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:357:

GAAGACUUCA GAGUC                                                                        15

( 2 ) INFORMATION FOR SEQ ID NO:358:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:358:

GAAGACUUCA GAGUC                                                                        15

( 2 ) INFORMATION FOR SEQ ID NO:359:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:359:

AAGACUUCAG AGUCA                                                                        15

( 2 ) INFORMATION FOR SEQ ID NO:360:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:360:

UCAGAGUCAU GAGAA                                                                        15

( 2 ) INFORMATION FOR SEQ ID NO:361:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:361:

GGAUGCUUCU GCACU                                              15

( 2 ) INFORMATION FOR SEQ ID NO:362:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:362:

GAUGCUUCUG CACUU                                              15

( 2 ) INFORMATION FOR SEQ ID NO:363:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:363:
                GAUGCUUCUG CACUU ( 2 ) INFORMATION FOR SEQ ID NO:364:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:364:

CUGCACUUGA GUGUU                                              15

( 2 ) INFORMATION FOR SEQ ID NO:365:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:365:

UGACUCUCAG CUGUG                                              15

( 2 ) INFORMATION FOR SEQ ID NO:366:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:366:

GCUGUGUCUG GGCCA                                              15

( 2 ) INFORMATION FOR SEQ ID NO:367:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:367:

UGGAGAUUCC CAUGA                                              15

( 2 ) INFORMATION FOR SEQ ID NO:368:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:368:

GGAGAUUCCC AUGAG                                        15

( 2 ) INFORMATION FOR SEQ ID NO:369:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:369:

GAGACCUUGA CACAG                                        15

( 2 ) INFORMATION FOR SEQ ID NO:370:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:370:

GAGACCUUGA CACAG                                        15

( 2 ) INFORMATION FOR SEQ ID NO:371:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:371:

GUCCGCUCAC CGAGC                                        15

( 2 ) INFORMATION FOR SEQ ID NO:372:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:372:

CCGAGCUCUG UUGAC                                        15

( 2 ) INFORMATION FOR SEQ ID NO:373:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:373:

UGAGGCUUCC UGUCC                                        15

( 2 ) INFORMATION FOR SEQ ID NO:374:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION:SEQ ID NO:374:

GAGGCUUCCU GUCCC  1

( 2 ) INFORMATION FOR SEQ ID NO:375:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:375:

GAGGCUUCCU GUCCC  15

( 2 ) INFORMATION FOR SEQ ID NO:376:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:376:

UUCCUGUCCC UACUC  15

( 2 ) INFORMATION FOR SEQ ID NO:377:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:377:

UUCCUGUCCC UACUC  15

( 2 ) INFORMATION FOR SEQ ID NO:378:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:378:

UGUCCCUACU CAUAA  15

( 2 ) INFORMATION FOR SEQ ID NO:379:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:379:

UACUCAUAAA AAUCA  15

( 2 ) INFORMATION FOR SEQ ID NO:380:

( i ) SEQUENCE CHARACTERISTICS:
   ( A ) LENGTH: 15 base pairs ( B ) TYPE: nucleic acid
           ( C ) STRANDEDNESS: single
           ( D ) TOPOLOGY: linear ( x i ) SEQUENCE DESCRIPTION: SEQ ID NO:380:

UACUCAUAAA  AAUCA                                                                                        15

( 2 ) INFORMATION FOR SEQ ID NO:381:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:381:

UAAAAAUCAC  CAGCU                                                                                        15

( 2 ) INFORMATION FOR SEQ ID NO:382:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:382:

UAAAAAUCAC  CAGCU                                                                                        15

( 2 ) INFORMATION FOR SEQ ID NO:383:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:383:

UAAAAAUCAC  CAGCU                                                                                        15

( 2 ) INFORMATION FOR SEQ ID NO:384:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:384:

UAUGCAUUGG  AGAAA                                                                                        15

( 2 ) INFORMATION FOR SEQ ID NO:385:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( x i ) SEQUENCE DESCRIPTION:SEQ ID NO:385:

GAGAAAUCUU  UCAGG                                                                                         1

( 2 ) INFORMATION FOR SEQ ID NO:386:

( i ) SEQUENCE CHARACTERISTICS:
           ( A ) LENGTH: 15 base pairs
           ( B ) TYPE: nucleic acid
           ( C ) STRANDEDNESS: single ( D ) TOPOLOGY: linear ( x i ) SEQUENCE DESCRIPTION: SEQ ID NO:386:

GAGAAAUCUU UCAGG   15

( 2 ) INFORMATION FOR SEQ ID NO:387:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:387:

GAGAAAUCUU UCAGG   15

( 2 ) INFORMATION FOR SEQ ID NO:388:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:388:

GAGAAAUCUU UCAGG   15

( 2 ) INFORMATION FOR SEQ ID NO:389:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:389:

GAAAUCUUUC AGGGG   15

( 2 ) INFORMATION FOR SEQ ID NO:390:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:390:

GAAAUCUUUC AGGGG   15

( 2 ) INFORMATION FOR SEQ ID NO:391:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:391:

AAAUCUUUCA GGGGC   15

( 2 ) INFORMATION FOR SEQ ID NO:392:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:392:

AAUCUUUCAG GGGCU 15

( 2 ) INFORMATION FOR SEQ ID NO:393:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:393:

AGGGGCUAGA CAUAC 15

( 2 ) INFORMATION FOR SEQ ID NO:394:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:394:

UAGACAUACU GAAGA 15

( 2 ) INFORMATION FOR SEQ ID NO:395:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:395:

GAAGAAUCAA ACUGU 15

( 2 ) INFORMATION FOR SEQ ID NO:396:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:396:

GAAGAAUCAA ACUGU 1

( 2 ) INFORMATION FOR SEQ ID NO:397:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:397:

GAAGAAUCAA ACUGU 15

( 2 ) INFORMATION FOR SEQ ID NO:398:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:398:

UGGGGGUACU GUGGA 15

(2) INFORMATION FOR SEQ ID NO:399:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO:399:

AAAUGCUAUU CCAAA 15

(2) INFORMATION FOR SEQ ID NO:400:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO:400:

AAAUGCUAUU CCAAA 15

(2) INFORMATION FOR SEQ ID NO:401:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO:401:

AUGCUAUUCC AAAAC 15

(2) INFORMATION FOR SEQ ID NO:402:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO:402:

AUGCUAUUCC AAAAC 15

(2) INFORMATION FOR SEQ ID NO:403:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO:403:

UGCUAUUCCA AAACC 15

(2) INFORMATION FOR SEQ ID NO:404:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO:404:

AACCUGCAU UAAUA 15

( 2 ) INFORMATION FOR SEQ ID NO:405:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:405:

CUGUCAUUAA UAAAG       15

( 2 ) INFORMATION FOR SEQ ID NO:406:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:406:

UGUCAUUAAU AAAGA       15

( 2 ) INFORMATION FOR SEQ ID NO:407:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:407:

CAUUAAUAAA GAAAU       1

( 2 ) INFORMATION FOR SEQ ID NO:408:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:408:

AAGAAAUACA UUGAC       15

( 2 ) INFORMATION FOR SEQ ID NO:409:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:409:

AAUACAUUGA CCGCC       15

( 2 ) INFORMATION FOR SEQ ID NO:410:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:410:

AAUACAUUGA CCGCC       15

( 2 ) INFORMATION FOR SEQ ID NO:411:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:411:

AGGCAGUUCC UGGAU 15

( 2 ) INFORMATION FOR SEQ ID NO:412:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:412:

GGCAGUUCCU GGAUU 15

( 2 ) INFORMATION FOR SEQ ID NO:413:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:413:

CUGGAUUACC UGCAA 15

( 2 ) INFORMATION FOR SEQ ID NO:414:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:414:

CAAGAGUUCC UUGGU 15

( 2 ) INFORMATION FOR SEQ ID NO:415:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:415:

AAGAGUUCCU UGGUG 15

( 2 ) INFORMATION FOR SEQ ID NO:416:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:416:

AGUUCCUUGG UGUGA 15

( 2 ) INFORMATION FOR SEQ ID NO:417:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:417:

UCACAAUUUA AGUUA                                                                15

(2) INFORMATION FOR SEQ ID NO:418:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION:SEQ ID NO:418:

CACAAUUUAA GUUAA                                                                 1

(2) INFORMATION FOR SEQ ID NO:419:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:419:

ACAAUUUAAG UUAAA                                                                15

(2) INFORMATION FOR SEQ ID NO:420:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:420:

ACAAUUUAAG UUAAA                                                                15

(2) INFORMATION FOR SEQ ID NO:421:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:421:

AAAUUGUCAA CAGAU                                                                15

(2) INFORMATION FOR SEQ ID NO:422:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:422:

GCUGUUUCCA UUUAU                                                                15

(2) INFORMATION FOR SEQ ID NO:423:

(i) SEQUENCE CHARACTERISTICS:
      (A) LENGTH: 15 base pairs
      (B) TYPE: nucleic acid ( C ) STRANDEDNESS: single
( D ) TOPOLOGY: linear ( x i ) SEQUENCE DESCRIPTION: SEQ ID NO:423:

UUUCCAUUUA UAUUU 15

( 2 ) INFORMATION FOR SEQ ID NO:424:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:424:

UUAUAUUUAU GUCCU 15

( 2 ) INFORMATION FOR SEQ ID NO:425:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:425:

UUAUAUUUAU GUCCU 15

( 2 ) INFORMATION FOR SEQ ID NO:426:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:426:

UAUAUUUAUG UCCUG 15

( 2 ) INFORMATION FOR SEQ ID NO:427:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:427:

UAUAUUUAUG UCCUG 15

( 2 ) INFORMATION FOR SEQ ID NO:428:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:428:

UUUAUGCCU GUAGU 15

( 2 ) INFORMATION FOR SEQ ID NO:429:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION:SEQ ID NO:429:

UUUAUGUCCU GUAGU                                                                                    1 5

( 2 ) INFORMATION FOR SEQ ID NO:430:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:430:

AAAGUGUUUA ACCUU                                                                                    1 5

( 2 ) INFORMATION FOR SEQ ID NO:431:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:431:

AAGUGUUUAA CCUUU                                                                                    1 5

( 2 ) INFORMATION FOR SEQ ID NO:432:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:432:

UUAACCUUUU UGUAU                                                                                    1 5

( 2 ) INFORMATION FOR SEQ ID NO:433:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:433:

CAAGGCUUUG UGCAU                                                                                    1 5

( 2 ) INFORMATION FOR SEQ ID NO:434:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:434:

CUGAGUUAUA CUCCC                                                                                    1 5

( 2 ) INFORMATION FOR SEQ ID NO:435:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:435:

GAGUUAUACU CCCUC 15

( 2 ) INFORMATION FOR SEQ ID NO:436:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:436:

ACUCCCUCCC CCUCA 15

( 2 ) INFORMATION FOR SEQ ID NO:437:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:437:

ACUCCCUCCC CCUCA 15

( 2 ) INFORMATION FOR SEQ ID NO:438:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:438:

AUCCUCUUCG UUGCA 15

( 2 ) INFORMATION FOR SEQ ID NO:439:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:439:

UCCUCUUCGU UGCAU 15

( 2 ) INFORMATION FOR SEQ ID NO:440:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:440:

CAAGUAUUCC AGGCU 1

( 2 ) INFORMATION FOR SEQ ID NO:441:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:441:

AAGUAUUCCA GGCUG 15

( 2 ) INFORMATION FOR SEQ ID NO:442:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:442:

AAGUAUUCCA GGCUG    15

( 2 ) INFORMATION FOR SEQ ID NO:443:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:443:

GAACUCUUGG UCCAG    15

( 2 ) INFORMATION FOR SEQ ID NO:444:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:444:

UCUUGGUCCA GAUGG    15

( 2 ) INFORMATION FOR SEQ ID NO:445:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:445:

UUAGCAUCCU UUCUC    15

( 2 ) INFORMATION FOR SEQ ID NO:446:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:446:

GCAUCCUUUC UCCUA    15

( 2 ) INFORMATION FOR SEQ ID NO:447:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:447:

GCAUCCUUUC UCCUA    15

( 2 ) INFORMATION FOR SEQ ID NO:448:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:448:

AUCCUUUCUC CUAGC                                          15

( 2 ) INFORMATION FOR SEQ ID NO:449:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:449:

GCCCCUUUAG AUAGA                                         15

( 2 ) INFORMATION FOR SEQ ID NO:450:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:450:

AGAUGAUACU UAAUG                                         15

( 2 ) INFORMATION FOR SEQ ID NO:451:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:451:

UGAUACUUAA UGACU                                         1

( 2 ) INFORMATION FOR SEQ ID NO:452:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:452:

UGACUCUCUU GCUGA                                         15

( 2 ) INFORMATION FOR SEQ ID NO:453:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:453:

CGGGGCUUCC UGCUC                                         15

( 2 ) INFORMATION FOR SEQ ID NO:454:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:454:

UCCUGCUCCU AUCUA 15

( 2 ) INFORMATION FOR SEQ ID NO:455:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:455:

UGCUCCUAUC UAACU 15

( 2 ) INFORMATION FOR SEQ ID NO:456:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:456:

CUCCUAUCUA ACUUC 15

( 2 ) INFORMATION FOR SEQ ID NO:457:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:457:

CUCCUAUCUA ACUUC 15

( 2 ) INFORMATION FOR SEQ ID NO:458:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:458:

CCUAUCUAAC UUCAA 15

( 2 ) INFORMATION FOR SEQ ID NO:459:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:459:

UUCAAUUUAA UACCC 15

( 2 ) INFORMATION FOR SEQ ID NO:460:

( i ) SEQUENCE CHARACTERISTICS:
      ( A ) LENGTH: 15 base pairs ( B ) TYPE: nucleic acid
        ( C ) STRANDEDNESS: single
        ( D ) TOPOLOGY: linear ( x i ) SEQUENCE DESCRIPTION: SEQ ID NO:460:

UGACUUUUCU UAUGU                                                                            15

( 2 ) INFORMATION FOR SEQ ID NO:461:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:461:

GCUGGAUUUU GGAAA                                                                            15

( 2 ) INFORMATION FOR SEQ ID NO:462:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:462:

GCUGGAUUUU GGAAA                                                                             1

( 2 ) INFORMATION FOR SEQ ID NO:463:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:463:

CUGGAUUUUG GAAAA                                                                            15

( 2 ) INFORMATION FOR SEQ ID NO:464:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:464:

UGGAUUUUGG AAAAG                                                                            15

( 2 ) INFORMATION FOR SEQ ID NO:465:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:465:

GGGACAUCUC CUUGC                                                                            15

( 2 ) INFORMATION FOR SEQ ID NO:466:

( i ) SEQUENCE CHARACTERISTICS:
        ( A ) LENGTH: 15 base pairs
        ( B ) TYPE: nucleic acid
        ( C ) STRANDEDNESS: single ( D ) TOPOLOGY: linear ( x i ) SEQUENCE DESCRIPTION: SEQ ID NO:466:

GACAUCUCCU UGCAG                                                                15

( 2 ) INFORMATION FOR SEQ ID NO:467:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:467:

UGGGCCUUAC UUCUC                                                                15

( 2 ) INFORMATION FOR SEQ ID NO:468:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:468:

GGGCCUUACU UCUCC                                                                15

( 2 ) INFORMATION FOR SEQ ID NO:469:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:469:

CUUACUUCUC CGUGU                                                                15

( 2 ) INFORMATION FOR SEQ ID NO:470:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:470:

UGAACUUAAG AAGCA                                                                15

( 2 ) INFORMATION FOR SEQ ID NO:471:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:471:

GCAAAGUAAA UACCA                                                                15

( 2 ) INFORMATION FOR SEQ ID NO:472:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:472:

GCAAAGUAAA UACCA     15

( 2 ) INFORMATION FOR SEQ ID NO:473:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:473:

GCAAAGUAAA UACCA     1

( 2 ) INFORMATION FOR SEQ ID NO:474:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:474:

AAAGCAUAAA AUGGU     15

( 2 ) INFORMATION FOR SEQ ID NO:475:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:475:

AAAUGGUUGG GAUGU     15

( 2 ) INFORMATION FOR SEQ ID NO:476:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:476:

UGUUAUUCAG GUAUC     15

( 2 ) INFORMATION FOR SEQ ID NO:477:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:477:

UUCAGGUAUC AGGGU     15

( 2 ) INFORMATION FOR SEQ ID NO:478:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:478:

```
CAGGUAUCAG GGUCA                                                           15
```

( 2 ) INFORMATION FOR SEQ ID NO:479:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:479:

```
UCAGGGUCAC UGGAG                                                           15
```

( 2 ) INFORMATION FOR SEQ ID NO:480:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:480:

```
CCCCAGUUUA CUCCA                                                           15
```

( 2 ) INFORMATION FOR SEQ ID NO:481:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:481:

```
CCAGUUUACU CCAGG                                                           15
```

( 2 ) INFORMATION FOR SEQ ID NO:482:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:482:

```
CCAGUUUACU CCAGG                                                           15
```

( 2 ) INFORMATION FOR SEQ ID NO:483:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:483:

```
GUUUACUCCA GGAAA                                                           15
```

( 2 ) INFORMATION FOR SEQ ID NO:484:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:484:

```
AUGCUUUUAU UUAAU                                                            1
```

( 2 ) INFORMATION FOR SEQ ID NO:485:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:485:

AUGCUUUUAU UUAAU        15

( 2 ) INFORMATION FOR SEQ ID NO:486:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:486:

AUGCUUUUAU UUAAU        15

( 2 ) INFORMATION FOR SEQ ID NO:487:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:487:

UGCUUUUAUU UAAUU        15

( 2 ) INFORMATION FOR SEQ ID NO:488:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:488:

UGCUUUUAUU UAAUU        15

( 2 ) INFORMATION FOR SEQ ID NO:489:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:489:

UUUUAUUUAA UUCUG        15

( 2 ) INFORMATION FOR SEQ ID NO:490:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:490:

UUUUAUUUAA UUCUG        15

( 2 ) INFORMATION FOR SEQ ID NO:491:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:491:

UUUAUUUAAU UCUGU                          15

(2) INFORMATION FOR SEQ ID NO:492:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:492:

UUUAAUUCUG UAAGA                          15

(2) INFORMATION FOR SEQ ID NO:493:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:493:

AUUCUGUAAG AUGUU                          15

(2) INFORMATION FOR SEQ ID NO:494:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:494:

UGUUCAUAUU AUUUA                          15

(2) INFORMATION FOR SEQ ID NO:495:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION:SEQ ID NO:495:

UGUUCAUAUU AUUUA                          1

(2) INFORMATION FOR SEQ ID NO:496:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:496:

UUCAUAUUAU UUAUG                          15

(2) INFORMATION FOR SEQ ID NO:497:

(i) SEQUENCE CHARACTERISTICS:

( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:497:

UCAUAUUAUU UAUGA 15

( 2 ) INFORMATION FOR SEQ ID NO:498:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:498:

AUAUUAUUUA UGAUG 15

( 2 ) INFORMATION FOR SEQ ID NO:499:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:499:

AUGGAUUCAG UAAGU 15

( 2 ) INFORMATION FOR SEQ ID NO:500:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:500:

AUUCAGUAAG UUAAU 15

( 2 ) INFORMATION FOR SEQ ID NO:501:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:501:

AGUAAGUUAA UAUUU 15

( 2 ) INFORMATION FOR SEQ ID NO:502:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:502:

AGUAAGUUAA UAUUU 15

( 2 ) INFORMATION FOR SEQ ID NO:503:

( i ) SEQUENCE CHARACTERISTICS:
( A ) LENGTH: 15 base pairs
( B ) TYPE: nucleic acid ( C ) STRANDEDNESS: single
        ( D ) TOPOLOGY: linear ( x i ) SEQUENCE DESCRIPTION: SEQ ID NO:503:

GUAAGUUAAU AUUUA                                                                                    15

( 2 ) INFORMATION FOR SEQ ID NO:504:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:504:

AGUUAAUAUU UAUUA                                                                                    15

( 2 ) INFORMATION FOR SEQ ID NO:505:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:505:

AGUUAAUAUU UAUUA                                                                                    15

( 2 ) INFORMATION FOR SEQ ID NO:506:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:506:

UUAAUAUUUA UUACA                                                                                     1

( 2 ) INFORMATION FOR SEQ ID NO:507:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:507:

UUAAUAUUUA UUACA                                                                                    15

( 2 ) INFORMATION FOR SEQ ID NO:508:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:508:

UUAAUAUUUA UUACA                                                                                    15

( 2 ) INFORMATION FOR SEQ ID NO:509:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:509:

U A A U A U U U A U   U A C A C                                                                 15

( 2 ) INFORMATION FOR SEQ ID NO:510:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:510:

U A A U A U U U A U   U A C A C                                                                 15

( 2 ) INFORMATION FOR SEQ ID NO:511:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:511:

U A A U A U U U A U   U A C A C                                                                 15

( 2 ) INFORMATION FOR SEQ ID NO:512:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:512:

A A U A U U U A U U   A C A C G                                                                 15

( 2 ) INFORMATION FOR SEQ ID NO:513:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:513:

A A U A U U U A U U   A C A C G                                                                 15

( 2 ) INFORMATION FOR SEQ ID NO:514:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:514:

A A U A U U U A U U   A C A C G                                                                 15

( 2 ) INFORMATION FOR SEQ ID NO:515:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:515:

AAUAUUUAUU ACACG                                                                                                            15

( 2 ) INFORMATION FOR SEQ ID NO:516:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:516:

AUUUAUUACA CGUAU                                                                                                            15

( 2 ) INFORMATION FOR SEQ ID NO:517:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:517:

CACGUAUAUA AUAUU                                                                                                             1

( 2 ) INFORMATION FOR SEQ ID NO:518:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:518:

CACGUAUAUA AUAUU                                                                                                            15

( 2 ) INFORMATION FOR SEQ ID NO:519:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:519:

AUAUAAUAUU CUAAU                                                                                                            15

( 2 ) INFORMATION FOR SEQ ID NO:520:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:520:

AUAAUAUUCU AAUAA                                                                                                            15

( 2 ) INFORMATION FOR SEQ ID NO:521:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:521:

AUAAUAUUCU AAUAA                                                                                                            15

( 2 ) INFORMATION FOR SEQ ID NO:522:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:522:

UAAUAUUCUA AUAAA          15

( 2 ) INFORMATION FOR SEQ ID NO:523:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:523:

UAAUAUUCUA AUAAA          15

( 2 ) INFORMATION FOR SEQ ID NO:524:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:524:

UAAUAUUCUA AUAAA          15

( 2 ) INFORMATION FOR SEQ ID NO:525:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:525:

UAAUAUUCUA AUAAA          15

( 2 ) INFORMATION FOR SEQ ID NO:526:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:526:

AUAUUCUAAU AAAGC          15

( 2 ) INFORMATION FOR SEQ ID NO:527:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:527:

UUCUAAUAAA GCAGA          15

(2) INFORMATION FOR SEQ ID NO:528:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION:SEQ ID NO:528:

AGCAAAGCUG AUGAGGCCGA AAGGCCGAAA AGAGCG                         3

(2) INFORMATION FOR SEQ ID NO:529:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:529:

UUCAGCACUG AUGAGGCCGA AAGGCCGAAA GGAAGA                         36

(2) INFORMATION FOR SEQ ID NO:530:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:530:

CUUCAGCCUG AUGAGGCCGA AAGGCCGAAA AGGAAG                         36

(2) INFORMATION FOR SEQ ID NO:531:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:531:

GACUCUGCUG AUGAGGCCGA AAGGCCGAAA GUCUUC                         36

(2) INFORMATION FOR SEQ ID NO:532:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:532:

GACUCUGCUG AUGAGGCCGA AAGGCCGAAA GUCUUC                         36

(2) INFORMATION FOR SEQ ID NO:533:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:533:

UGACUCUCUG AUGAGGCCGA AAGGCCGAAA AGUCUU                         36

(2) INFORMATION FOR SEQ ID NO:534:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:534:

UUCUCAUCUG AUGAGGCCGA AAGGCCGAAA CUCUGA     36

( 2 ) INFORMATION FOR SEQ ID NO:535:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:535:

AGUGCAGCUG AUGAGGCCGA AAGGCCGAAA GCAUCC     36

( 2 ) INFORMATION FOR SEQ ID NO:536:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:536:

AAGUGCACUG AUGAGGCCGA AAGGCCGAAA AGCAUC     36

( 2 ) INFORMATION FOR SEQ ID NO:537:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:537:

AAGUGCACUG AUGAGGCCGA AAGGCCGAAA AGCAUC     36

( 2 ) INFORMATION FOR SEQ ID NO:538:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:538:

AACACUCCUG AUGAGGCCGA AAGGCCGAAA GUGCAG     36

( 2 ) INFORMATION FOR SEQ ID NO:539:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION:SEQ ID NO:539:

CACAGCUCUG AUGAGGCCGA AAGGCCGAAA GAGUCA     3

( 2 ) INFORMATION FOR SEQ ID NO:540:

( i ) SEQUENCE CHARACTERISTICS:
( A ) LENGTH: 36 base pairs (B) TYPE: nucleic acid
(C) STRANDEDNESS: single
(D) TOPOLOGY: linear (xi) SEQUENCE DESCRIPTION: SEQ ID NO:540:

UGGCCCACUG AUGAGGCCGA AAGGCCGAAA CACAGC 36

(2) INFORMATION FOR SEQ ID NO:541:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:541:

UCAUGGGCUG AUGAGGCCGA AAGGCCGAAA UCUCCA 36

(2) INFORMATION FOR SEQ ID NO:542:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:542:

CUCAUGGCUG AUGAGGCCGA AAGGCCGAAA AUCUCC 36

(2) INFORMATION FOR SEQ ID NO:543:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:543:

CUGUGUCCUG AUGAGGCCGA AAGGCCGAAA GGUCUC 36

(2) INFORMATION FOR SEQ ID NO:544:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:544:

CUGUGUCCUG AUGAGGCCGA AAGGCCGAAA GGUCUC 36

(2) INFORMATION FOR SEQ ID NO:545:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:545:

GCUCGGUCUG AUGAGGCCGA AAGGCCGAAA GCGGAC 36

(2) INFORMATION FOR SEQ ID NO:546:

(i) SEQUENCE CHARACTERISTICS:
(A) LENGTH: 36 base pairs
(B) TYPE: nucleic acid
(C) STRANDEDNESS: single ( D ) TOPOLOGY: linear ( x i ) SEQUENCE DESCRIPTION: SEQ ID NO:546:

GUCAACACUG AUGAGGCCGA AAGGCCGAAA GCUCGG  36

( 2 ) INFORMATION FOR SEQ ID NO:547:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:547:

GGACAGGCUG AUGAGGCCGA AAGGCCGAAA GCCUCA  36

( 2 ) INFORMATION FOR SEQ ID NO:548:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:548:

GGGACAGCUG AUGAGGCCGA AAGGCCGAAA AGCCUC  36

( 2 ) INFORMATION FOR SEQ ID NO:549:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:549:

GGGACAGCUG AUGAGGCCGA AAGGCCGAAA AGCCUC  36

( 2 ) INFORMATION FOR SEQ ID NO:550:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:550:

GAGUAGGCUG AUGAGGCCGA AAGGCCGAAA CAGGAA  3

( 2 ) INFORMATION FOR SEQ ID NO:551:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:551:

GAGUAGGCUG AUGAGGCCGA AAGGCCGAAA CAGGAA  36

( 2 ) INFORMATION FOR SEQ ID NO:552:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:552:

UUAUGAGCUG AUGAGGCCGA AAGGCCGAAA GGGACA                36

( 2 ) INFORMATION FOR SEQ ID NO:553:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:553:

UGAUUUUCUG AUGAGGCCGA AAGGCCGAAA UGAGUA                36

( 2 ) INFORMATION FOR SEQ ID NO:554:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:554:

UGAUUUUCUG AUGAGGCCGA AAGGCCGAAA UGAGUA                36

( 2 ) INFORMATION FOR SEQ ID NO:555:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:555:

AGCUGGUCUG AUGAGGCCGA AAGGCCGAAA UUUUUA                36

( 2 ) INFORMATION FOR SEQ ID NO:556:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:556:

AGCUGGUCUG AUGAGGCCGA AAGGCCGAAA UUUUUA                36

( 2 ) INFORMATION FOR SEQ ID NO:557:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:557:

AGCUGGUCUG AUGAGGCCGA AAGGCCGAAA UUUUUA                36

( 2 ) INFORMATION FOR SEQ ID NO:558:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:558:

UUUCUCCUG AUGAGGCCGA AAGGCCGAAA UGCAUA                36

( 2 ) INFORMATION FOR SEQ ID NO:559:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:559:

CCUGAAACUG AUGAGGCCGA AAGGCCGAAA UUUCUC                36

( 2 ) INFORMATION FOR SEQ ID NO:560:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:560:

CCUGAAACUG AUGAGGCCGA AAGGCCGAAA UUUCUC                36

( 2 ) INFORMATION FOR SEQ ID NO:561:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:561:

CCUGAAACUG AUGAGGCCGA AAGGCCGAAA UUUCUC                3

( 2 ) INFORMATION FOR SEQ ID NO:562:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:562:

CCUGAAACUG AUGAGGCCGA AAGGCCGAAA UUUCUC                36

( 2 ) INFORMATION FOR SEQ ID NO:563:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:563:

CCCCUGACUG AUGAGGCCGA AAGGCCGAAA GAUUUC                36

( 2 ) INFORMATION FOR SEQ ID NO:564:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:564:

CCCCUGACUG AUGAGGCCGA AAGGCCGAAA GAUUUC                36

( 2 ) INFORMATION FOR SEQ ID NO:565:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:565:

GCCCCUGCUG AUGAGGCCGA AAGGCCGAAA AGAUUU                    36

( 2 ) INFORMATION FOR SEQ ID NO:566:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:566:

AGCCCCUCUG AUGAGGCCGA AAGGCCGAAA AAGAUU                    36

( 2 ) INFORMATION FOR SEQ ID NO:567:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:567:

GUAUGUCCUG AUGAGGCCGA AAGGCCGAAA GCCCCU                    36

( 2 ) INFORMATION FOR SEQ ID NO:568:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:568:

UCUUCAGCUG AUGAGGCCGA AAGGCCGAAA UGUCUA                    36

( 2 ) INFORMATION FOR SEQ ID NO:569:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:569:

ACAGUUUCUG AUGAGGCCGA AAGGCCGAAA UUCUUC                    36

( 2 ) INFORMATION FOR SEQ ID NO:570:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:570:

ACAGUUUCUG AUGAGGCCGA AAGGCCGAAA UUCUUC                    36

( 2 ) INFORMATION FOR SEQ ID NO:571:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:571:

ACAGUUUCUG AUGAGGCCGA AAGGCCGAAA UUCUUC                    36

( 2 ) INFORMATION FOR SEQ ID NO:572:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:572:

UCCACAGCUG AUGAGGCCGA AAGGCCGAAA CCCCCA                    3

( 2 ) INFORMATION FOR SEQ ID NO:573:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:573:

UUUGGAACUG AUGAGGCCGA AAGGCCGAAA GCAUUU                    36

( 2 ) INFORMATION FOR SEQ ID NO:574:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:574:

UUUGGAACUG AUGAGGCCGA AAGGCCGAAA GCAUUU                    36

( 2 ) INFORMATION FOR SEQ ID NO:575:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:575:

GUUUGGCUG AUGAGGCCGA AAGGCCGAAA UAGCAU                     36

( 2 ) INFORMATION FOR SEQ ID NO:576:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:576:

GUUUGGCUG AUGAGGCCGA AAGGCCGAAA UAGCAU                     36

( 2 ) INFORMATION FOR SEQ ID NO:577:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:577:

GGUUUUGCUG AUGAGGCCGA AAGGCCGAAA AUAGCA    36

(2) INFORMATION FOR SEQ ID NO:578:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:578:

UAUUAAUCUG AUGAGGCCGA AAGGCCGAAA CAGGUU    36

(2) INFORMATION FOR SEQ ID NO:579:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:579:

CUUUAUUCUG AUGAGGCCGA AAGGCCGAAA UGACAG    36

(2) INFORMATION FOR SEQ ID NO:580:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:580:

UCUUUAUCUG AUGAGGCCGA AAGGCCGAAA AUGACA    36

(2) INFORMATION FOR SEQ ID NO:581:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:581:

AUUUCUUCUG AUGAGGCCGA AAGGCCGAAA UUAAUG    36

(2) INFORMATION FOR SEQ ID NO:582:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:582:

GUCAAUGCUG AUGAGGCCGA AAGGCCGAAA UUUCUU    36

(2) INFORMATION FOR SEQ ID NO:583:

(i) SEQUENCE CHARACTERISTICS:
(A) LENGTH: 36 base pairs
(B) TYPE: nucleic acid ( C ) STRANDEDNESS: single
( D ) TOPOLOGY: linear ( x i ) SEQUENCE DESCRIPTION:SEQ ID NO:583:

GGCGGUCCUG AUGAGGCCGA AAGGCCGAAA UGUAUU     3

( 2 ) INFORMATION FOR SEQ ID NO:584:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:584:

GGCGGUCCUG AUGAGGCCGA AAGGCCGAAA UGUAUU     36

( 2 ) INFORMATION FOR SEQ ID NO:585:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:585:

AUCCAGGCUG AUGAGGCCGA AAGGCCGAAA CUGCCU     36

( 2 ) INFORMATION FOR SEQ ID NO:586:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:586:

AAUCCAGCUG AUGAGGCCGA AAGGCCGAAA ACUGCC     36

( 2 ) INFORMATION FOR SEQ ID NO:587:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:587:

UUGCAGGCUG AUGAGGCCGA AAGGCCGAAA AUCCAG     36

( 2 ) INFORMATION FOR SEQ ID NO:588:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:588:

ACCAAGGCUG AUGAGGCCGA AAGGCCGAAA CUCUUG     36

( 2 ) INFORMATION FOR SEQ ID NO:589:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:589:

CACCAAGCUG AUGAGGCCGA AAGGCCGAAA ACUCUU  36

( 2 ) INFORMATION FOR SEQ ID NO:590:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:590:

UCACACCCUG AUGAGGCCGA AAGGCCGAAA GGAACU  36

( 2 ) INFORMATION FOR SEQ ID NO:591:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:591:

UAACUUACUG AUGAGGCCGA AAGGCCGAAA UUGUGA  36

( 2 ) INFORMATION FOR SEQ ID NO:592:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:592:

UUAACUUCUG AUGAGGCCGA AAGGCCGAAA AUUGUG  36

( 2 ) INFORMATION FOR SEQ ID NO:593:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:593:

UUUAACUCUG AUGAGGCCGA AAGGCCGAAA AAUUGU  36

( 2 ) INFORMATION FOR SEQ ID NO:594:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:594:

UUUAACUCUG AUGAGGCCGA AAGGCCGAAA AAUUGU  3

( 2 ) INFORMATION FOR SEQ ID NO:595:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:595:

AUCUGUUCUG AUGAGGCCGA AAGGCCGAAA CAAUUU 36

(2) INFORMATION FOR SEQ ID NO:596:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:596:

AUAAAUGCUG AUGAGGCCGA AAGGCCGAAA AACAGC 36

(2) INFORMATION FOR SEQ ID NO:597:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:597:

AAAUAUACUG AUGAGGCCGA AAGGCCGAAA UGGAAA 36

(2) INFORMATION FOR SEQ ID NO:598:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:598:

AGGACAUCUG AUGAGGCCGA AAGGCCGAAA AUAUAA 36

(2) INFORMATION FOR SEQ ID NO:599:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:599:

AGGACAUCUG AUGAGGCCGA AAGGCCGAAA AUAUAA 36

(2) INFORMATION FOR SEQ ID NO:600:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:600:

CAGGACACUG AUGAGGCCGA AAGGCCGAAA AAUAUA 36

(2) INFORMATION FOR SEQ ID NO:601:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:601:

CAGGACACUG AUGAGGCCGA AAGGCCGAAA AAUAUA 36

( 2 ) INFORMATION FOR SEQ ID NO:602:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:602:

ACUACAGCUG AUGAGGCCGA AAGGCCGAAA CAUAAA     36

( 2 ) INFORMATION FOR SEQ ID NO:603:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:603:

ACUACAGCUG AUGAGGCCGA AAGGCCGAAA CAUAAA     36

( 2 ) INFORMATION FOR SEQ ID NO:604:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:604:

AAGGUUACUG AUGAGGCCGA AAGGCCGAAA CACUUU     36

( 2 ) INFORMATION FOR SEQ ID NO:605:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:605:

AAAGGUUCUG AUGAGGCCGA AAGGCCGAAA ACACUU     3

( 2 ) INFORMATION FOR SEQ ID NO:606:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:606:

AUACAAACUG AUGAGGCCGA AAGGCCGAAA GGUUAA     36

( 2 ) INFORMATION FOR SEQ ID NO:607:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:607:

AUGCACACUG AUGAGGCCGA AAGGCCGAAA GCCUUG     36

( 2 ) INFORMATION FOR SEQ ID NO:608:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:608:

GGGAGUACUG AUGAGGCCGA AAGGCCGAAA ACUCAG            36

( 2 ) INFORMATION FOR SEQ ID NO:609:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:609:

GAGGGAGCUG AUGAGGCCGA AAGGCCGAAA UAACUC            36

( 2 ) INFORMATION FOR SEQ ID NO:610:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:610:

UGAGGGCUG AUGAGGCCGA AAGGCCGAAA GGGAGU            36

( 2 ) INFORMATION FOR SEQ ID NO:611:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:611:

UGAGGGCUG AUGAGGCCGA AAGGCCGAAA GGGAGU            36

( 2 ) INFORMATION FOR SEQ ID NO:612:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:612:

UGCAACGCUG AUGAGGCCGA AAGGCCGAAA GAGGAU            36

( 2 ) INFORMATION FOR SEQ ID NO:613:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:613:

AUGCAACCUG AUGAGGCCGA AAGGCCGAAA AGAGGA            36

( 2 ) INFORMATION FOR SEQ ID NO:614:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:614:

AGCCUGGCUG AUGAGGCCGA AAGGCCGAAA UACUUG          36

( 2 ) INFORMATION FOR SEQ ID NO:615:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:615:

CAGCCUGCUG AUGAGGCCGA AAGGCCGAAA AUACUU          36

( 2 ) INFORMATION FOR SEQ ID NO:616:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION:SEQ ID NO:616:

CAGCCUGCUG AUGAGGCCGA AAGGCCGAAA AUACUU          3

( 2 ) INFORMATION FOR SEQ ID NO:617:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:617:

CUGGACCCUG AUGAGGCCGA AAGGCCGAAA GAGUUC          36

( 2 ) INFORMATION FOR SEQ ID NO:618:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:618:

CCAUCUGCUG AUGAGGCCGA AAGGCCGAAA CCAAGA          36

( 2 ) INFORMATION FOR SEQ ID NO:619:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:619:

GAGAAAGCUG AUGAGGCCGA AAGGCCGAAA UGCUAA          36

( 2 ) INFORMATION FOR SEQ ID NO:620:

( i ) SEQUENCE CHARACTERISTICS:
    ( A ) LENGTH: 36 base pairs ( B ) TYPE: nucleic acid
        ( C ) STRANDEDNESS: single
        ( D ) TOPOLOGY: linear ( x i ) SEQUENCE DESCRIPTION: SEQ ID NO:620:

UAGGAGACUG AUGAGGCCGA AAGGCCGAAA GGAUGC 36

( 2 ) INFORMATION FOR SEQ ID NO:621:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:621:

UAGGAGACUG AUGAGGCCGA AAGGCCGAAA GGAUGC 36

( 2 ) INFORMATION FOR SEQ ID NO:622:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:622:

GCUAGGACUG AUGAGGCCGA AAGGCCGAAA AAGGAU 36

( 2 ) INFORMATION FOR SEQ ID NO:623:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:623:

UCUAUCUCUG AUGAGGCCGA AAGGCCGAAA AGGGGC 36

( 2 ) INFORMATION FOR SEQ ID NO:624:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:624:

CAUUAAGCUG AUGAGGCCGA AAGGCCGAAA UCAUCU 36

( 2 ) INFORMATION FOR SEQ ID NO:625:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:625:

AGUCAUUCUG AUGAGGCCGA AAGGCCGAAA GUAUCA 36

( 2 ) INFORMATION FOR SEQ ID NO:626:

( i ) SEQUENCE CHARACTERISTICS:
        ( A ) LENGTH: 36 base pairs
        ( B ) TYPE: nucleic acid
        ( C ) STRANDEDNESS: single ( D ) TOPOLOGY: linear ( x i ) SEQUENCE DESCRIPTION: SEQ ID NO:626:

UCAGCAACUG AUGAGGCCGA AAGGCCGAAA GAGUCA         36

( 2 ) INFORMATION FOR SEQ ID NO:627:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:627:

GAGCAGGCUG AUGAGGCCGA AAGGCCGAAA GCCCCG         3

( 2 ) INFORMATION FOR SEQ ID NO:628:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:628:

UAGAUAGCUG AUGAGGCCGA AAGGCCGAAA GCAGGA         36

( 2 ) INFORMATION FOR SEQ ID NO:629:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:629:

AGUUAGACUG AUGAGGCCGA AAGGCCGAAA GGAGCA         36

( 2 ) INFORMATION FOR SEQ ID NO:630:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:630:

GAAGUUACUG AUGAGGCCGA AAGGCCGAAA UAGGAG         36

( 2 ) INFORMATION FOR SEQ ID NO:631:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:631:

GAAGUUACUG AUGAGGCCGA AAGGCCGAAA UAGGAG         36

( 2 ) INFORMATION FOR SEQ ID NO:632:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:632:

UUGAAGCUG AUGAGGCCGA AAGGCCGAAA GAUAGG   36

( 2 ) INFORMATION FOR SEQ ID NO:633:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:633:

GGGUAUUCUG AUGAGGCCGA AAGGCCGAAA AUUGAA   36

( 2 ) INFORMATION FOR SEQ ID NO:634:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:634:

ACAUAAGCUG AUGAGGCCGA AAGGCCGAAA AAGUCA   36

( 2 ) INFORMATION FOR SEQ ID NO:635:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:635:

UUUCCAACUG AUGAGGCCGA AAGGCCGAAA UCCAGC   36

( 2 ) INFORMATION FOR SEQ ID NO:636:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:636:

UUUCCAACUG AUGAGGCCGA AAGGCCGAAA UCCAGC   36

( 2 ) INFORMATION FOR SEQ ID NO:637:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:637:

UUUUCCACUG AUGAGGCCGA AAGGCCGAAA AUCCAG   36

( 2 ) INFORMATION FOR SEQ ID NO:638:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:638:

CUUUCCCUG AUGAGGCCGA AAGGCCGAAA AAUCCA  3

( 2 ) INFORMATION FOR SEQ ID NO:639:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:639:

GCAAGGACUG AUGAGGCCGA AAGGCCGAAA UGUCCC  36

( 2 ) INFORMATION FOR SEQ ID NO:640:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:640:

CUGCAAGCUG AUGAGGCCGA AAGGCCGAAA GAUGUC  36

( 2 ) INFORMATION FOR SEQ ID NO:641:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:641:

GAGAAGUCUG AUGAGGCCGA AAGGCCGAAA GGCCCA  36

( 2 ) INFORMATION FOR SEQ ID NO:642:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:642:

GGAGAAGCUG AUGAGGCCGA AAGGCCGAAA AGGCCC  36

( 2 ) INFORMATION FOR SEQ ID NO:643:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:643:

ACACGGACUG AUGAGGCCGA AAGGCCGAAA AGUAAG  36

( 2 ) INFORMATION FOR SEQ ID NO:644:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:644:

UGCUUCUCUG AUGAGGCCGA AAGGCCGAAA AGUUCA  36

( 2 ) INFORMATION FOR SEQ ID NO:645:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:645:

UGGUAUUCUG AUGAGGCCGA AAGGCCGAAA CUUUGC      36

( 2 ) INFORMATION FOR SEQ ID NO:646:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:646:

UGGUAUUCUG AUGAGGCCGA AAGGCCGAAA CUUUGC      36

( 2 ) INFORMATION FOR SEQ ID NO:647:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:647:

UGGUAUUCUG AUGAGGCCGA AAGGCCGAAA CUUUGC      36

( 2 ) INFORMATION FOR SEQ ID NO:648:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:648:

ACCAUUUCUG AUGAGGCCGA AAGGCCGAAA UGCUUU      36

( 2 ) INFORMATION FOR SEQ ID NO:649:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:649:

ACAUCCCUG AUGAGGCCGA AAGGCCGAAA CCAUUU      3

( 2 ) INFORMATION FOR SEQ ID NO:650:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:650:

GAUACCUCUG AUGAGGCCGA AAGGCCGAAA AUAACA      36

( 2 ) INFORMATION FOR SEQ ID NO:651:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:651:

ACCCUGACUG AUGAGGCCGA AAGGCCGAAA CCUGAA                36

(2) INFORMATION FOR SEQ ID NO:652:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:652:

UGACCCUCUG AUGAGGCCGA AAGGCCGAAA UACCUG                36

(2) INFORMATION FOR SEQ ID NO:653:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:653:

CUCCAGUCUG AUGAGGCCGA AAGGCCGAAA CCCUGA                36

(2) INFORMATION FOR SEQ ID NO:654:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:654:

UGGAGUACUG AUGAGGCCGA AAGGCCGAAA CUGGGG                36

(2) INFORMATION FOR SEQ ID NO:655:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:655:

CCUGGAGCUG AUGAGGCCGA AAGGCCGAAA AACUGG                36

(2) INFORMATION FOR SEQ ID NO:656:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:656:

CCUGGAGCUG AUGAGGCCGA AAGGCCGAAA AACUGG                36

(2) INFORMATION FOR SEQ ID NO:657:

(i) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:657:

UUUCCUGCUG AUGAGGCCGA AAGGCCGAAA GUAAAC    36

(2) INFORMATION FOR SEQ ID NO:658:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:658:

AUUAAAUCUG AUGAGGCCGA AAGGCCGAAA AAGCAU    36

(2) INFORMATION FOR SEQ ID NO:659:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:659:

AUUAAAUCUG AUGAGGCCGA AAGGCCGAAA AAGCAU    36

(2) INFORMATION FOR SEQ ID NO:660:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION:SEQ ID NO:660:

AUUAAAUCUG AUGAGGCCGA AAGGCCGAAA AAGCAU    3

(2) INFORMATION FOR SEQ ID NO:661:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:661:

AAUUAAACUG AUGAGGCCGA AAGGCCGAAA AAAGCA    36

(2) INFORMATION FOR SEQ ID NO:662:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:662:

AAUUAAACUG AUGAGGCCGA AAGGCCGAAA AAAGCA    36

(2) INFORMATION FOR SEQ ID NO:663:

(i) SEQUENCE CHARACTERISTICS:
(A) LENGTH: 36 base pairs
(B) TYPE: nucleic acid (C) STRANDEDNESS: single
(D) TOPOLOGY: linear (xi) SEQUENCE DESCRIPTION: SEQ ID NO:663:

CAGAAUUCUG AUGAGGCCGA AAGGCCGAAA AUAAAA    36

(2) INFORMATION FOR SEQ ID NO:664:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:664:

CAGAAUUCUG AUGAGGCCGA AAGGCCGAAA AUAAAA    36

(2) INFORMATION FOR SEQ ID NO:665:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:665:

ACAGAAUCUG AUGAGGCCGA AAGGCCGAAA AAUAAA    36

(2) INFORMATION FOR SEQ ID NO:666:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:666:

UCUUACACUG AUGAGGCCGA AAGGCCGAAA AUUAAA    36

(2) INFORMATION FOR SEQ ID NO:667:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:667:

AACAUCUCUG AUGAGGCCGA AAGGCCGAAA CAGAAU    36

(2) INFORMATION FOR SEQ ID NO:668:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:668:

UAAAUAACUG AUGAGGCCGA AAGGCCGAAA UGAACA    36

(2) INFORMATION FOR SEQ ID NO:669:

(i) SEQUENCE CHARACTERISTICS:
      (A) LENGTH: 36 base pairs
      (B) TYPE: nucleic acid
      (C) STRANDEDNESS: single
      (D) TOPOLOGY: linear ( x i ) SEQUENCE DESCRIPTION: SEQ ID NO:669:

UAAAUAACUG AUGAGGCCGA AAGGCCGAAA UGAACA        36

( 2 ) INFORMATION FOR SEQ ID NO:670:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:670:

CAUAAAUCUG AUGAGGCCGA AAGGCCGAAA UAUGAA        36

( 2 ) INFORMATION FOR SEQ ID NO:671:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:671:

UCAUAAACUG AUGAGGCCGA AAGGCCGAAA AUAUGA        3

( 2 ) INFORMATION FOR SEQ ID NO:672:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:672:

CAUCAUACUG AUGAGGCCGA AAGGCCGAAA UAAUAU        36

( 2 ) INFORMATION FOR SEQ ID NO:673:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:673:

ACUUACUCUG AUGAGGCCGA AAGGCCGAAA AUCCAU        36

( 2 ) INFORMATION FOR SEQ ID NO:674:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:674:

AUUAACUCUG AUGAGGCCGA AAGGCCGAAA CUGAAU        36

( 2 ) INFORMATION FOR SEQ ID NO:675:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:675:

AAAUAUUCUG AUGAGGCCGA AAGGCCGAAA CUUACU                                36

( 2 ) INFORMATION FOR SEQ ID NO:676:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:676:

AAAUAUUCUG AUGAGGCCGA AAGGCCGAAA CUUACU                                36

( 2 ) INFORMATION FOR SEQ ID NO:677:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:677:

UAAAUAUCUG AUGAGGCCGA AAGGCCGAAA ACUUAC                                36

( 2 ) INFORMATION FOR SEQ ID NO:678:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:678:

UAAUAAACUG AUGAGGCCGA AAGGCCGAAA UUAACU                                36

( 2 ) INFORMATION FOR SEQ ID NO:679:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:679:

UAAUAAACUG AUGAGGCCGA AAGGCCGAAA UUAACU                                36

( 2 ) INFORMATION FOR SEQ ID NO:680:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:680:

UGUAAUACUG AUGAGGCCGA AAGGCCGAAA UAUUAA                                36

( 2 ) INFORMATION FOR SEQ ID NO:681:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:681:

UGUAAUACUG AUGAGGCCGA AAGGCCGAAA UAUUAA                                36

( 2 ) INFORMATION FOR SEQ ID NO:682:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:682:

UGUAAUACUG AUGAGGCCGA AAGGCCGAAA UAUUAA                                         3

( 2 ) INFORMATION FOR SEQ ID NO:683:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:683:

GUGUAAUCUG AUGAGGCCGA AAGGCCGAAA AUAUUA                                         3 6

( 2 ) INFORMATION FOR SEQ ID NO:684:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:684:

GUGUAAUCUG AUGAGGCCGA AAGGCCGAAA AUAUUA                                         3 6

( 2 ) INFORMATION FOR SEQ ID NO:685:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:685:

GUGUAAUCUG AUGAGGCCGA AAGGCCGAAA AUAUUA                                         3 6

( 2 ) INFORMATION FOR SEQ ID NO:686:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:686:

CGUGUAACUG AUGAGGCCGA AAGGCCGAAA AAUAUU                                         3 6

( 2 ) INFORMATION FOR SEQ ID NO:687:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:687:

CGUGUAACUG AUGAGGCCGA AAGGCCGAAA AAUAUU                                         3 6

( 2 ) INFORMATION FOR SEQ ID NO:688:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:688:

CGUGUAACUG AUGAGGCCGA AAGGCCGAAA AAUAUU       36

( 2 ) INFORMATION FOR SEQ ID NO:689:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:689:

CGUGUAACUG AUGAGGCCGA AAGGCCGAAA AAUAUU       36

( 2 ) INFORMATION FOR SEQ ID NO:690:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:690:

AUACGUGCUG AUGAGGCCGA AAGGCCGAAA AUAAAU       36

( 2 ) INFORMATION FOR SEQ ID NO:691:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:691:

AAUAUUACUG AUGAGGCCGA AAGGCCGAAA UACGUG       36

( 2 ) INFORMATION FOR SEQ ID NO:692:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:692:

AAUAUUACUG AUGAGGCCGA AAGGCCGAAA UACGUG       36

( 2 ) INFORMATION FOR SEQ ID NO:693:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:693:

AUUAGAACUG AUGAGGCCGA AAGGCCGAAA UUAUAU       3

( 2 ) INFORMATION FOR SEQ ID NO:694:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:694:

UUAUUAGCUG AUGAGGCCGA AAGGCCGAAA UAUUAU     36

( 2 ) INFORMATION FOR SEQ ID NO:695:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:695:

UUAUUAGCUG AUGAGGCCGA AAGGCCGAAA UAUUAU     36

( 2 ) INFORMATION FOR SEQ ID NO:696:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:696:

UUUAUUACUG AUGAGGCCGA AAGGCCGAAA AUAUUA     36

( 2 ) INFORMATION FOR SEQ ID NO:697:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:697:

UUUAUUACUG AUGAGGCCGA AAGGCCGAAA AUAUUA     36

( 2 ) INFORMATION FOR SEQ ID NO:698:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:698:

UUUAUUACUG AUGAGGCCGA AAGGCCGAAA AUAUUA     36

( 2 ) INFORMATION FOR SEQ ID NO:699:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:699:

UUUAUUACUG AUGAGGCCGA AAGGCCGAAA AUAUUA     36

( 2 ) INFORMATION FOR SEQ ID NO:700:

( i ) SEQUENCE CHARACTERISTICS:
    ( A ) LENGTH: 36 base pairs ( B ) TYPE: nucleic acid
( C ) STRANDEDNESS: single
( D ) TOPOLOGY: linear ( x i ) SEQUENCE DESCRIPTION: SEQ ID NO:700:

GCUUUAUCUG AUGAGGCCGA AAGGCCGAAA GAAUAU    36

( 2 ) INFORMATION FOR SEQ ID NO:701:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:701:

UCUGCUUCUG AUGAGGCCGA AAGGCCGAAA UUAGAA    36

( 2 ) INFORMATION FOR SEQ ID NO:702:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:702:

UACACGUAAG AAGCUCCAAC CAGAGAAACA CACGUUGUGG UACAUUACCU GGUA    54

( 2 ) INFORMATION FOR SEQ ID NO:703:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:703:

UGGAGCUGCC UACGUGUA    18

( 2 ) INFORMATION FOR SEQ ID NO:704:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION:SEQ ID NO:704:

GAGUAGAAAG AAGUGCCAAC CAGAGAAACA CACGUUGUGG UACAUUACCU GGUA    54

( 2 ) INFORMATION FOR SEQ ID NO:705:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:705:

UGGCACUGCU UUCUACUC    18

( 2 ) INFORMATION FOR SEQ ID NO:706:

( i ) SEQUENCE CHARACTERISTICS:
( A ) LENGTH: 54 base pairs
( B ) TYPE: nucleic acid
( C ) STRANDEDNESS: single ( D ) TOPOLOGY: linear ( x i ) SEQUENCE DESCRIPTION: SEQ ID NO:706:

UGGCUAUCAG AAGAGUUCAC CAGAGAAACA CACGUUGUGG UACAUUACCU GGUA          54

( 2 ) INFORMATION FOR SEQ ID NO:707:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:707:

GAACUCUGCU GAUAGCCA                                                  18

( 2 ) INFORMATION FOR SEQ ID NO:708:

( i ) SEQUENCE CHARACTERISTICS:
                ( A ) LENGTH: 54 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:708:

UGUACAGGAG AAGGAAUCAC CAGAGAAACA CACGUUGUGG UACAUUACCU GGUA          54

( 2 ) INFORMATION FOR SEQ ID NO:709:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:709:

GAUUCCUGUU CCUGUACA                                                  18

( 2 ) INFORMATION FOR SEQ ID NO:710:

( i ) SEQUENCE CHARACTERISTICS:
                ( A ) LENGTH: 54 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:710:

AGCUGAGAAG AAGAACACAC CAGAGAAACA CACGUUGUGG UACAUUACCU GGUA          54

( 2 ) INFORMATION FOR SEQ ID NO:711:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:711:

GUGUUCUGAC UCUCAGCU                                                  18

( 2 ) INFORMATION FOR SEQ ID NO:712:

( i ) SEQUENCE CHARACTERISTICS:
                ( A ) LENGTH: 54 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:712:

CCAGACACAG AAGAGAGUAC CAGAGAAACA CACGUUGUGG UACAUUACCU GGUA  54

( 2 ) INFORMATION FOR SEQ ID NO:713:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:713:

ACUCUCAGCU GUGUCUGG  18

( 2 ) INFORMATION FOR SEQ ID NO:714:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:714:

GAGCGGACAG AAGUGUCAAC CAGAGAAACA CACGUUGUGG UACAUUACCU GGUA  54

( 2 ) INFORMATION FOR SEQ ID NO:715:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:715:

UGACACAGCU GUCCGCUC ( 2 ) INFORMATION FOR SEQ ID NO:716:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:716:

GGUGAGCGAG AAGCUGUGAC CAGAGAAACA CACGUUGUGG UACAUUACCU GGUA  54

( 2 ) INFORMATION FOR SEQ ID NO:717:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:717:

CACAGCUGUC CGCUCACC  18

( 2 ) INFORMATION FOR SEQ ID NO:718:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:718:

GCUCGGUGAG AAGACAGCAC CAGAGAAACA CACGUUGUGG UACAUUACCU GGUA  54

( 2 ) INFORMATION FOR SEQ ID NO:719:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:719:

GCUGUCCGCU CACCGAGC                                               18

( 2 ) INFORMATION FOR SEQ ID NO:720:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:720:

UGCUUGUCAG AAGAGCUCAC CAGAGAAACA CACGUUGUGG UACAUUACCU GGUA     54

( 2 ) INFORMATION FOR SEQ ID NO:721:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:721:

GAGCUCUGUU GACAAGCA                                               18

( 2 ) INFORMATION FOR SEQ ID NO:722:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:722:

UGAGUAGGAG AAGGAAGCAC CAGAGAAACA CACGUUGUGG UACAUUACCU GGUA     54

( 2 ) INFORMATION FOR SEQ ID NO:723:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:723:

GCUUCCUGUC CCUACUCA                                               18

( 2 ) INFORMATION FOR SEQ ID NO:724:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:724:

CCCCCACGAG AAGUUUGAAC CAGAGAAACA CACGUUGUGG UACAUUACCU GGUA     54

( 2 ) INFORMATION FOR SEQ ID NO:725:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:725:

UCAAACUGUC CGUGGGGG                                                                                        18

( 2 ) INFORMATION FOR SEQ ID NO:726:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION:SEQ ID NO:726:

AAUCCAGGAG AAGCCUCGAC CAGAGAAACA CACGUUGUGG UACAUUACCU GGUA                                                 5

( 2 ) INFORMATION FOR SEQ ID NO:727:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:727:

CGAGGCAGUU CCUGGAUU                                                                                        18

( 2 ) INFORMATION FOR SEQ ID NO:728:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:728:

CACCAUGGAG AAGCUCAGAC CAGAGAAACA CACGUUGUGG UACAUUACCU GGUA                                                 54

( 2 ) INFORMATION FOR SEQ ID NO:729:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:729:

CUGAGCUGCU CCAUGGUG                                                                                        18

( 2 ) INFORMATION FOR SEQ ID NO:730:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:730:

GUUUUUGCAG AAGUUGACAC CAGAGAAACA CACGUUGUGG UACAUUACCU GGUA                                                 54

( 2 ) INFORMATION FOR SEQ ID NO:731:

( i ) SEQUENCE CHARACTERISTICS:

(A) LENGTH: 18 base pairs
                (B) TYPE: nucleic acid
                (C) STRANDEDNESS: single
                (D) TOPOLOGY: linear (xi) SEQUENCE DESCRIPTION: SEQ ID NO:731:

GUCAACAGAU GCAAAAAC                                                                                        18

(2) INFORMATION FOR SEQ ID NO:732:

(i) SEQUENCE CHARACTERISTICS:
                (A) LENGTH: 54 base pairs
                (B) TYPE: nucleic acid
                (C) STRANDEDNESS: single
                (D) TOPOLOGY: linear (xi) SEQUENCE DESCRIPTION: SEQ ID NO:732:

UAAAUGGAAG AAGCAUAUAC CAGAGAAACA CACGUUGUGG UACAUUACCU GGUA                                                 54

(2) INFORMATION FOR SEQ ID NO:733:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (xi) SEQUENCE DESCRIPTION: SEQ ID NO:733:

AUAUGCUGUU UCCAUUUA                                                                                        18

(2) INFORMATION FOR SEQ ID NO:734:

(i) SEQUENCE CHARACTERISTICS:
                (A) LENGTH: 54 base pairs
                (B) TYPE: nucleic acid
                (C) STRANDEDNESS: single
                (D) TOPOLOGY: linear (xi) SEQUENCE DESCRIPTION: SEQ ID NO:734:

GCAGGAGGAG AAGAAAUUAC CAGAGAAACA CACGUUGUGG UACAUUACCU GGUA                                                 54

(2) INFORMATION FOR SEQ ID NO:735:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (xi) SEQUENCE DESCRIPTION: SEQ ID NO:735:

AAUUUCUGAU CCUCCUGC                                                                                        18

(2) INFORMATION FOR SEQ ID NO:736:

(i) SEQUENCE CHARACTERISTICS:
                (A) LENGTH: 54 base pairs
                (B) TYPE: nucleic acid
                (C) STRANDEDNESS: single
                (D) TOPOLOGY: linear (xi) SEQUENCE DESCRIPTION: SEQ ID NO:736:

GAAGAGGAAG AAGGAGGAAC CAGAGAAACA CACGUUGUGG UACAUUACCU GGUA                                                 54

(2) INFORMATION FOR SEQ ID NO:737:

(i) SEQUENCE CHARACTERISTICS:
                (A) LENGTH: 18 base pairs
                (B) TYPE: nucleic acid ( C ) STRANDEDNESS: single
        ( D ) TOPOLOGY: linear ( x i ) SEQUENCE DESCRIPTION:SEQ ID NO:737:

UCCUCCUGCC UCCUCUUC ( 2 ) INFORMATION FOR SEQ ID NO:738:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:738:

AGUUCAAAAG AAGCCUGGAC CAGAGAAACA CACGUUGUGG UACAUUACCU GGUA   54

( 2 ) INFORMATION FOR SEQ ID NO:739:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:739:

CCAGGCUGAC UUUGAACU   18

( 2 ) INFORMATION FOR SEQ ID NO:740:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:740:

CUGCGUCCAG AAGGACCAAC CAGAGAAACA CACGUUGUGG UACAUUACCU GGUA   54

( 2 ) INFORMATION FOR SEQ ID NO:741:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:741:

UGGUCCAGAU GGACGCAG   18

( 2 ) INFORMATION FOR SEQ ID NO:742:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:742:

UAGAUAGGAG AAGGAAGCAC CAGAGAAACA CACGUUGUGG UACAUUACCU GGUA   54

( 2 ) INFORMATION FOR SEQ ID NO:743:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:743:

```
GCUUCCUGCU CCUAUCUA                                                                               18
```

( 2 ) INFORMATION FOR SEQ ID NO:744:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:744:

```
AUGGCACAAG AAGAUUCAAC CAGAGAAACA CACGUUGUGG UACAUUACCU GGUA         54
```

( 2 ) INFORMATION FOR SEQ ID NO:745:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:745:

```
UGAAUCAGAC UGUGCCAU                                                                               18
```

( 2 ) INFORMATION FOR SEQ ID NO:746:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:746:

```
CAAAAUCCAG AAGCUCCAAC CAGAGAAACA CACGUUGUGG UACAUUACCU GGUA         54
```

( 2 ) INFORMATION FOR SEQ ID NO:747:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:747:

```
UGGAGCAGCU GGAUUUUG                                                                               18
```

( 2 ) INFORMATION FOR SEQ ID NO:748:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:748:

```
CUGGAGUAAG AAGGGGAAC CAGAGAAACA CACGUUGUGG UACAUUACCU GGUA           5
```

( 2 ) INFORMATION FOR SEQ ID NO:749:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:749:

```
UCCCCCAGUU UACUCCAG                                                                               18
```

(2) INFORMATION FOR SEQ ID NO:750:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:750:

AAGCAUACAG AAGUUUUAC CAGAGAAACA CACGUUGUGG UACAUUACCU GGUA     54

(2) INFORMATION FOR SEQ ID NO:751:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:751:

AAAAACAGAU GUAUGCUU     18